(12) United States Patent
Borja

(10) Patent No.: US 12,232,863 B2
(45) Date of Patent: *Feb. 25, 2025

(54) HIP SURGERY SYSTEMS AND METHODS

(71) Applicant: OrthAlign, Inc., Aliso Viejo, CA (US)

(72) Inventor: Santiago P. Borja, Tucson, AZ (US)

(73) Assignee: OrthAlign, Inc., Irvine, CA (US)

( * ) Notice: Subject to any disclaimer, the term of this patent is extended or adjusted under 35 U.S.C. 154(b) by 194 days.

This patent is subject to a terminal disclaimer.

(21) Appl. No.: 18/148,008

(22) Filed: Dec. 29, 2022

(65) Prior Publication Data

US 2023/0135541 A1    May 4, 2023

Related U.S. Application Data

(63) Continuation of application No. 17/529,683, filed on Nov. 18, 2021, now Pat. No. 11,540,746, which is a
(Continued)

(51) Int. Cl.
*A61F 2/46*      (2006.01)
*A61B 5/107*     (2006.01)
(Continued)

(52) U.S. Cl.
CPC .......... *A61B 5/1072* (2013.01); *A61B 5/1077* (2013.01); *A61B 5/1079* (2013.01); *A61F 2/4657* (2013.01); *A61B 2090/067* (2016.02); *A61B 2090/0809* (2016.02); *A61F 2/32* (2013.01); *A61F 2/4607* (2013.01);
(Continued)

(58) Field of Classification Search
CPC ........ A61F 2/46; A61F 2/4657; A61F 2/4607; A61F 2/4609; A61F 2/32; A61B 5/107; A61B 5/1072; A61B 5/1077; A61B 5/1079
See application file for complete search history.

(56) References Cited

U.S. PATENT DOCUMENTS

| | | |
|---|---|---|
| 3,174,080 A | 3/1965 | Eldon |
| 3,670,324 A | 6/1972 | Trevor, 3rd |

(Continued)

FOREIGN PATENT DOCUMENTS

| | | |
|---|---|---|
| CA | 2241359 | 12/1999 |
| CA | 2 594 874 | 7/2006 |

(Continued)

OTHER PUBLICATIONS 510 (k) Summary for Total Knee Surgetics Navigation System, in 5 pages.
(Continued)

*Primary Examiner* — Christopher J Beccia
(74) *Attorney, Agent, or Firm* — Knobbe, Martens, Olson & Bear, LLP

(57) ABSTRACT

Orthopedic systems and methods are provided for use in preparing joints for implants. Specifically, hip preparation systems and methods are disclosed which can include a surgical orientation device. The hip preparation systems and methods can be used, for example, to orient the hip during the procedure, determine the orientation of an anatomical plane or planes, and orient a prosthetic component or components.

20 Claims, 46 Drawing Sheets

Related U.S. Application Data continuation of application No. 16/402,614, filed on May 3, 2019, now Pat. No. 11,179,062, which is a continuation of application No. 15/899,790, filed on Feb. 20, 2018, now Pat. No. 10,321,852, which is a continuation of application No. 14/639,784, filed on Mar. 5, 2015, now Pat. No. 9,931,059, which is a continuation of application No. 13/444,142, filed on Apr. 11, 2012, now Pat. No. 8,974,468, which is a continuation of application No. 12/625,445, filed on Nov. 24, 2009, now abandoned, which is a continuation of application No. 12/557,051, filed on Sep. 10, 2009, now abandoned.

(60) Provisional application No. 61/226,668, filed on Jul. 17, 2009, provisional application No. 61/191,603, filed on Sep. 10, 2008.

(51) Int. Cl.
  A61B 90/00   (2016.01)
  A61F 2/32    (2006.01)

(52) U.S. Cl.
  CPC ..... A61F 2/4609 (2013.01); A61F 2002/4658 (2013.01); A61F 2002/4668 (2013.01); A61F 2002/4687 (2013.01)

(56) References Cited

U.S. PATENT DOCUMENTS

| | | |
|---|---|---|
| 4,349,018 A | 9/1982 | Chambers |
| 4,421,112 A | 12/1983 | Mains et al. |
| 4,436,099 A | 3/1984 | Raftopoulos |
| 4,459,985 A | 7/1984 | Mckay et al. |
| 4,475,549 A | 10/1984 | Oh |
| 4,501,266 A | 2/1985 | McDaniel |
| 4,509,393 A | 4/1985 | Castiglione |
| 4,518,855 A | 5/1985 | Malak |
| 4,524,766 A | 6/1985 | Petersen |
| 4,529,348 A | 7/1985 | Johnson et al. |
| 4,567,885 A | 2/1986 | Androphy |
| 4,567,886 A | 2/1986 | Petersen |
| 4,621,630 A | 11/1986 | Kenna |
| 4,646,729 A | 3/1987 | Kenna |
| 4,716,894 A | 1/1988 | Lazzeri et al. |
| 4,718,078 A | 1/1988 | Bleidorn et al. |
| 4,738,253 A | 4/1988 | Buechel et al. |
| 4,759,350 A | 7/1988 | Dunn et al. |
| 4,823,807 A | 4/1989 | Russell et al. |
| 4,938,762 A | 7/1990 | Wehrli |
| 4,944,760 A | 7/1990 | Kenna |
| 4,945,799 A | 8/1990 | Knetzer |
| 4,952,213 A | 8/1990 | Bowman et al. |
| 5,002,547 A | 3/1991 | Poggie et al. |
| 5,053,037 A | 10/1991 | Lackey |
| 5,065,612 A | 11/1991 | Ooka et al. |
| 5,067,821 A | 11/1991 | Young |
| 5,116,338 A | 5/1992 | Poggie et al. |
| 5,122,146 A | 6/1992 | Chapman et al. |
| 5,129,908 A | 7/1992 | Petersen |
| 5,141,512 A | 8/1992 | Farmer et al. |
| 5,171,244 A | 12/1992 | Caspari et al. |
| 5,213,112 A | 5/1993 | Niwa et al. |
| 5,249,581 A | 10/1993 | Horbal et al. |
| 5,251,127 A | 10/1993 | Raab |
| 5,279,309 A | 1/1994 | Taylor et al. |
| 5,296,855 A | 3/1994 | Matsuzaki et al. |
| 5,306,276 A | 4/1994 | Johnson et al. |
| 5,320,625 A | 6/1994 | Bertin |
| 5,324,293 A | 6/1994 | Rehmann |
| 5,325,029 A | 6/1994 | Janecke et al. |
| 5,329,933 A | 7/1994 | Graf |
| 5,342,367 A | 8/1994 | Ferrante et al. |
| 5,343,391 A | 8/1994 | Mushabac |
| 5,358,526 A | 10/1994 | Tornier |
| 5,376,093 A | 12/1994 | Newman |
| 5,395,377 A | 3/1995 | Petersen et al. |
| 5,417,694 A | 5/1995 | Marik et al. |
| 5,423,827 A | 6/1995 | Mumme |
| 5,431,653 A | 7/1995 | Callaway |
| 5,462,548 A | 10/1995 | Pappas et al. |
| 5,468,244 A | 11/1995 | Attfield et al. |
| 5,474,088 A | 12/1995 | Zaharkin et al. |
| 5,486,177 A | 1/1996 | Mumme et al. |
| 5,514,143 A | 5/1996 | Bonutti et al. |
| 5,529,070 A | 6/1996 | Augustine et al. |
| 5,540,696 A | 7/1996 | Booth, Jr. et al. |
| 5,540,697 A | 7/1996 | Rehmann et al. |
| 5,553,198 A | 9/1996 | Wang et al. |
| 5,576,727 A | 11/1996 | Rosenberg et al. |
| 5,584,837 A | 12/1996 | Peterson |
| 5,597,379 A | 1/1997 | Haines et al. |
| 5,611,353 A | 3/1997 | Dance et al. |
| 5,624,444 A | 4/1997 | Wixson et al. |
| 5,628,750 A | 5/1997 | Whitlock et al. |
| 5,645,077 A | 7/1997 | Foxlin |
| 5,653,764 A | 8/1997 | Murphy |
| 5,681,316 A | 10/1997 | DeOrio et al. |
| 5,683,398 A | 11/1997 | Carls et al. |
| 5,688,282 A | 11/1997 | Baron et al. |
| 5,720,752 A | 2/1998 | Elliot et al. |
| 5,724,264 A | 3/1998 | Rosenberg et al. |
| 5,748,767 A | 5/1998 | Raab |
| 5,769,861 A | 6/1998 | Vilsmeier |
| 5,776,137 A | 7/1998 | Katz |
| 5,788,700 A | 8/1998 | Morawa et al. |
| 5,824,085 A | 10/1998 | Sahay et al. |
| 5,840,047 A | 11/1998 | Stedham |
| 5,880,714 A | 3/1999 | Rosenberg et al. |
| 5,916,219 A | 6/1999 | Matsuno et al. |
| 5,919,149 A | 7/1999 | Allum |
| 5,935,086 A | 8/1999 | Beacon et al. |
| 5,976,156 A | 11/1999 | Taylor et al. |
| 6,027,507 A | 2/2000 | Anderson et al. |
| 6,036,696 A | 3/2000 | Lambrecht et al. |
| 6,056,756 A | 5/2000 | Eng et al. |
| 6,090,114 A | 7/2000 | Matsuno et al. |
| 6,094,019 A | 7/2000 | Saiki |
| 6,120,509 A | 9/2000 | Wheeler |
| 6,122,538 A | 9/2000 | Sliwa, Jr. et al. |
| 6,126,608 A | 10/2000 | Kemme et al. |
| 6,162,191 A | 12/2000 | Foxin |
| 6,167,292 A | 12/2000 | Badano et al. |
| 6,171,310 B1 | 1/2001 | Giordano |
| 6,195,615 B1 | 2/2001 | Lysen |
| 6,197,032 B1 | 3/2001 | Lawes et al. |
| 6,214,013 B1 | 4/2001 | Lambrech et al. |
| 6,214,014 B1 | 4/2001 | McGann |
| 6,216,029 B1 | 4/2001 | Paltieli |
| 6,246,898 B1 | 6/2001 | Vesely et al. |
| 6,258,095 B1 | 7/2001 | Lombardo et al. |
| 6,261,247 B1 | 7/2001 | Ishikawa et al. |
| 6,299,646 B1 | 10/2001 | Chambat et al. |
| 6,332,089 B1 | 12/2001 | Acker |
| 6,348,058 B1 | 2/2002 | Melken et al. |
| 6,354,011 B1 | 3/2002 | Albrecht |
| 6,361,506 B1 | 3/2002 | Saenger et al. |
| 6,361,507 B1 | 3/2002 | Foxlin |
| 6,361,508 B1 | 3/2002 | Johnson et al. |
| 6,377,839 B1 | 4/2002 | Kalfas et al. |
| 6,381,485 B1 | 4/2002 | Hunter et al. |
| 6,383,149 B1 | 5/2002 | DeMayo |
| 6,395,005 B1 | 5/2002 | Lovell |
| 6,447,448 B1 | 9/2002 | Ishikawa et al. |
| 6,468,280 B1 | 10/2002 | Saenger et al. |
| 6,470,207 B1 | 10/2002 | Simon et al. |
| 6,471,637 B1 | 10/2002 | Green et al. |
| 6,473,635 B1 | 10/2002 | Rasche |
| 6,477,400 B1 | 11/2002 | Barrick |
| 6,477,421 B1 | 11/2002 | Andersen et al. |
| 6,478,799 B1 | 11/2002 | Williamson |
| 6,488,713 B1 | 12/2002 | Hershnerger |

(56) References Cited

U.S. PATENT DOCUMENTS

| | | |
|---|---|---|
| 6,499,488 B1 | 12/2002 | Hunter et al. |
| 6,514,259 B2 | 2/2003 | Picard et al. |
| 6,527,443 B1 | 3/2003 | Vilsmeier |
| 6,551,325 B2 | 4/2003 | Neubauer et al. |
| 6,585,666 B2 | 7/2003 | Suh et al. |
| 6,595,997 B2 | 7/2003 | Axelson, Jr. et al. |
| 6,595,999 B2 | 7/2003 | Marchione et al. |
| 6,607,487 B2 | 8/2003 | Chang et al. |
| 6,640,128 B2 | 10/2003 | Vilsmeier et al. |
| 6,648,896 B2 | 11/2003 | Overes et al. |
| 6,679,916 B1 | 1/2004 | Frankie et al. |
| 6,685,655 B2 | 2/2004 | DeMayo |
| 6,685,711 B2 | 2/2004 | Axelson et al. |
| 6,711,431 B2 | 3/2004 | Sarin et al. |
| 6,712,824 B2 | 3/2004 | Millard et al. |
| 6,715,213 B2 | 4/2004 | Richter |
| 6,725,080 B2 | 4/2004 | Melkent et al. |
| 6,725,173 B2 | 4/2004 | An |
| 6,743,235 B2 | 6/2004 | Rao |
| 6,770,078 B2 | 8/2004 | Bonutti |
| 6,786,877 B2 | 9/2004 | Foxlin |
| 6,802,864 B2 | 10/2004 | Tornier |
| 6,817,470 B1 | 11/2004 | Goldberg |
| 6,820,025 B2 | 11/2004 | Bachmann et al. |
| 6,827,723 B2 | 12/2004 | Carson |
| 6,917,827 B2 | 7/2005 | Kienzle, III |
| 6,923,817 B2 | 8/2005 | Carson et al. |
| 6,928,742 B2 | 8/2005 | Broers et al. |
| 6,947,783 B2 | 9/2005 | Immerz |
| 6,986,181 B2 | 1/2006 | Murphy et al. |
| 6,997,882 B1 | 2/2006 | Parker et al. |
| 7,007,699 B2 | 3/2006 | Martinelli et al. |
| 7,021,140 B2 | 4/2006 | Perkins |
| 7,027,477 B2 | 4/2006 | Sutter et al. |
| 7,037,310 B2 | 5/2006 | Murphy |
| 7,048,741 B2 | 5/2006 | Swanson |
| 7,089,148 B1 | 8/2006 | Bachmann et al. |
| 7,094,241 B2 | 8/2006 | Hodorek et al. |
| 7,104,998 B2 | 9/2006 | Yoon et al. |
| 7,105,028 B2 | 9/2006 | Murphy |
| 7,194,295 B2 | 3/2007 | Vilsmeier |
| 7,209,776 B2 | 4/2007 | Leitner |
| 7,219,033 B2 | 5/2007 | Kolen |
| 7,273,500 B2 | 9/2007 | Williamson |
| 7,311,441 B2 | 12/2007 | Weaver et al. |
| 7,331,932 B2 | 2/2008 | Leitner |
| 7,344,541 B2 | 3/2008 | Haines et al. |
| 7,392,076 B2 | 6/2008 | Moctezuma de La Barrera |
| 7,396,357 B2 | 7/2008 | Tornier et al. |
| 7,444,178 B2 | 10/2008 | Goldbach |
| 7,468,075 B2 | 12/2008 | Lang et al. |
| 7,468,077 B2 | 12/2008 | Rochetin |
| 7,497,029 B2 | 3/2009 | Plassky et al. |
| 7,520,880 B2 | 4/2009 | Claypool et al. |
| 7,547,307 B2 | 6/2009 | Carson et al. |
| 7,559,931 B2 | 7/2009 | Stone |
| 7,578,821 B2 | 8/2009 | Fisher et al. |
| 7,594,933 B2 | 9/2009 | Kammerzell et al. |
| 7,611,520 B2 | 11/2009 | Broers et al. |
| 7,611,522 B2 | 11/2009 | Gorek |
| 7,621,920 B2 | 11/2009 | Claypool et al. |
| 7,623,902 B2 | 11/2009 | Pacheco |
| 7,726,564 B2 | 6/2010 | Goldbach |
| 7,776,098 B2 | 8/2010 | Murphy |
| 7,815,644 B2 | 10/2010 | Masini |
| 7,831,292 B2 | 11/2010 | Quaid et al. |
| 7,834,847 B2 | 11/2010 | Boillot et al. |
| 7,840,256 B2 | 11/2010 | Lakin et al. |
| 7,846,092 B2 | 12/2010 | Murphy |
| 7,857,821 B2 | 12/2010 | Couture et al. |
| 7,885,705 B2 | 2/2011 | Murphy |
| 7,970,174 B2 | 6/2011 | Goldbach |
| 8,057,479 B2 | 11/2011 | Stone |
| 8,057,482 B2 | 11/2011 | Stone |
| 8,078,254 B2 | 12/2011 | Murphy |
| 8,104,960 B2 | 1/2012 | Gill et al. |
| 8,118,815 B2 | 2/2012 | van der Walt |
| 8,241,296 B2 | 8/2012 | Wasielewski |
| 8,265,790 B2 | 9/2012 | Amiot et al. |
| 8,267,938 B2 | 9/2012 | Murphy |
| 8,277,455 B2 | 10/2012 | Couture et al. |
| 8,282,685 B2 | 10/2012 | Rochetin et al. |
| 8,355,773 B2 | 1/2013 | Leitner et al. |
| 8,412,308 B2 | 4/2013 | Goldbach |
| 8,421,854 B2 | 4/2013 | Zerkin |
| 8,446,473 B2 | 5/2013 | Goldbach |
| 8,512,346 B2 | 8/2013 | Couture |
| 8,551,108 B2 | 10/2013 | Pelletier et al. |
| 8,588,892 B2 | 11/2013 | Hladio et al. |
| 8,690,888 B2 | 4/2014 | Stein et al. |
| 8,718,820 B2 | 5/2014 | Amiot et al. |
| 8,734,432 B2 | 5/2014 | Tuma et al. |
| 8,764,758 B2 | 7/2014 | Echeverri |
| 8,867,198 B2 | 10/2014 | Steele |
| 8,888,786 B2 | 11/2014 | Stone |
| 8,911,447 B2 | 12/2014 | van der Walt et al. |
| 8,974,467 B2 | 3/2015 | Stone |
| 8,974,468 B2 | 3/2015 | Borja |
| 8,998,910 B2 | 4/2015 | Borja et al. |
| 9,044,218 B2 | 6/2015 | Young |
| 9,138,319 B2 | 9/2015 | Fanson et al. |
| 9,192,392 B2 | 11/2015 | van der Walt et al. |
| 9,262,802 B2 | 2/2016 | Aghazadeh |
| 9,271,756 B2 | 3/2016 | van der Walt et al. |
| 9,339,226 B2 | 5/2016 | van der Walt et al. |
| 9,375,178 B2 | 6/2016 | Aghazadeh |
| 9,456,769 B2 | 10/2016 | Stein et al. |
| 9,549,742 B2 | 1/2017 | Berend et al. |
| 9,572,586 B2 | 2/2017 | van der Walt et al. |
| 9,642,572 B2 | 5/2017 | Mahfouz et al. |
| 9,649,160 B2 | 5/2017 | van der Walt et al. |
| 9,775,725 B2 | 10/2017 | van der Walt et al. |
| 9,855,075 B2 | 1/2018 | van der Walt et al. |
| 9,930,946 B2 | 4/2018 | Zondervan |
| 9,931,059 B2 | 4/2018 | Borja |
| 10,206,714 B2 | 2/2019 | van der Walt et al. |
| 10,238,510 B2 | 3/2019 | van der Walt et al. |
| 10,321,852 B2 | 6/2019 | Borja |
| 10,363,149 B2 | 7/2019 | van der Walt et al. |
| 10,597,178 B2 | 3/2020 | Ryterski et al. |
| 10,603,115 B2 | 3/2020 | van der Walt et al. |
| 10,716,580 B2 | 7/2020 | Berend et al. |
| 10,863,995 B2 | 12/2020 | Nielsen et al. |
| 10,864,019 B2 | 12/2020 | van der Walt et al. |
| 10,869,771 B2 | 12/2020 | van der Walt et al. |
| 10,918,499 B2 | 2/2021 | Nielsen et al. |
| 11,020,245 B2 | 6/2021 | van der Walt et al. |
| 11,179,062 B2 | 11/2021 | Borja et al. |
| 11,179,167 B2 | 11/2021 | Stone |
| 11,191,334 B2 | 12/2021 | Aghazadeh et al. |
| 11,273,232 B2 | 3/2022 | Placik |
| 11,540,746 B2 * | 1/2023 | Borja .................. A61B 5/1079 |
| 11,547,451 B2 | 1/2023 | van der Walt et al. |
| 11,547,580 B2 | 1/2023 | Nielsen et al. |
| 11,633,293 B2 | 4/2023 | van der Walt et al. |
| 11,653,981 B2 | 5/2023 | van der Walt et al. |
| 11,684,392 B2 | 6/2023 | van der Walt et al. |
| 11,786,261 B2 | 10/2023 | Nielsen et al. |
| 11,871,965 B2 | 1/2024 | van der Walt et al. |
| 11,903,597 B2 | 2/2024 | Stone |
| 11,911,119 B2 | 2/2024 | van der Walt et al. |
| 2002/0077540 A1 * | 6/2002 | Kienzle, III ........ A61B 17/1703 |
| | | 606/130 |
| 2002/0103610 A1 | 8/2002 | Bachmann et al. |
| 2002/0107522 A1 | 8/2002 | Picard et al. |
| 2002/0133175 A1 | 9/2002 | Carson |
| 2002/0198451 A1 | 12/2002 | Carson |
| 2003/0019294 A1 | 1/2003 | Richter |
| 2003/0069591 A1 | 4/2003 | Carson et al. |
| 2003/0093080 A1 | 5/2003 | Brown et al. |
| 2003/0105470 A1 | 6/2003 | White |
| 2003/0120282 A1 | 6/2003 | Scouten et al. |
| 2003/0163142 A1 | 8/2003 | Paltieli et al. |
| 2003/0181919 A1 | 9/2003 | Gorek |

(56) References Cited

U.S. PATENT DOCUMENTS

| | | |
|---|---|---|
| 2003/0184297 A1 | 10/2003 | Jakab |
| 2003/0199882 A1 | 10/2003 | Gorek |
| 2003/0204965 A1 | 11/2003 | Hennessey |
| 2003/0229356 A1 | 12/2003 | Dye |
| 2004/0006393 A1 | 1/2004 | Burkinshaw |
| 2004/0019382 A1 | 1/2004 | Amirouche et al. |
| 2004/0034313 A1 | 2/2004 | Leitner |
| 2004/0039396 A1 | 2/2004 | Couture et al. |
| 2004/0068260 A1 | 4/2004 | Cossette et al. |
| 2004/0073225 A1 | 4/2004 | Subba Rao |
| 2004/0087958 A1 | 5/2004 | Myers et al. |
| 2004/0087962 A1 | 5/2004 | Gorek |
| 2004/0097952 A1 | 5/2004 | Sarin et al. |
| 2004/0102792 A1 | 5/2004 | Sarin et al. |
| 2004/0106916 A1 | 6/2004 | Quaid et al. |
| 2004/0122441 A1 | 6/2004 | Muratsu |
| 2004/0147926 A1 | 7/2004 | Iversen |
| 2004/0149036 A1 | 8/2004 | Foxlin et al. |
| 2004/0152955 A1 | 8/2004 | McGinley et al. |
| 2004/0152970 A1 | 8/2004 | Hunter et al. |
| 2004/0153066 A1 | 8/2004 | Coon et al. |
| 2004/0153079 A1 | 8/2004 | Tsougarakis et al. |
| 2004/0181144 A1 | 9/2004 | Cinquin et al. |
| 2004/0201857 A1 | 10/2004 | Foxlin |
| 2004/0230197 A1 | 11/2004 | Tornier et al. |
| 2004/0243148 A1 | 12/2004 | Wasielewski |
| 2005/0021037 A1 | 1/2005 | McCombs et al. |
| 2005/0021044 A1 | 1/2005 | Stone et al. |
| 2005/0070864 A1 | 3/2005 | Fellion |
| 2005/0107799 A1 | 5/2005 | Graf et al. |
| 2005/0113846 A1* | 5/2005 | Carson .................. A61B 90/10 606/130 |
| 2005/0149040 A1 | 7/2005 | Haines et al. |
| 2005/0149054 A1 | 7/2005 | Gorek |
| 2005/0197814 A1 | 9/2005 | Aram et al. |
| 2005/0209605 A1 | 9/2005 | Grimm et al. |
| 2005/0222574 A1 | 10/2005 | Giordano et al. |
| 2005/0234332 A1 | 10/2005 | Murphy |
| 2005/0251026 A1* | 11/2005 | Stone .................... A61B 34/20 600/407 |
| 2005/0251148 A1 | 11/2005 | Friedrich |
| 2006/0009780 A1 | 1/2006 | Foley et al. |
| 2006/0015018 A1 | 1/2006 | Jutras et al. |
| 2006/0015120 A1 | 1/2006 | Richard et al. |
| 2006/0020177 A1 | 1/2006 | Seo et al. |
| 2006/0064105 A1 | 3/2006 | Raistrick et al. |
| 2006/0084977 A1 | 4/2006 | Lieberman |
| 2006/0089657 A1 | 4/2006 | Broers et al. |
| 2006/0094958 A1 | 5/2006 | Marquart et al. |
| 2006/0122491 A1 | 6/2006 | Murray et al. |
| 2006/0142656 A1 | 6/2006 | Malackowski et al. |
| 2006/0142657 A1 | 6/2006 | Quaid et al. |
| 2006/0149276 A1 | 7/2006 | Grimm |
| 2006/0161051 A1 | 7/2006 | Terrill-Grisoni et al. |
| 2006/0217733 A1 | 9/2006 | Plassky et al. |
| 2006/0217734 A1 | 9/2006 | Sanford et al. |
| 2006/0241639 A1 | 10/2006 | Kuczynski et al. |
| 2006/0270949 A1 | 11/2006 | Mathie et al. |
| 2006/0282023 A1 | 12/2006 | Leitner |
| 2007/0016009 A1* | 1/2007 | Lakin .................... A61B 90/39 600/424 |
| 2007/0032748 A1 | 2/2007 | McNeil et al. |
| 2007/0043287 A1 | 2/2007 | Degraaf |
| 2007/0043375 A1 | 2/2007 | Anissian |
| 2007/0073296 A1 | 3/2007 | Panchbhavi |
| 2007/0100346 A1 | 5/2007 | Wyss et al. |
| 2007/0162142 A1 | 7/2007 | Stone |
| 2007/0179626 A1 | 8/2007 | de la Barrera et al. |
| 2007/0179628 A1 | 8/2007 | Rochetin |
| 2007/0219559 A1 | 9/2007 | Heavener et al. |
| 2007/0219561 A1 | 9/2007 | Lavallee et al. |
| 2007/0226986 A1 | 10/2007 | Park et al. |
| 2007/0244488 A1 | 10/2007 | Metzger et al. |
| 2007/0249967 A1 | 10/2007 | Buly et al. |
| 2007/0270718 A1 | 11/2007 | Rochetin et al. |
| 2007/0270973 A1 | 11/2007 | Johnson et al. |
| 2007/0287911 A1 | 12/2007 | Haid et al. |
| 2008/0058945 A1 | 3/2008 | Hajaj et al. |
| 2008/0071195 A1 | 3/2008 | Cuellar et al. |
| 2008/0103509 A1 | 5/2008 | Goldbach |
| 2008/0108912 A1 | 5/2008 | Node-Langlois |
| 2008/0162074 A1 | 7/2008 | Schneider |
| 2008/0183179 A1 | 7/2008 | Siebel et al. |
| 2008/0195109 A1 | 8/2008 | Hunter et al. |
| 2008/0202200 A1 | 8/2008 | West |
| 2008/0211768 A1 | 9/2008 | Breen et al. |
| 2008/0243127 A1 | 10/2008 | Lang et al. |
| 2008/0249394 A1 | 10/2008 | Giori et al. |
| 2008/0262812 A1 | 10/2008 | Arata et al. |
| 2008/0275451 A1 | 11/2008 | McAllister et al. |
| 2008/0281328 A1 | 11/2008 | Lang et al. |
| 2008/0285805 A1 | 11/2008 | Luinge et al. |
| 2009/0000626 A1 | 1/2009 | Quaid et al. |
| 2009/0000627 A1 | 1/2009 | Quaid et al. |
| 2009/0012532 A1 | 1/2009 | Quaid et al. |
| 2009/0040224 A1 | 2/2009 | Igarashi et al. |
| 2009/0070038 A1 | 3/2009 | Geelen et al. |
| 2009/0076507 A1 | 3/2009 | Claypool et al. |
| 2009/0076519 A1 | 3/2009 | Iversen |
| 2009/0088753 A1 | 4/2009 | Aram et al. |
| 2009/0099665 A1 | 4/2009 | Taylor et al. |
| 2009/0171370 A1 | 7/2009 | Yoon et al. |
| 2009/0209884 A1 | 8/2009 | Van Vorhis et al. |
| 2009/0216247 A1 | 8/2009 | Collette |
| 2009/0216285 A1 | 8/2009 | Ek |
| 2009/0234360 A1 | 9/2009 | Alexander |
| 2009/0247863 A1 | 10/2009 | Proulx et al. |
| 2009/0248044 A1 | 10/2009 | Amiot et al. |
| 2009/0264737 A1 | 10/2009 | Haechler et al. |
| 2009/0270864 A1 | 10/2009 | Poncet |
| 2009/0270865 A1 | 10/2009 | Poncet et al. |
| 2009/0270868 A1 | 10/2009 | Park et al. |
| 2009/0270869 A1 | 10/2009 | Colquhoun et al. |
| 2009/0270874 A1 | 10/2009 | Santarella et al. |
| 2009/0270875 A1 | 10/2009 | Poncet |
| 2009/0270928 A1 | 10/2009 | Stone et al. |
| 2009/0276054 A1 | 11/2009 | Clifford et al. |
| 2009/0281545 A1 | 11/2009 | Stubbs |
| 2009/0289806 A1 | 11/2009 | Thornberry |
| 2009/0292227 A1 | 11/2009 | Scholten et al. |
| 2009/0299416 A1 | 12/2009 | Haenni et al. |
| 2009/0299483 A1 | 12/2009 | Amirouche et al. |
| 2009/0306679 A1 | 12/2009 | Murphy |
| 2009/0312973 A1 | 12/2009 | Hatlestad et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2009/0324078 A1 | 12/2009 | Wu et al. |
| 2010/0016705 A1 | 1/2010 | Stone |
| 2010/0023018 A1 | 1/2010 | Theofilos |
| 2010/0063509 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0087829 A1 | 4/2010 | Metzger et al. |
| 2010/0100011 A1 | 4/2010 | Roche |
| 2010/0100154 A1 | 4/2010 | Roche |
| 2010/0113980 A1 | 5/2010 | Herr et al. |
| 2010/0121334 A1 | 5/2010 | Couture et al. |
| 2010/0137869 A1 | 6/2010 | Borja et al. |
| 2010/0137871 A1 | 6/2010 | Borja |
| 2010/0153081 A1 | 6/2010 | Bellettre et al. |
| 2010/0179605 A1 | 7/2010 | Branch et al. |
| 2010/0182914 A1 | 7/2010 | DelRegno et al. |
| 2010/0192662 A1 | 8/2010 | Yanni |
| 2010/0198067 A1 | 8/2010 | Mahfouz et al. |
| 2010/0198275 A1 | 8/2010 | Chana |
| 2010/0204551 A1 | 8/2010 | Roche |
| 2010/0204575 A1 | 8/2010 | Roche et al. |
| 2010/0204955 A1 | 8/2010 | Roche et al. |
| 2010/0211077 A1 | 8/2010 | Couture et al. |
| 2010/0239996 A1 | 9/2010 | Ertl |
| 2010/0241126 A1 | 9/2010 | Ghijselings |
| 2010/0249533 A1 | 9/2010 | Pierce et al. |

(56) References Cited

U.S. PATENT DOCUMENTS

| | | |
|---|---|---|
| 2010/0249534 A1 | 9/2010 | Pierce et al. |
| 2010/0249535 A1 | 9/2010 | Pierce et al. |
| 2010/0249659 A1 | 9/2010 | Sherman et al. |
| 2010/0249665 A1 | 9/2010 | Roche |
| 2010/0249787 A1 | 9/2010 | Roche |
| 2010/0249788 A1 | 9/2010 | Roche |
| 2010/0249790 A1 | 9/2010 | Roche |
| 2010/0249791 A1 | 9/2010 | Roche |
| 2010/0250276 A1 | 9/2010 | Pierce et al. |
| 2010/0250284 A1 | 9/2010 | Roche et al. |
| 2010/0250571 A1 | 9/2010 | Pierce et al. |
| 2010/0256504 A1 | 10/2010 | Moreau-Gaudry et al. |
| 2010/0261998 A1 | 10/2010 | Stiehl |
| 2010/0268067 A1 | 10/2010 | Razzaque et al. |
| 2010/0298661 A1 | 11/2010 | McCombie et al. |
| 2010/0324457 A1 | 12/2010 | Bean et al. |
| 2010/0326187 A1 | 12/2010 | Stein |
| 2010/0326194 A1 | 12/2010 | Stein et al. |
| 2010/0326210 A1 | 12/2010 | Stein et al. |
| 2010/0326211 A1 | 12/2010 | Stein |
| 2010/0327848 A1 | 12/2010 | Stein |
| 2010/0327880 A1 | 12/2010 | Stein |
| 2010/0328077 A1 | 12/2010 | Stein |
| 2010/0328098 A1 | 12/2010 | Stein et al. |
| 2010/0331633 A1 | 12/2010 | Stein |
| 2010/0331663 A1 | 12/2010 | Stein |
| 2010/0331679 A1 | 12/2010 | Stein |
| 2010/0331680 A1 | 12/2010 | Stein |
| 2010/0331681 A1 | 12/2010 | Stein et al. |
| 2010/0331682 A1 | 12/2010 | Stein et al. |
| 2010/0331683 A1 | 12/2010 | Stein et al. |
| 2010/0331685 A1 | 12/2010 | Stein et al. |
| 2010/0331687 A1 | 12/2010 | Stein et al. |
| 2010/0331704 A1 | 12/2010 | Stein et al. |
| 2010/0331718 A1 | 12/2010 | Stein |
| 2010/0331733 A1 | 12/2010 | Stein |
| 2010/0331734 A1 | 12/2010 | Stein |
| 2010/0331735 A1 | 12/2010 | Stein |
| 2010/0331736 A1 | 12/2010 | Stein |
| 2010/0331737 A1 | 12/2010 | Stein et al. |
| 2010/0331738 A1 | 12/2010 | Stein et al. |
| 2010/0331894 A1 | 12/2010 | Stein |
| 2010/0332152 A1 | 12/2010 | Stein |
| 2011/0028865 A1 | 2/2011 | Luinge et al. |
| 2011/0032184 A1 | 2/2011 | Roche et al. |
| 2011/0093081 A1 | 4/2011 | Chana |
| 2011/0213275 A1 | 9/2011 | Boos et al. |
| 2011/0218458 A1 | 9/2011 | Valin et al. |
| 2011/0218546 A1 | 9/2011 | De La Fuente Klein et al. |
| 2011/0275957 A1 | 11/2011 | Bhandari |
| 2012/0029389 A1 | 2/2012 | Amiot et al. |
| 2012/0053488 A1 | 3/2012 | Boutin et al. |
| 2012/0053594 A1 | 3/2012 | Pelletier et al. |
| 2012/0093377 A1 | 4/2012 | Tsougarakis et al. |
| 2012/0157887 A1 | 6/2012 | Fanson et al. |
| 2012/0172712 A1 | 7/2012 | Bar-Tal |
| 2012/0172884 A1 | 7/2012 | Zheng et al. |
| 2012/0203140 A1 | 8/2012 | Malchau et al. |
| 2013/0053859 A1 | 2/2013 | Penenberg |
| 2013/0064478 A1 | 3/2013 | Sold et al. |
| 2013/0066323 A1 | 3/2013 | Nycz et al. |
| 2013/0079678 A1 | 3/2013 | Stein et al. |
| 2013/0079679 A1 | 3/2013 | Roche et al. |
| 2013/0079680 A1 | 3/2013 | Stein et al. |
| 2013/0079790 A1 | 3/2013 | Stein et al. |
| 2013/0079791 A1 | 3/2013 | Stein et al. |
| 2013/0079793 A1 | 3/2013 | Stein et al. |
| 2013/0190887 A1 | 7/2013 | Fanson et al. |
| 2013/0274633 A1 | 10/2013 | Hladio et al. |
| 2014/0005673 A1 | 1/2014 | Pelletier et al. |
| 2014/0031672 A1 | 1/2014 | McCaulley et al. |
| 2014/0114179 A1 | 4/2014 | Muller et al. |
| 2014/0134586 A1 | 5/2014 | Stein et al. |
| 2014/0135658 A1 | 5/2014 | Hladio et al. |
| 2014/0135744 A1 | 5/2014 | Stein et al. |
| 2014/0135773 A1 | 5/2014 | Stein et al. |
| 2014/0136143 A1 | 5/2014 | Stein et al. |
| 2014/0182062 A1 | 7/2014 | Aghazadeh |
| 2014/0224685 A1 | 8/2014 | Carnevali |
| 2014/0270583 A1 | 9/2014 | Anderson |
| 2014/0275940 A1 | 9/2014 | Hladio et al. |
| 2014/0276000 A1 | 9/2014 | Mullaney et al. |
| 2014/0276864 A1 | 9/2014 | Aghazadeh |
| 2014/0303631 A1 | 10/2014 | Thornberry |
| 2014/0330281 A1 | 11/2014 | Aghazadeh |
| 2014/0364858 A1 | 12/2014 | Li et al. |
| 2015/0018718 A1 | 1/2015 | Aghazadeh |
| 2015/0127009 A1 | 5/2015 | Berend et al. |
| 2015/0142372 A1 | 5/2015 | Singh |
| 2015/0143781 A1 | 5/2015 | Agnihotri |
| 2015/0150569 A1 | 6/2015 | van der Walt et al. |
| 2015/0164657 A1 | 6/2015 | Miles et al. |
| 2015/0238204 A1 | 8/2015 | Stone |
| 2015/0245914 A1 | 9/2015 | Langton |
| 2015/0313723 A1 | 11/2015 | Jansen |
| 2015/0342516 A1 | 12/2015 | Nguyen et al. |
| 2016/0038242 A1 | 2/2016 | Lo Iacono et al. |
| 2016/0175055 A1 | 6/2016 | Hook et al. |
| 2016/0206378 A1 | 7/2016 | Flett et al. |
| 2016/0213383 A1 | 7/2016 | van der Walt et al. |
| 2016/0220315 A1 | 8/2016 | Falardeau |
| 2016/0220318 A1 | 8/2016 | Falardeau et al. |
| 2016/0220385 A1 | 8/2016 | Falardeau et al. |
| 2016/0278943 A1 | 9/2016 | van der Walt et al. |
| 2016/0346044 A1 | 12/2016 | Brown et al. |
| 2017/0296203 A1 | 10/2017 | Stone |
| 2017/0296274 A1 | 10/2017 | van der Walt et al. |
| 2017/0325892 A1 | 11/2017 | Aghazadeh |
| 2018/0064496 A1 | 3/2018 | Hladio et al. |
| 2018/0177509 A1 | 6/2018 | Trabish et al. |
| 2018/0193171 A1 | 7/2018 | van der Walt et al. |
| 2018/0206860 A1 | 7/2018 | van der Walt et al. |
| 2018/0235762 A1 | 8/2018 | Radermacher et al. |
| 2019/0350728 A1 | 11/2019 | van der Walt et al. |
| 2020/0352654 A1 | 11/2020 | van der Walt et al. |
| 2020/0390501 A1 | 12/2020 | Brown et al. |
| 2021/0153880 A1 | 5/2021 | Nielsen et al. |
| 2021/0153908 A1 | 5/2021 | van der Walt et al. |
| 2021/0186711 A1 | 6/2021 | van der Walt et al. |
| 2021/0220152 A1 | 7/2021 | Nielsen et al. |
| 2021/0315716 A1 | 10/2021 | van der Walt et al. |
| 2022/0071509 A1 | 3/2022 | Borja et al. |
| 2022/0240953 A1 | 8/2022 | Stone |
| 2022/0313455 A1 | 10/2022 | van der Walt et al. |
| 2022/0378516 A1 | 12/2022 | Sierra et al. |
| 2023/0059247 A1 | 2/2023 | Gannoe |
| 2023/0149185 A1 | 5/2023 | Nielsen et al. |
| 2023/0157727 A1 | 5/2023 | van der Walt et al. |
| 2023/0248447 A1 | 8/2023 | van der Walt et al. |
| 2023/0277335 A1 | 9/2023 | van der Walt et al. |
| 2023/0301685 A1 | 9/2023 | van der Walt et al. |
| 2024/0099731 A1 | 3/2024 | Nielsen et al. |
| 2024/0099744 A1 | 3/2024 | van der Walt et al. |
| 2024/0197406 A1 | 6/2024 | van der Walt et al. |

FOREIGN PATENT DOCUMENTS

| | | |
|---|---|---|
| CA | 2 537 711 | 8/2007 |
| CN | 109846528 | 6/2019 |
| DE | 4 225 112 | 12/1993 |
| DE | 29704393 | 8/1997 |
| DE | 198 30 359 | 1/2000 |
| DE | 20116368 | 12/2001 |
| EP | 0 557 591 | 9/1993 |
| EP | 0 651 968 | 5/1995 |
| EP | 1 635 705 | 3/2006 |
| EP | 1 817 547 | 4/2012 |
| EP | 2 957 249 | 12/2015 |
| EP | 3 395 281 | 10/2018 |
| GB | 2 197 790 | 6/1988 |
| GB | 2 511 885 | 9/2014 |
| JP | 07-184929 | 7/1995 |
| JP | H08-240611 | 9/1996 |
| JP | 2004-237064 | 8/2004 |

(56) References Cited

FOREIGN PATENT DOCUMENTS

| | | |
|---|---|---|
| JP | 2006-314775 | 11/2006 |
| JP | 2006-528496 | 12/2006 |
| JP | 2007-503289 | 2/2007 |
| JP | 2007-534351 | 11/2007 |
| JP | 2008-521574 | 6/2008 |
| JP | 2008-537496 | 9/2008 |
| JP | 2009-511136 | 3/2009 |
| JP | 2011-502626 | 1/2011 |
| JP | 2013-000230 | 1/2013 |
| JP | 2014-524815 | 9/2014 |
| JP | 2015-524733 | 8/2015 |
| JP | 2015-226613 | 12/2015 |
| JP | 6980248 | 11/2021 |
| JP | 7180159 | 11/2022 |
| WO | WO 99/60939 | 12/1999 |
| WO | WO 2001/030247 | 5/2001 |
| WO | WO 02/000131 | 1/2002 |
| WO | WO 02/17798 | 3/2002 |
| WO | WO 2004/080323 | 9/2004 |
| WO | WO 2004/112610 | 12/2004 |
| WO | WO 2005/006993 | 1/2005 |
| WO | WO 2006/119387 | 11/2006 |
| WO | WO 2007/136784 | 11/2007 |
| WO | WO 2008/073999 | 6/2008 |
| WO | WO 2008/129414 | 10/2008 |
| WO | WO 2009/117833 | 10/2009 |
| WO | WO 2010/011978 | 1/2010 |
| WO | WO 2010/030809 | 3/2010 |
| WO | WO 2010/063117 | 6/2010 |
| WO | WO 2011/044273 | 4/2011 |
| WO | WO 2012/006172 | 1/2012 |
| WO | WO 2012/027815 | 3/2012 |
| WO | WO 2012/027816 | 3/2012 |
| WO | WO 2012/082164 | 6/2012 |
| WO | WO 2012/109361 | 8/2012 |
| WO | WO 2012/113054 | 8/2012 |
| WO | WO 2013/012561 | 1/2013 |
| WO | WO 2013/013094 | 1/2013 |
| WO | WO 2013/049534 | 4/2013 |
| WO | WO 2013/169674 | 11/2013 |
| WO | WO 2013/173700 | 11/2013 |
| WO | WO 2013/188960 | 12/2013 |
| WO | WO 2014/028227 | 2/2014 |
| WO | WO 2014/063181 | 5/2014 |
| WO | WO 2014/197988 | 12/2014 |
| WO | WO 2015/054745 | 4/2015 |
| WO | WO 2016/070288 | 5/2016 |
| WO | WO 2016/134168 | 8/2016 |
| WO | WO 2016/147153 | 9/2016 |
| WO | WO 2016/154489 | 9/2016 |
| WO | WO 2017/093769 | 6/2017 |
| WO | WO 2018/085900 | 5/2018 |
| WO | WO 2018/119360 | 6/2018 |
| WO | WO 2018/169980 | 9/2018 |
| WO | WO 2018/169995 | 9/2018 |
| WO | WO 2019/036752 | 2/2019 |
| WO | WO 2021/119001 | 6/2021 |
| WO | WO 2021/188798 | 9/2021 |
| WO | WO 2022/165561 | 8/2022 |

OTHER PUBLICATIONS 510 (k) Summary of Safety and Effectiveness for BrainLAB knee, in 5 pages.
Anderson Md., Kevin, et al., "Computer Assisted Navigation in Total Knee Arthroplasty", The Journal of Arthroplasty, 2005, vol. 20, No. 7, Suppl. 3, in 7 pages.
Ang, et al., An Active Hand-Held Instrument for Enhanced Microsurgical Accuracy, Medical Image Computing and Computer-Assisted Intervention, 2000, vol. 1935, pp. 878-887.
Arnold-Moore, et. al., Architecture of a Content Management Server for XML Document Applications, RMIT Multimedia Database Systems, Royal Melbourne Institute of Technology, Victoria Australia, in 12 pages.
ArthroCAD, Enhancing orthopedic outcomes through optimal alignment, 2012, Pages in 2 pages.
Bae et al., "Computer Assisted Navigation in Knee Arthroplasty", Clinics in Orthopedic Surgery, 2011, vol. 3, pp. 259-267.
Bargren, Md., et al.,, Alignment in Total Knee Arthroplasty, Correlated Biomechanical and Clinical Observations, Clinical Orthopaedics and Related Research, Mar. 1, 1983, Issue 173, pp. 178-183, Philadelphia.
Bathis, H. et al., "Alignment in total knee arthroplasty", The Journal of Bone & Joint Surgery (Br), 2004, 86-B, pp. 682-687, British Editorial.
Bhandari, Design and Prototype of a Computer Assisted Surgical Navigation System for Total Knee Replacement Surgery, May 12, 2009, Pages in 294 pages.
Biomet Orthopedics, Inc, Vision Acetabular Surgical Techniques, website brochure, pp. 16 pages.
Biomet Orthopedics, Inc., Universal Ringlock® Acetabular Series, vol. website brochure, pp. 13 pages.
Brainlab, "Position Determination and Calibration in optical tracking systems", Florenus the technology merchants, in 2 pages.
Brainlab, "Tracking and imaging in Navigation", Florenus, in 2 pages.
Brennan, et al., Quantification of Inertial Sensor-Based 3D Joint Angle Measurement Accuracy Using and Instrumented Gimbal, Gait & Posture, May 23, 2011, vol. 34, pp. 320-323.
Chauhan, et al., Computer-Assisted Knee Arthroplasty Versus a Conventional Jig-Based Technique, The Journal of Bone & Joint Surgery, 2004, vol. 86-B, pp. 372-377.
Cutti, et al., Motion Analysis of the Upper-Limb Based on Inertial Sensors: Part 1—Protocol Description, Journal of Biomechanics, Jan. 1, 2007, vol. 40, pp. S250.
Decking, Md., et al., Leg Axis After Computer-Navigated Total Knee Arthroplasty, The Journal of Arthroplasty, 2005, vol. 20, Issue 3, pp. 282-288.
Depuy, Johnson & Johnson, Co.,, Summit Cemented Hip System, website brochure, pp. 21 pages.
De Momi, et al., "In-vitro experimental assessment of a new robust algorithm for hip joint centre estimation", Journal of Biomechanics, Feb. 26, 2009, vol. 42, pp. 989-995.
Digioia III, Md., et al., "Comparison of a Mechanical Acetabular Alignment Guide with Computer Placement of the Socket", The Journal of Arthroplasty, Apr. 2002, vol. 17, No. 3, in 6 pages.
Eric Foxlin, Chapter 7. Motion Tracking Requirements and Technologies, Handbook of Virtual Environment Technology, 2002, vol. Kay Stanney, Ed., Issue Lawrence Erlbaum Ass.
Favre, et al., 3D Evaluation of the Knee Joint Using Ambulatory System: Application to ACL-Deficient Knees, Journal of Biomechanics, Jan. 1, 2007, vol. 40, pp. S251.
Favre, et al., A New Ambulatory System for Comparative Evaluation of the Three-Dimensional Knee Kinematics, Applied to Anterior Cruciate Ligament Injuries, Knee Surgery, Sports Traumatology, Arthroscopy, Jan. 19, 2006, vol. 14, pp. 592-604.
Favre, et al., Ambulatory Measurement of 3D Knee Joint Angle, Journal of Biomechanics, Jan. 28, 2008, vol. 41, Issue 1029-1035.
Fixed Reference Surgical Technique, Sigma High Performance Instruments, DePuy Orthopaedics, Inc., 2008, Warsaw, IN, in 52pages.
Ganapathi et al., "Limb Length and Femoral Offset Reconstruction During THA Using CT-Free Computer Navigation", The Journal of Bone and Joint Surgery, 2009, vol. 91-B, Supplement III, p. 399.
Goniometer, AllHeart.com, 2004, website: http://allheart.com/allheart, (1 page).
Haaker et al., "Computer-Assisted Navigation Increases Precision of Component Placement in Total Knee Arthroplasty", Clinical Orthopaedics and Related Research, Apr. 2005, vol. 433, pp. 152-159.
Hofstetter, Ph.D., et al., "Computer-Assisted Fluoroscopy-Based Reduction of Femoral Fractures and Antetorsion Correction", Computer Aided Surgery, 2000, vol. 5, pp. 311-325, Wiley-Liss, Inc.
Hsieh, Pang-Hsin, et al., "Image-guided periacetabular osteotomy: computer-assisted navigation compared with the conventional technique: A randomized study of 36 patients followed for 2 years", Acta Orthopaedica, Aug. 1, 2006, 77:4, pp. 591-597.
IASSIST Knee, Surgical Technique, Zimmer, Inc., 2012.

(56) References Cited

OTHER PUBLICATIONS

International Preliminary Report for Application No. PCT/US2004/018244, dated Dec. 13, 2005, in 11 pages.
International Search Report and Written Opinion issued in PCT Application No. PCT/US2013/039770, dated Sep. 25, 2013.
International Preliminary Report on Patentability issued in PCT Application No. PCT/US2013/039770, dated Nov. 11, 2014.
International Search Report and Written Opinion issued in PCT Application No. PCT/US2013/041556, dated Sep. 13, 2013.
International Preliminary Report on Patentability issued in PCT Application No. PCT/US2013/041556, dated Nov. 18, 2014.
International Search Report and Written Opinion issued in PCT Application No. PCT/US2013/053182, dated Nov. 11, 2013.
International Search Report for Application No. PCT/US2004/018244, dated Feb. 15, 2005, in 4 pages.
International Search Report for International Application No. PCT/US2009/051769 dated Nov. 19, 2009, in 11 pages.
International Search Report for International Application No. PCT/US2009/051769 dated Nov. 19, 2009, in 3 pages.
International Search Report for International Application No. PCT/US2011/022162, dated Jun. 16, 2011, in 4 pages.
International Search Report for International Application No. PCT/US2009/056553, dated Nov. 4, 2009, in 12 pages.
International Preliminary Report on Patentability issued in PCT Application No. PCT/US2013/053182, dated Feb. 17, 2015, in 10 pages.
International Search Report and Written Opinion issued in International Application No. PCT/US2016/018508, dated Jun. 22, 2016, in 19 pages.
Jenny, et al., Computer-Assisted Implantation of Total Knee Prosthesis: A Case-Control Comparative Study with Classical Instrumentation, Computer Aided Surgery, 2001, vol. 6, pp. 217-220.
Konyves et al., "The importance of leg length discrepancy after total hip arthroplasty", The Journal of Bone & Joint Surgery (Br), Feb. 2005, vol. 87-B, No. 2, pp. 155-157.
Leenders, Md., et al., "Reduction in Variability of Acetabular Cup Abduction Using Computer Assisted Surgery: A Prospective and Randomized Study", Computer Aided Surgery, 2002, vol. 7, pp. 99-106.
Leung, et al., Intraobserver Errors in Obtaining Visually Selected Anatomic Landmarks During Registration Process in Nonimage-based Navigation-assisted Total Knee Arthroplasty, The Journal of Arthroplasty, 2005, vol. 20, Issue 5, pp. 591-601.
Liebergall, Meir, et al., "Computerized Navigation for the Internal Fixation of Femoral Neck Fractures", The Journal of Bone & Joint Surgery Am, 2006, vol. 88, pp. 1748-1754.
Longo, et al., MIKA Surgical Technique, DJO Surgical, 2008, Austin Texas in 14 pages.
Luinge, Inertial Sensing of Human Movement, Twente University Press, Feb. 15, 1973, Pages in 88 pages.
Mackenzie, et al., A Two-Ball Mouse Affords Three Degrees of Freedom, Extended Abstracts of the CHI '97 Conference on Human Factors in Compounding Systems (as printed from the internet on Jun. 13, 2012 URL: http://www.yorku.ca/mack/CHI97a.htm), 1997, pp. 303-304.
Medical Research Ltd, Clinical Goniometer, http://www.mie-uk.com/Gonio, 1997, pp. 1 page.
Minimally Invasive TKA Genesis II Anterior Cut First, Surgical Technique, Smith & Nephew, Nov. 2003, Memphis TN, in 16 pages.
Noble et al., "Computer Simulation: How Can it Help the Surgeon Optimize Implant Position?", Clinical Orthopaedics and Related Research, Dec. 2003, vol. 417, pp. 242-252.
Parratte, Sebastien, et al., "Validation and Usefulness of a Computer-Assisted Cup-Positioning System in Total Hip Arthroplasty. A Prospective, Randomized, Controlled Study", The Journal of Bone & Joint Surgery Am, 2007, vol. 89, pp. 494-499.
Perseus Intelligent Cutting Guide, Orthokey, Product Guide, in 8 pages.
Perseus Intelligent Cutting Guide, Smart Instruments for Knee Arthroplasty, Orthokey, in 2 pages.

Ritter, M.D., et al., Postoperative Alignment of Total Knee Replacement, Its Effect on Survival, Clinical Orthopaedics and Related Research, Feb. 1, 1994, Issue 299, pp. 153-156, Philadelphia.
Rocon, et al., Application of Inertial Sensors and Rehabilitation Robotics, Rehabilitation Robotics 2007, Jun. 1, 2007, pp. 145-150.
Sacks-Davis et. al., Atlas: A nested Relational Database System for Text Applications, IEEE Transations on Knowledge and Data Engineering, v.7, n.3, Jun. 1995, pp. 454-470.
Schep, et al., "Computer assisted orthopaedic and trauma surgery State of the art and future perspectives", Injury Int. J. Care Injured 34, (website: www.elsevier.com/locate/injury), 2003 pp. 299-306.
Scott, M.S., et al., P.F.C. Sigma Knee System, Primary Surgical Technique Part 1 of 2, DePuy International Ltd., 2003, England, (up to p. 44), in 48 pages.
Scott, M.S., et al., P.F.C. Sigma Knee System, Primary Surgical Technique Part 2 of 2, DePuy International Ltd., 2003, England, Part A (up to p. 74), in 31 pages. (This reference was split in two due to size exceeding over 25MB).
Scott, M.S., et al., P.F.C. Sigma Knee System, Primary Surgical Technique Part 2 of 2, DePuy International Ltd., 2003, England, Part B (up to p. 104), in 31 pages. (This reference was split in two due to size exceeding over 25MB).
Sikorski et al., "Computer-Assisted Orthopaedic Surgery: Do We Need CAOS?", The Journal of Bone & Joint Surgery (Br), Apr. 2003, vol. 85-B, No. 3, pp. 319-323.
Slomczykowski, et al., "Novel Computer-Assisted Fluoroscopy System for Intraoperative Guidance: Feasibility Study for Distal Locking of Femoral Nails", Journal of Orthopaedic Trauma, 2001, vol. 15, No. 2, pp. 122-131, Lippincott Williams & Wilkins, Inc., Philadelphia.
Stulberg, et al., Computer-Assisted Total Knee Replacement Arthroplasty, Operative Techniques in Orthopaedics, Jan. 2000, vol. 10, Issue 1, pp. 25-39.
The Academy of Orthopaedic Surgeons, Academy News, http://www.aaos.org/wordhtml/2001news/b6-01.htm, Mar. 1, 2001, pp. 1 page.
Tilt Sensors: High Accuracy, Digital Series, Crossbow Technology, Inc., pp. 32-35.
Upadhyay et al., "Medical Malpractice in Hip and Knee Arthroplasty", The Journal of Arthroplasty, 2007, vol. 22, No. 6, Suppl. 2, pp. 2-7.
Visser, et al., 3D Analysis of Upper Body Movements in Bilateral Amputee Gait Using Inertial Sensors, Journal of Biomechanics, Jan. 1, 2007, vol. 40, Issue S509.
Wentzensen et al., "Image-based hip navigation", International Orthopaedics (SICOT), 2003, vol. 27 (Suppl. 1), pp. S43-S46.
Wolfstadt et al., "An intelligent instrument for improved leg length and hip offset accuracy in total hip arthroplasty", Abstract Only.
Written Opinion for International Application No. PCT/US2009/051769, dated Nov. 19, 2009, in 7 pages.
Written Opinion for International Application No. PCT/US2011/022162, dated Jun. 16, 2011, in 9 pages.
Written Opinion of the ISR for Application No. PCT/US2004/018244, in 10 pages.
Wylde et al., "Prevalence and functional impact of patient-perceived leg length discrepancy after hip replacement", International Orthopaedics, 2009, vol. 33, pp. 905-909.
Wylde et al., "Patient-perceived leg length discrepancy after total hip replacement: prevalence and impact on functional outcome", International Orthopaedics, 2008, vol. 24, No. 2, pp. 210-216.
Zheng et al., "Technical Principles of Computer Assisted Orthopaedic Surgery", Suomen Ortopedia ja Traumatologia, Feb. 2008, vol. 31, pp. 135-147.
Zhou, et al., Use of Multiple Wearable Inertial Sensors in Upper Limb Motion Tracking, Medical Engineering & Physics, Jan. 1, 2008, vol. 30, pp. 123-133.
Zimmer NexGen Flexion Balancing Instruments, Surgical Technique, 2007, www.zimmer.com, in 44 pages.
Zorman, David, et al., "Computer-assisted total knee arthroplasty: comparative results in a preliminary series of 72 cases", ActaOrthop. Belg., 2005, 71, pp. 696-702.

(56) References Cited

OTHER PUBLICATIONS

Shah et al., "Is the pelvis stable during supine total hip arthroplasty?", Acta Orthop Belg., Mar. 1, 2017, vol. 83, No. 1, pp. 81-86.

* cited by examiner

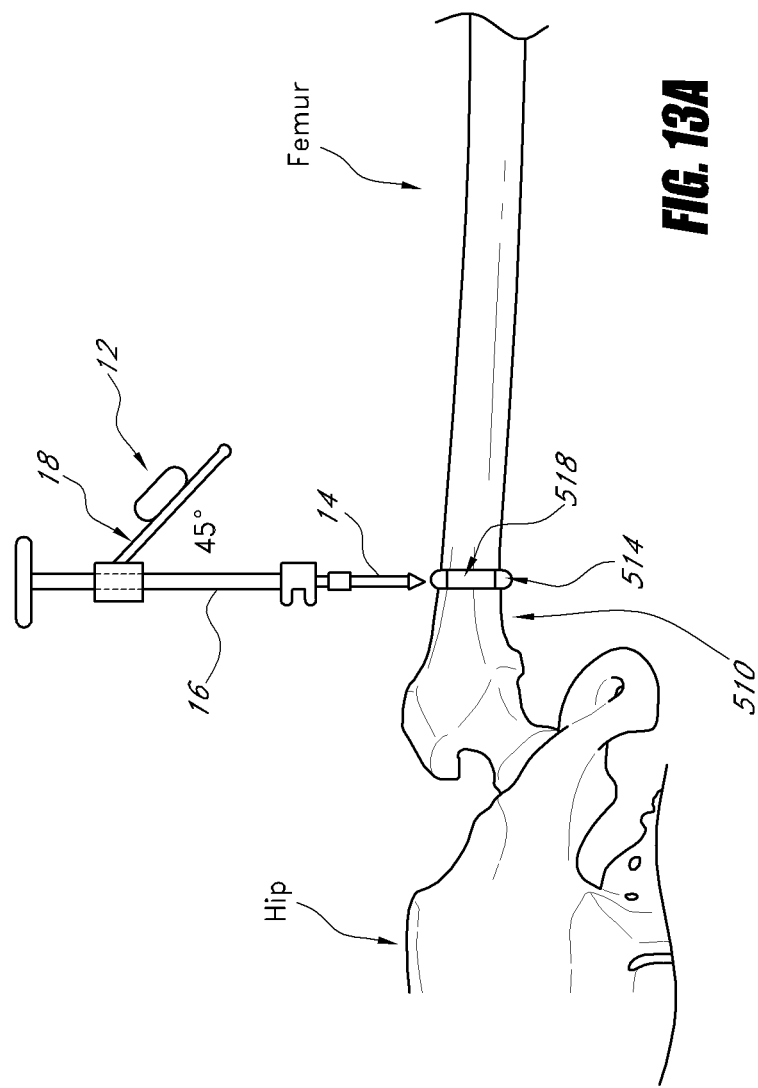

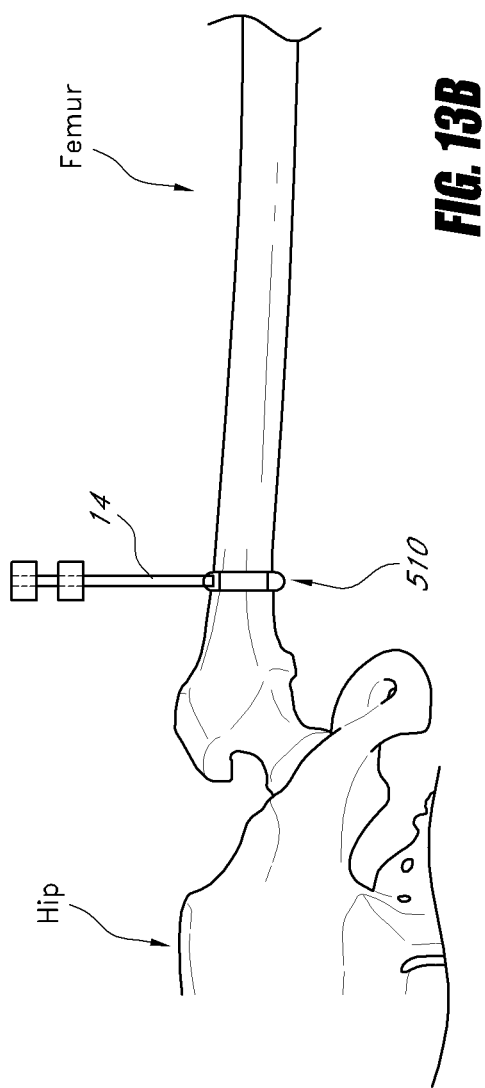

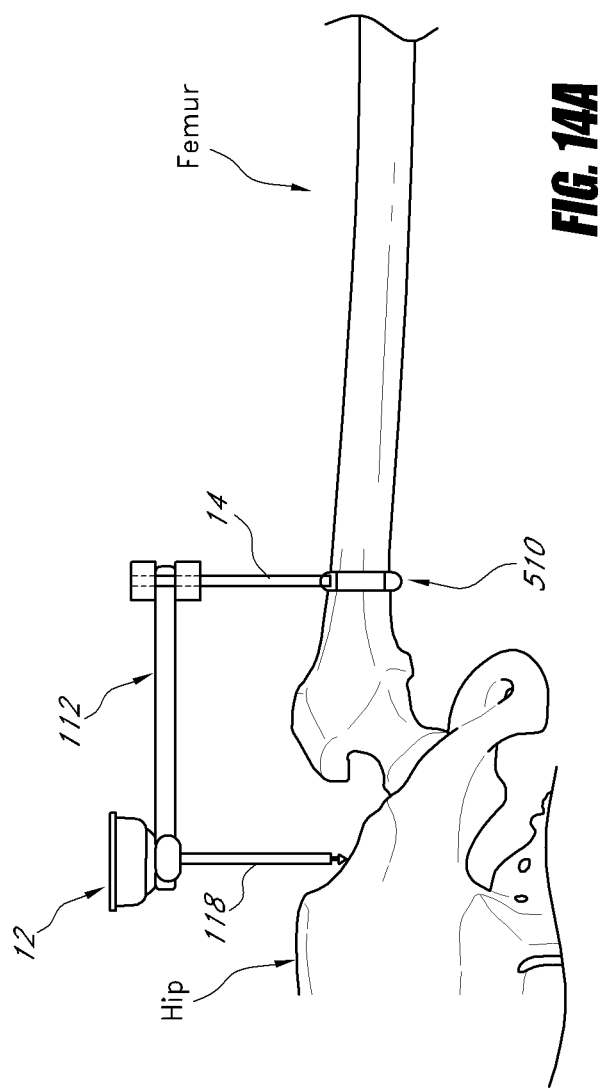

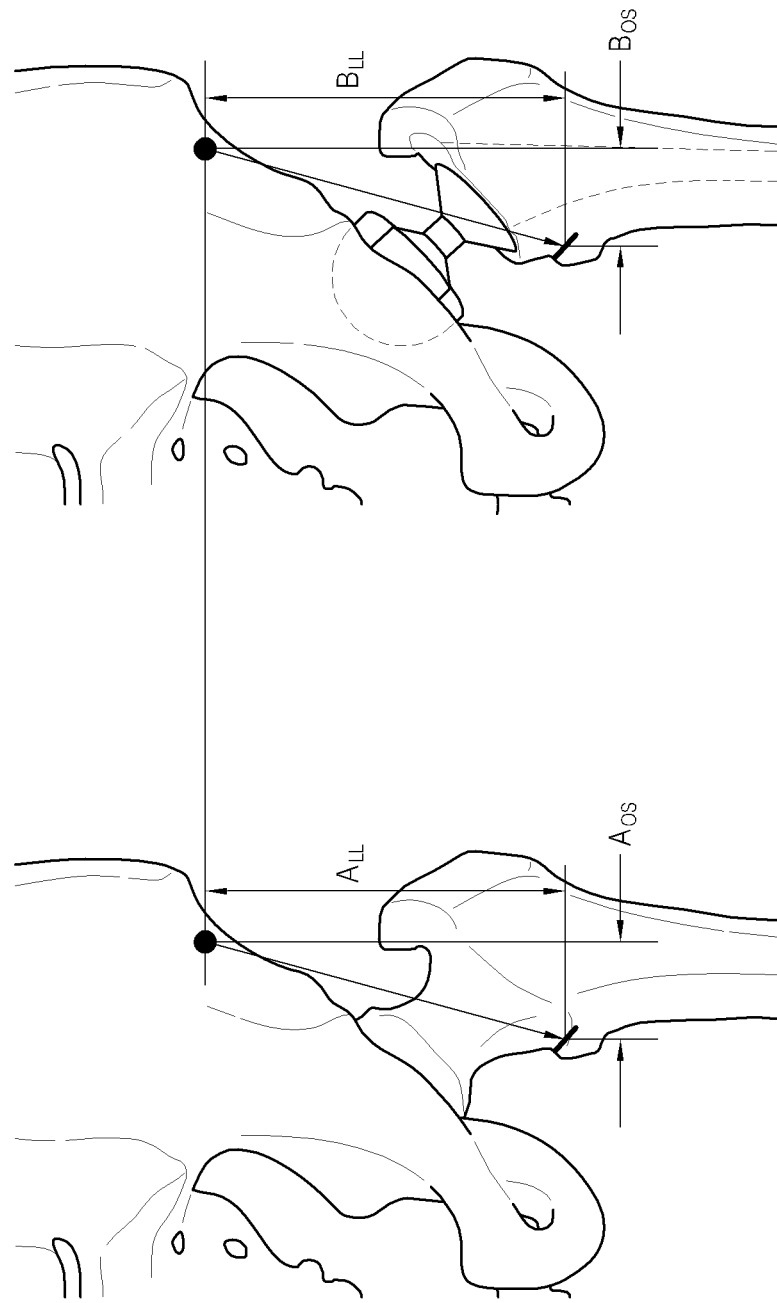

HIP SURGERY SYSTEMS AND METHODS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present application is directed to systems and methods for joint replacement, in particular to systems and methods for hip joint replacement which utilize a surgical orientation device or devices.

Description of the Related Art

Joint replacement procedures, including hip joint replacement procedures, are commonly used to replace a patient's joint with a prosthetic joint component or components. Specifically, the hip joint often requires replacement in the form of prosthetic components due to strain, stress, wear, deformation, misalignment, and/or other conditions in the joint. Prosthetic hip joint components can be designed to replace, for example, an acetabular prosthetic socket in the hip and/or a femoral head.

Current systems and methods often use expensive, complex, bulky, and/or massive computer navigation systems which require a computer or computers, as well as three dimensional imaging, to track a spatial location and/or movement of a surgical instrument or landmark in the human body. These systems are used generally to assist a user to determine where in space a tool or landmark is located, and often require extensive training, cost, and room.

Where such complex and costly systems are not used, simple methods are used, such as "eyeballing" the alignment of a prosthetic acetabular cup or femoral broach. These simple methods are not sufficiently accurate to reliably align and place implant components and the bones to which such components are attached.

Correct positioning of surgical instruments and implants, as used in a surgical procedure with respect to the patient's anatomy, is therefore often an important factor in achieving a successful outcome. In certain orthopedic implant procedures, such as total hip replacement (THR) or arthroplasty, total knee arthroplasty (TKA), high tibial osteotomy (HTO), and total shoulder replacement (TSR), for example, the optimal orientation of the surgical implant can enhance initial function and long term operability of the implant. A misaligned acetabular prosthetic cup can lead to complications such as dislocation of the hip joint, decreased joint motion, joint pain, and hastened failure of the implant.

SUMMARY OF THE INVENTIONS

Accordingly, there is a lack of devices, systems and methods that can be used to accurately position components of prosthetic joints without overly complicating the procedures, crowding the medical personnel, and/or burdening the physician or health-care facility with the great cost of complex navigation systems. Thus, there is a need in the art for improved systems and methods for obtaining accurate orientation of surgical instruments and implants during various orthopedic repair and replacement procedures, including total hip replacement ("THR"). Furthermore, there is a need for such devices and methods to be simple and easy to operate.

In accordance with at least one embodiment, an apparatus for preparing a hip joint can comprise a reference post having a distal end adapted to be driven into a portion of a pelvic bone, a proximal end, and a reference post body extending along a longitudinal axis between the proximal and distal ends, a coupling device disposed adjacent to the proximal end of the reference post adapted for connecting the reference post body to a second surgical component, and an orientation sensor coupled with the reference post.

In accordance with another embodiment, an apparatus for preparing a hip joint can comprise a mounting structure having a first end adapted to secure to a patient's anatomy and a second end disposed away from the first end, an elongate member having a first end and a second end, the first end of the elongate member adapted to connect to the second end of the mounting structure, a marking device coupled with the second end of the elongate member for visually indicating the position of an anatomical landmark during a procedure, and a surgical orientation device coupled with the elongate member for movement therealong for measuring at least one of position and orientation along the elongate member.

In accordance with another embodiment, an apparatus for assessing the orientation of an acetabular landmark or an acetabular implant can comprise a handling device comprising a proximal end with a handle, a distal end, and an elongate member extending therebetween, an acetabular landmark contacting device coupled with the distal end of the handling device, and a surgical orientation device for detecting and recording an orientation of the acetabular landmark or the acetabular implant.

In accordance with another embodiment, an acetabular surface preparation apparatus can comprise a handling device comprising a proximal end with a handle, a distal end, and a rotatable shaft extending therebetween, a surface preparation device coupled with the distal end and adapted to remove bone from the acetabulum to create a surface suitable for receiving an acetabular implant, a sleeve disposed around the rotatable shaft and adapted to remain stationary while the shaft is rotating, and a surgical orientation device coupled with the sleeve such that the orientation device can remain stationary while the rotatable shaft is rotated.

In accordance with another embodiment, an acetabular implant placement device can comprise a handling device comprising a proximal end with a handle, a distal end, and an elongate member extending therebetween, wherein the distal end comprises an implant contacting structure adapted to couple with an acetabular implant, and a surgical orientation device coupled with the handling device such that the orientation of at least one of the handling device and the surgical orientation device can be monitored as the acetabular implant is advanced into the acetabulum.

In accordance with another embodiment, a method for preparing a patient's hip for receiving an implant can comprise providing a first orthopedic system comprising a reference post comprising an orientation sensor, an impactor coupled with the reference post, a first angle assessment guide, and a portable surgical orientation device attached to the angle assessment guide, attaching the reference post to a hip bone of the patient, measuring and recording a reference distance from the reference post to an anatomical landmark using the portable surgical orientation device, removing the angle assessment guide, impactor, and portable surgical orientation device from the reference post, providing a second orthopedic system comprising an alignment guide, a second angle assessment guide attached to the alignment guide, and the portable surgical orientation device attached to the alignment guide, measuring an orientation of an anatomical plane using the second angle assessment guide, orienting an implant relative to the anatomical plane and inserting the implant into the acetabulum using the second orthopedic system, attaching a femoral broach to the patient's femur, the femoral broach including a head, positioning the head in the implant, providing the first orthopedic system a second time, and measuring changes in the reference distance.

In accordance with another embodiment, a method for preparing a patient's hip for receiving an implant can comprise attaching a first orthopedic system to the patient's hip with a reference device, the first orthopedic system comprising a portable surgical orientation device, measuring and recording a reference distance from the reference device to an anatomical landmark using the portable surgical orientation device, measuring an orientation of an anatomical plane on the patient's hip using a second orthopedic system, the second orthopedic system comprising the portable surgical orientation device, orienting an implant relative to the anatomical plane using the second orthopedic system, inserting the implant into the acetabulum, inserting a prosthetic femoral head into the implant, and measuring changes in the reference distance using the first orthopedic system.

In accordance with another embodiment, a method for positioning a patient in a hip procedure can comprise advancing a reference device into a patient's pelvic bone, coupling a surgical orientation device with the reference device such that the orientation device is not moveable relative to the pelvic bone, measuring at least one of the position or orientation of at least a portion of the patient's hip joint using the surgical orientation device, and moving the patient's hip joint to selected position the patient relative to a fixed reference frame based on the measurement on the surgical orientation device.

In accordance with another embodiment, a method for assessing relative position of portions of a hip joint can comprise coupling a surgical orientation device to a first bone of a patient's hip at a first location with a reference device, measuring a reference distance from the reference device to an anatomical landmark of a second bone using the surgical orientation device, performing a hip procedure, and after performing the hip procedure, confirming the position of the anatomical landmark relative to the first location.

In accordance with another embodiment, a method of placing an acetabular implant can comprise providing an orientation apparatus comprising an elongate member having a handle disposed at a proximal end, an angle assessment device disposed at a distal end, and a surgical orientation device, advancing the angle assessment device into contact with an anatomical landmark of the acetabulum while measuring orientation of the landmark, preparing the acetabulum for receiving the acetabular implant, placing the acetabular implant within the acetabulum, and advancing the angle assessment device into contact with the acetabular implant to confirm the orientation of the implant.

In accordance with another embodiment, a method of preparing an acetabular surface for receiving an acetabular implant can comprise providing a handle, a shaft rotatably coupled with the handle, a reamer coupled a distal end of the shaft, and an orientation device coupled in a fixed position relative to the handle, providing contact between the reamer and an acetabular surface while rotating the shaft and reamer to remove bone within the acetabulum, and measuring the orientation of the reamer while providing contact between the reamer and an acetabular surface.

BRIEF DESCRIPTION OF THE DRAWINGS

FIG. 13A illustrates a method in which the patient's hip is generally parallel to an operating table and a fixture is provided for coupling a reference post of the orthopedic system of FIGS. 2A-C with the patient's anatomy;

FIG. 13B illustrates a technique for coupling a reference post with the fixture shown in FIG. 13A;

FIG. 14A illustrates a method in which the orthopedic system of FIGS. 3A-B is used to measure a distance between the fixed reference post and a reference location on the patient's anatomy;

FIGS. 29A and B are schematic illustrations of a change in leg length (LL) and leg offset (OS) as measured prior to and after a hip preparation procedure according to one embodiment.

DETAILED DESCRIPTION OF THE PREFERRED EMBODIMENT

Although certain preferred embodiments and examples are disclosed below, it will be understood by those skilled in the art that the inventive subject matter extends beyond the specifically disclosed embodiments to other alternative embodiments and/or uses of the inventions, and to obvious modifications and equivalents thereof. Thus it is intended that the scope of the inventions herein disclosed should not be limited by the particular disclosed embodiments described below. Thus, for example, in any method or process disclosed herein, the acts or operations making up the method/process may be performed in any suitable sequence, and are not necessarily limited to any particular disclosed sequence. For purposes of contrasting various embodiments with the prior art, certain aspects and advantages of these embodiments are described where appropriate herein. Of course, it is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

I. Overview of Systems and Methods

The following sections describe in detail systems and methods for a hip replacement procedure. The orthopedic systems described herein include orthopedic systems and orthopedic devices for preparing the hip to receive prosthetic components. The systems include but are not limited to orthopedic systems 10, 110, 210, 310, and 410 described herein, each of which can be used during various stages of an orthopedic procedure or procedures, such as for example a total hip replacement procedure. These orthopedic systems and devices can be used to perform minimally invasive, cost-efficient, successful orthopedic procedures.

II. Orthopedic Systems

A number of different orthopedic systems are discussed below. These systems are useful, for example, for modifying the natural hip joint to enable the hip joint to have a prosthetic component or components, such components including but not limited to a prosthetic acetabular cup.

Figure 1:
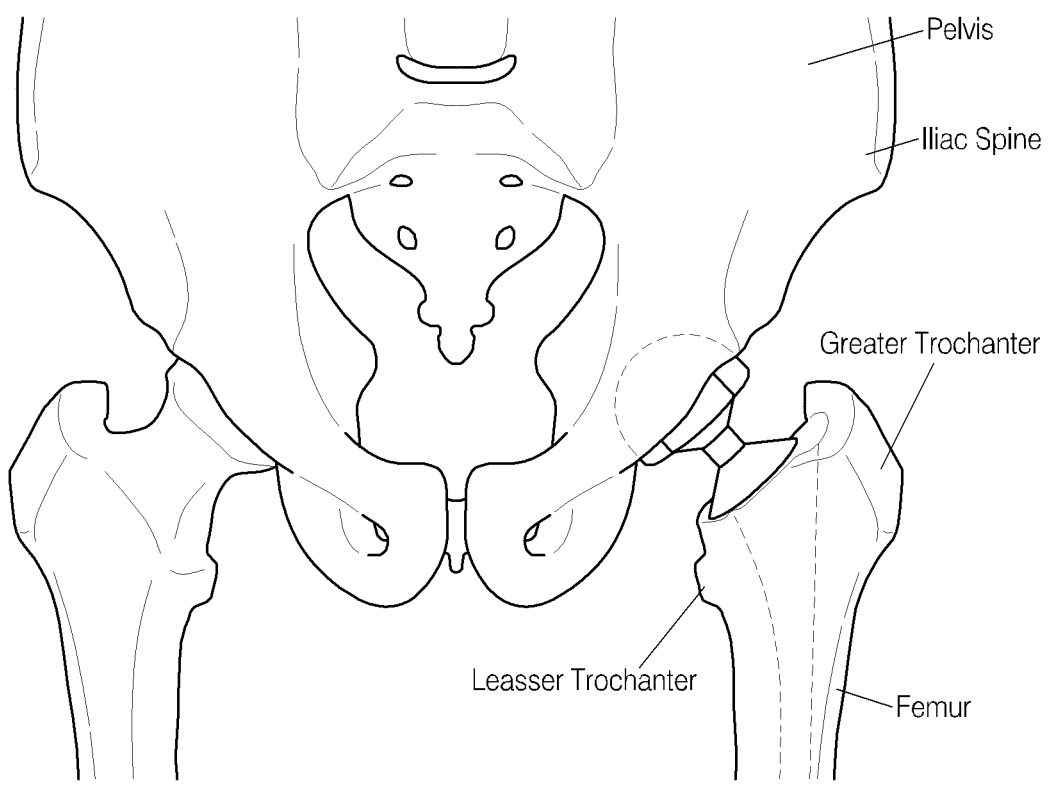
FIG. 1 shows a representation of a human anatomy, identifying generally the femur, pelvis, iliac spine, and lesser trochanter.

FIG. 1 illustrates a pelvis, femur, iliac spine, and lesser and greater trochanter regions. As will be described further herein, these and/or other anatomical locations and landmarks can be referenced and used throughout an orthopedic procedure or procedures in conjunction with the systems described herein.

Figure 2A:
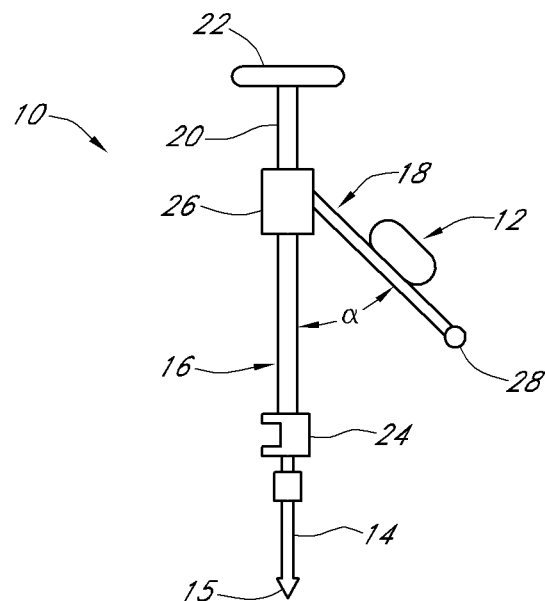
FIG. 2A is a side view of a orthopedic system according to one embodiment for establishing a reference location on a patient's anatomy.

A. Orthopedic System for Establishing a Reference Location on the Patient's Anatomy With reference to FIGS. 2A-D, an orthopedic system 10 can be used to provide a fixed reference on a patient's anatomy, as well as to provide an anchor and/or support for other orthopedic systems. As illustrated in FIG. 2A, the orthopedic system 10 can comprise a surgical orientation device 12, reference device 14, impactor 16, and angle assessment guide 18.

1. Device for Use as a Reference in the Patient's Anatomy

The system 10 can comprise a device or component that serves as a reference for other systems or devices. For example, and as illustrated in FIG. 2A, the reference device 14 can comprise a reference post 14, and can serve as a reference for other systems or devices. The reference post 14 can comprise a thin, metallic pin that can be at least partially driven (e.g. hammered with a slap hammer) into a bony area on the patient's anatomy. As will be described further herein, the reference post 14 can be partially driven, for example, into the iliac spine on a patient's pelvis. Other types of reference posts can also be used. The reference post 14 can also be used to hold back tissue that would otherwise cover the surgical field, e.g., skin and muscle and other sub-dermal tissues. In a preferred arrangement, the reference post 14 also can serve as an anchor or otherwise mechanically support other joint preparation systems, as discussed below. The reference post 14 can comprise a mounting structure. For example, the reference post 14 can support the system 310 in one technique. The reference post 14 also can be coupled with an orientation sensor or sensors 15, which can be disposed on the reference post's surface or inside the reference post 14. The sensor or sensors 15 can detect orientation (e.g. position) and/or relative movement of the reference post 14. By detecting movement of the sensor(s) 15, movement of anatomy with which the reference post is coupled (e.g. surrounding bony area) can also be detected.

In one technique, the impactor 16 is used to assist in placement of the reference post 14. With continued reference to FIGS. 2A-C, the impactor 16 can be releasably coupled to the reference post 14. The impactor 16 can drive the reference post 14 into a bony area on the patient's anatomy, and the impactor 16 can then be removed. The impactor 16 can include, for example, an elongate rod 20 with one end 22 for pounding or striking with a hammer, and an opposite end 24 for releasably connecting to the impactor 14.

Figure 2B:
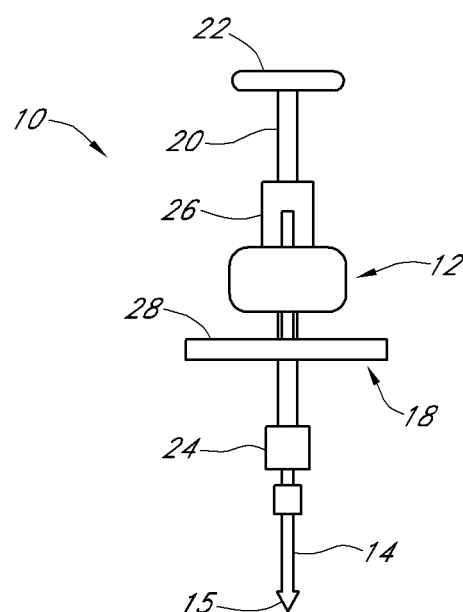
FIG. 2B is a front view of the orthopedic system of FIG. 2A.
Figure 2C:
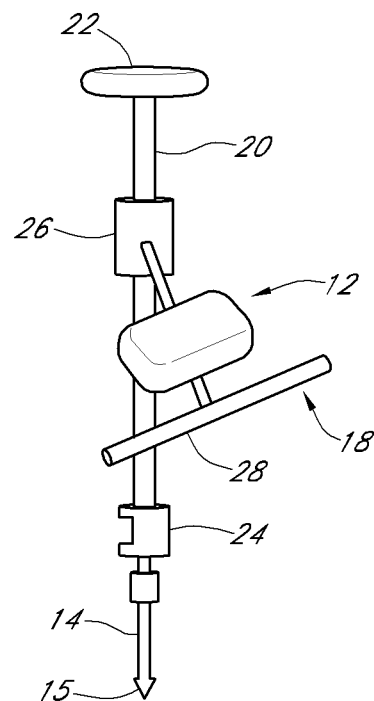
FIG. 2C is a perspective view of the orthopedic system of FIG. 2A.
Figure 2D:
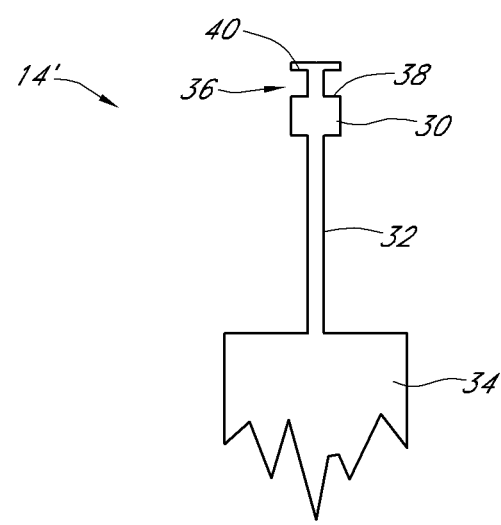
FIG. 2D is a front view of a reference post according to one embodiment.

FIG. 2D shows another embodiment of a reference post 14' which can be used with system 10. The reference post 14' can comprise a proximal portion 30, an elongate body 32, and a distal portion 34. The proximal portion 30 can comprise a coupling structure comprising an annular recess 36 defined between a proximally facing shoulder 38 and a distally facing shoulder 40. Other coupling structures are also possible. As described above, the impactor 16 can comprise a coupling structure 24 for releasable attachment to the reference post 14'. In some embodiments, the end 24 of impactor 16 can comprise be fork-shaped as shown in FIG. 2C, and adapted to be received within the annular recess 36 of the reference post 14. The fork-shaped structure 24 can abut at least one of the proximal end 30 of the reference post 14 and the proximally facing shoulder 38 to transfer a force to the body 32 of the reference post 14 and drive distal end 34 into the bone. Thus, the impactor 16 can enable the force of blows of the hammer to be transferred to the reference post 14 such that the distal end 34 of reference post 14 can be advanced into the bone.

2. Device for Angle Assessment Relative to Operating Table

The system 10 can further comprise a device which can be used to orient the patient's pelvis relative to the operating table. For example, and as described further herein, the angle assessment guide 18 can be used to orient the patient's pelvis. The angle assessment guide 18 can comprise a member 19, an attachment structures 26, and an end member 28. The attachment structure 26 can couple (e.g. attach, releasably attach) the angle assessment guide 18 to the impactor 16 and/or reference post 14 at a certain angle "a". The angle "a" can be any of a number of angles, and preferably 45 degrees. FIG. 2A shows "a" at an angle of approximately 45 degrees. The angle assessment guide 18 can comprise any of a number of sizes and shapes. For example, the angle assessment guide can comprise a first elongate member, a second elongate member, and a third elongate member. The first elongate member can couple with the proximate end of the reference post 14, 14', and can comprise the elongate rod 20 of the impactor. The second elongate member can couple with the first elongate member at an angle relative to the first elongate member (e.g. an acute angle), and can comprise member 19. The third elongate member can be mounted to the second elongate member, and can comprise the cross-bar-shaped member 28 as illustrated in FIG. 2A. The surgical orientation device 12 can be releasably coupled to the angle assessment guide 18, such that movement of the angle assessment guide 18 causes identical movement of the surgical orientation device 12. The surgical orientation device can alternatively or additionally be releasably coupled to the reference post 14. In some embodiments, the surgical orientation device can be coupled to the cross-bar member 28 with a coupling device such as that disclosed in U.S. patent application Ser. No. 12/509,388, filed Jul. 24, 2009, the contents of which are incorporated in their entirety by reference herein.

3. Surgical Orientation Device

With continued reference to FIGS. 2A-C, the surgical orientation device 12 can be can be used for verifying an alignment and/or measuring distances. "Surgical orientation device" is a broad term as used herein, and includes, without limitation, devices which can be used alone or in conjunction with an orthopedic device or devices to identify or track a relative position of one or more orthopedic devices or anatomical structures, and can encompass any of the embodiments shown in the drawings and as described herein, as well as any of the embodiments shown or described in U.S. patent application Ser. No. 12/509,388, filed Jul. 24, 2009, the contents of which are incorporated in their entirety by reference herein.

Figure 7:
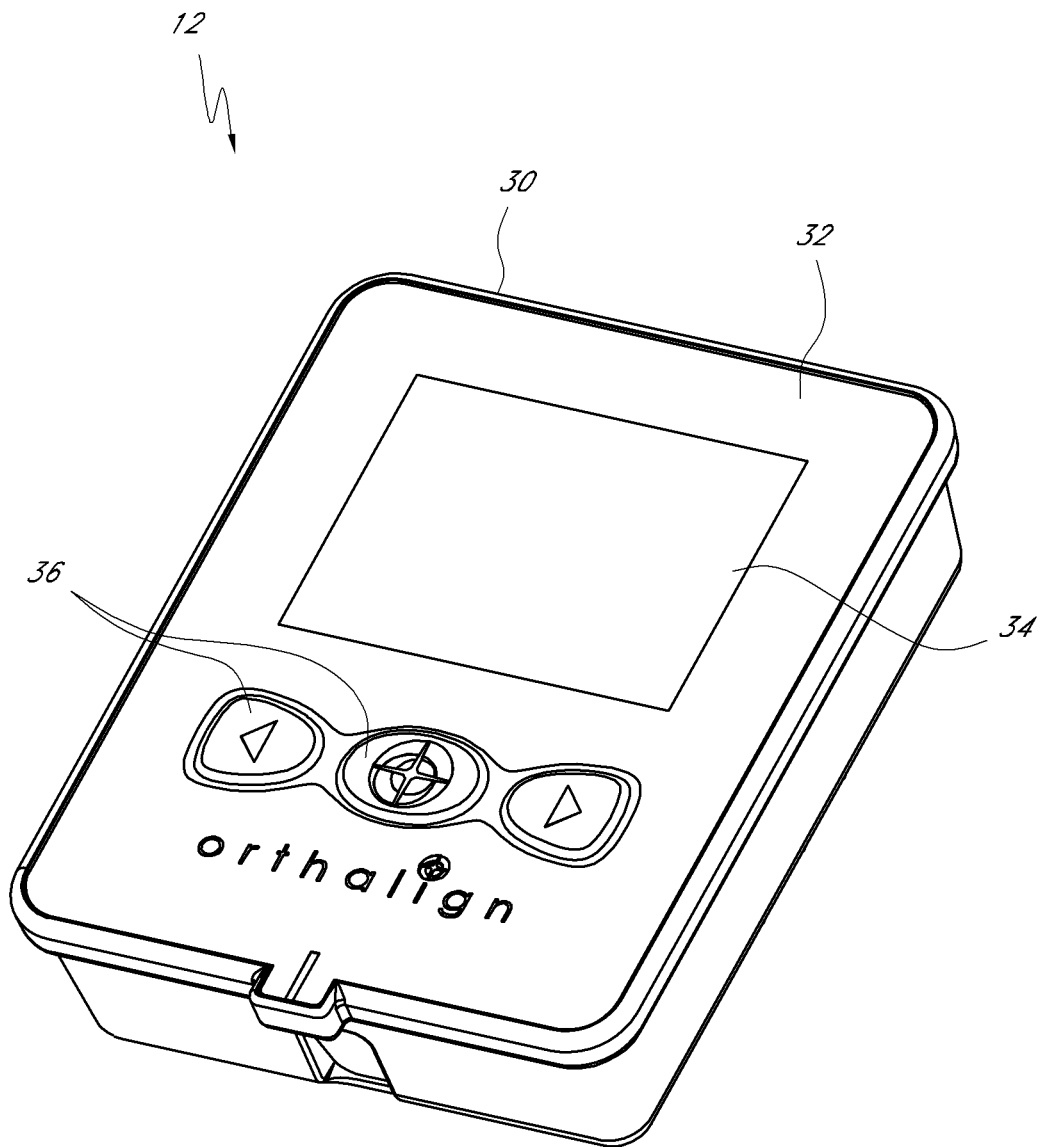
FIG. 7 is a perspective view of a surgical orientation device according to one embodiment that can be used in conjunction with one or more of the orthopedic systems described herein.

For example, FIG. 7 shows an embodiment of a surgical orientation device 12. The surgical orientation device 12 can comprise a compact device for use in orienting a cutting guide or other surgical tool in a joint replacement procedure. In some techniques, the surgical orientation device 12 can be configured for being hand-held during a procedure. Preferably the surgical orientation device 12 is portable.

The surgical orientation device 12 can be used, for example, to identify an orientation of an anatomical plane, such as for example a plane defined by landmarks on a patient's acetabular rim. The surgical orientation device 12 can be used, for example, to measure distances, such as for example a distance between the reference post 14 and an anatomical landmark or landmarks on the patient's anatomy. Other uses are also possible. Furthermore, the surgical orientation device 12, as described herein, can be used alone or in conjunction with other devices, components, and/or systems, including but not limited to the sensor(s) 15 on the reference post 14, if included.

In a preferred arrangement, the surgical orientation device 12 can comprise a generally rectangular-shaped structure having an outer housing 30. The outer housing 30, as well as its contents can be portable. The outer housing 30 can be comprised, at least in part, of plastic including but not limited to ABS, polycarbonate, or other suitable material. The surgical orientation device 12 can be configured for hand-held use. The surgical orientation device 12 can be configured for mounting to other surgical devices, as discussed below.

With continued reference to FIG. 7, a front side 32, or a portion of the front side 32, of the surgical orientation device 12 can comprise a display 34. The display 34 can be a separate component from the outer housing 30 or can be integrated on or within the outer housing 30. The display 34 can comprise an output device. For example, the display 34 can comprise a liquid crystal display ("LCD") or Ferroelectric Liquid Crystal on Silicon ("FLCOS") display screen. The display screen can be sized such that a user can readily read numbers, lettering, and/or symbols displayed on the display screen while performing a medical procedure. In an embodiment, the display 34 comprises a Quarter Video Graphics Array ("QVGA") Thin Film Transistor ("TFT") LCD screen. Other types of display screens can also be used, as can other shapes, sizes, and locations for the display 24 on the surgical orientation device 12.

The surgical orientation device 12 can further comprise at least one user input device 36. The at least one user input device 36 can comprise a plurality of buttons located adjacent the display 34. The buttons can be activated, for example, by a finger, hand, and/or instrument to select a mode or modes of operation of the device 12, as discussed further below. In a preferred arrangement, the at least one user input comprises three buttons located underneath the display 34 as illustrated in FIG. 7. In other embodiments, the user input device 36 is a separate component from the housing 30. For example, the user input device 36 can comprise a remote input device coupled to the surgical orientation device 12 via a wired or wireless connection. In yet other embodiments, the user input device 36 comprises a microphone operating in conjunction with a speech recognition module configured to receive and process verbal instructions received from a user.

As discussed below, the surgical orientation device 12 can include a user interface with which a clinician can interact during a procedure. In one embodiment, the display 34 and at least one user input 36 can form a user interface. The user interface can allow a surgeon, medical personnel, and/or other user to operate the surgical orientation device 12 with ease, efficiency, and accuracy. Specific examples and illustrations of how the user interface can operate in conjunction with specific methods are disclosed further herein.

Figure 8:
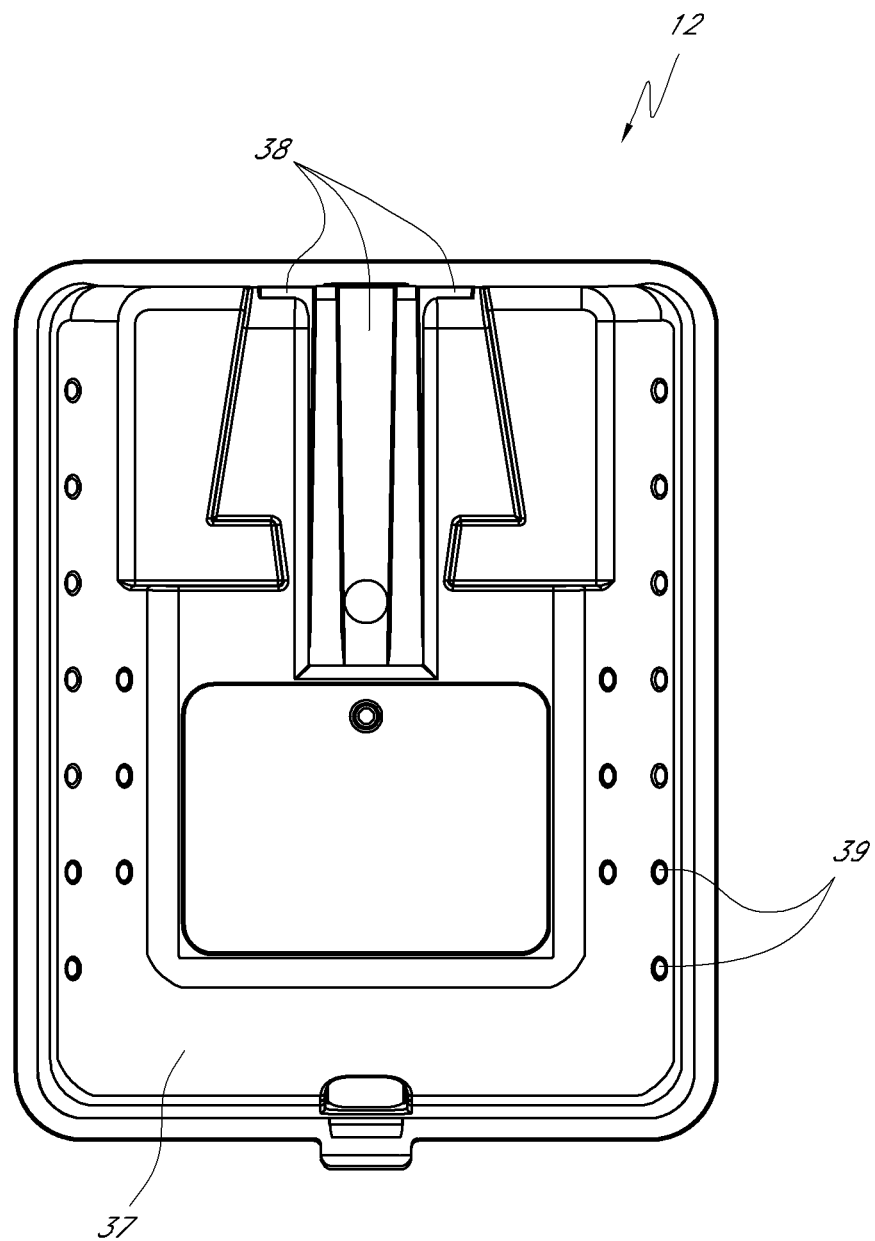
FIG. 8 is a back view of the surgical orientation device of FIG. 7.
Figure 9:
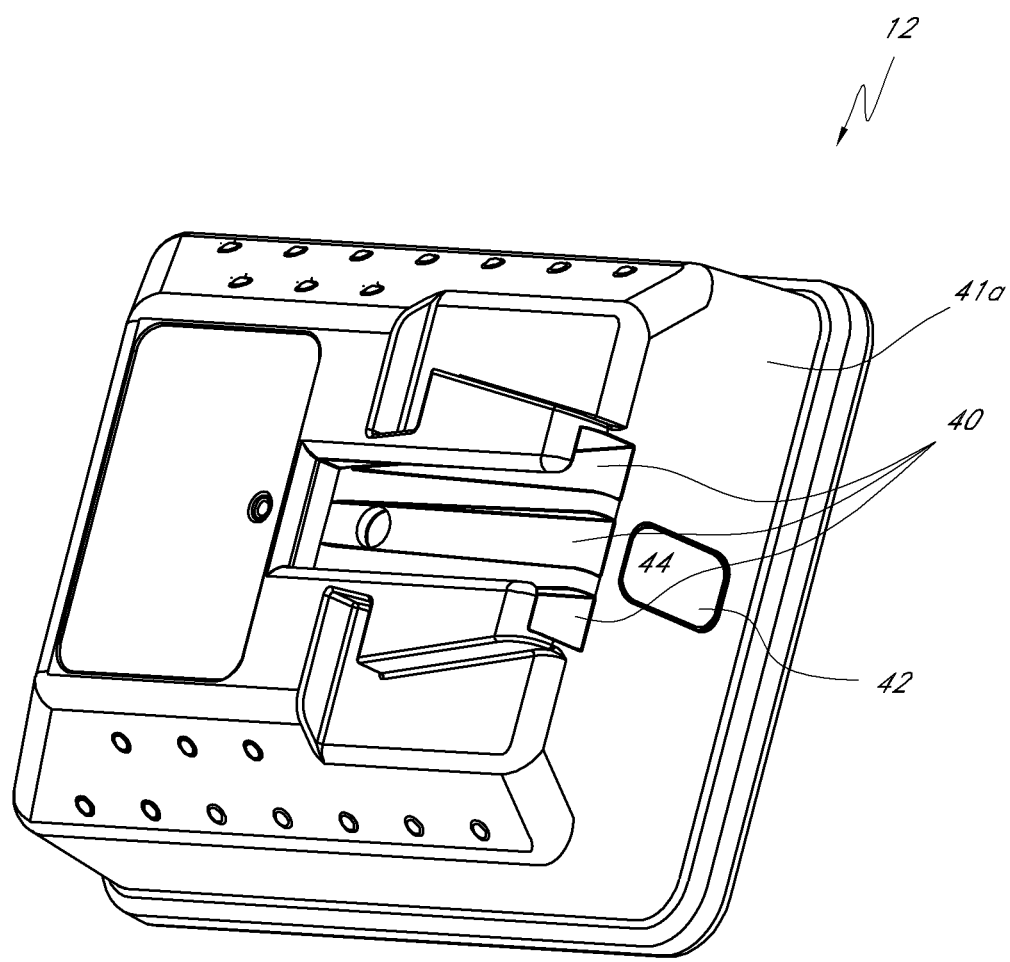
FIG. 9 is a perspective view of the surgical orientation device of FIG. 7.

FIGS. 8 and 9 show a back side 37 of the surgical orientation device 12. The back side 37 can include an attachment structure or structures 38, as well as a gripping feature or features 39 for facilitating handling of the surgical orientation device 12. The attachment structures 38 can facilitate attachment of the surgical orientation device 12 to another device, such as for example a coupling device (not shown). In a preferred arrangement, the attachment structures 38 comprise grooves, or channels 40, along a portion of the back side of the surgical orientation device 12.

Figure 10A:
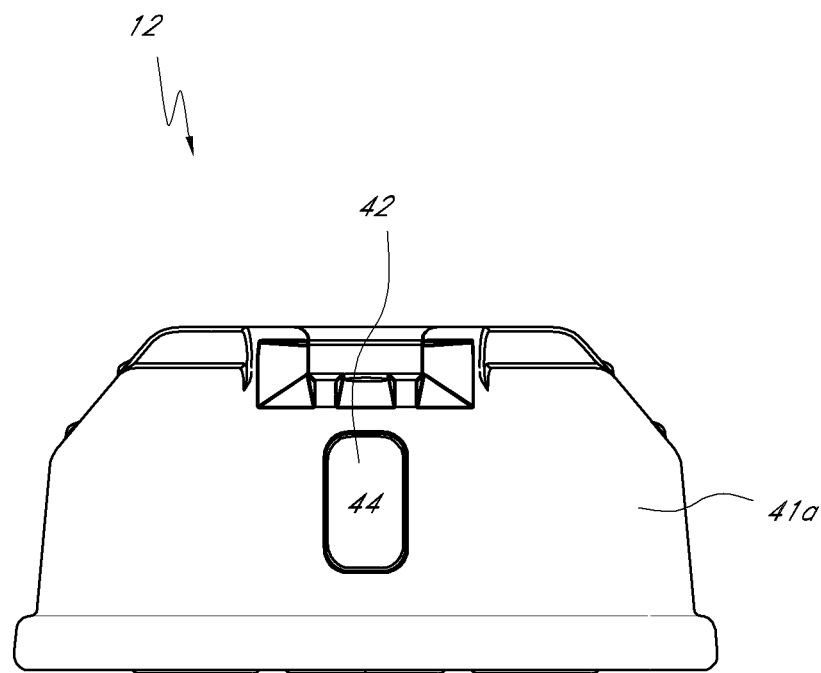
FIG. 10A is a top view of the surgical orientation device of FIG. 7.
Figure 10B:
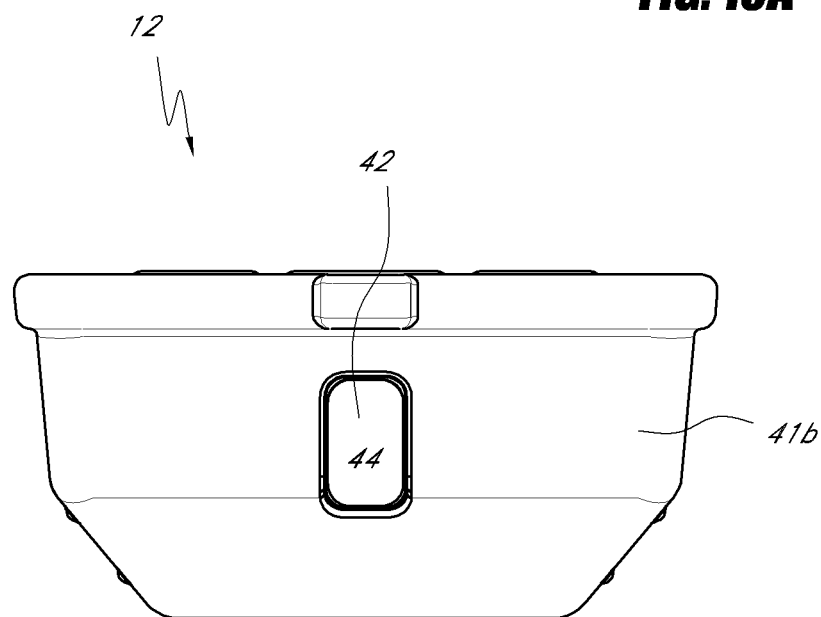
FIG. 10B is a bottom view of the surgical orientation device of FIG. 7.

The attachment structures 38 can be formed, for example, from protruding portions of the back side of the surgical orientation device 12, and can extend partially, or entirely, along the back side of the surgical orientation device 12. The attachment structures 38 can receive corresponding, or mating, structures from the coupling device 14, so as to couple, or lock, the coupling device to the surgical orientation device 12. FIGS. 10A and 10B show top and bottom sides 41a, 41b of the surgical orientation device 12. The surgical orientation device 12 can comprise optical components 42 that can be located on the top side 41a, the bottom side 41b, or the top and bottom sides 41a, 41b of the surgical orientation device 12. The optical components 42 can comprise transparent windows 44 integrated into the surgical orientation device 12. The optical components 42 can be windows that permit visible light (e.g. laser light) to emit from the top side 31a, the bottom side 31b, or both the top and bottom sides 41a, 41b of the surgical orientation device 12. While the embodiment illustrated in FIGS. 10a and 10b shows two windows 44 for transmitting light, other numbers are also possible. Additionally, while the optical components 42 are shown located on the top and bottom of the surgical orientation device 12, in other embodiments the optical components 42 can be located in other positions and/or on other portions of the surgical orientation device 12.

Figure 11:
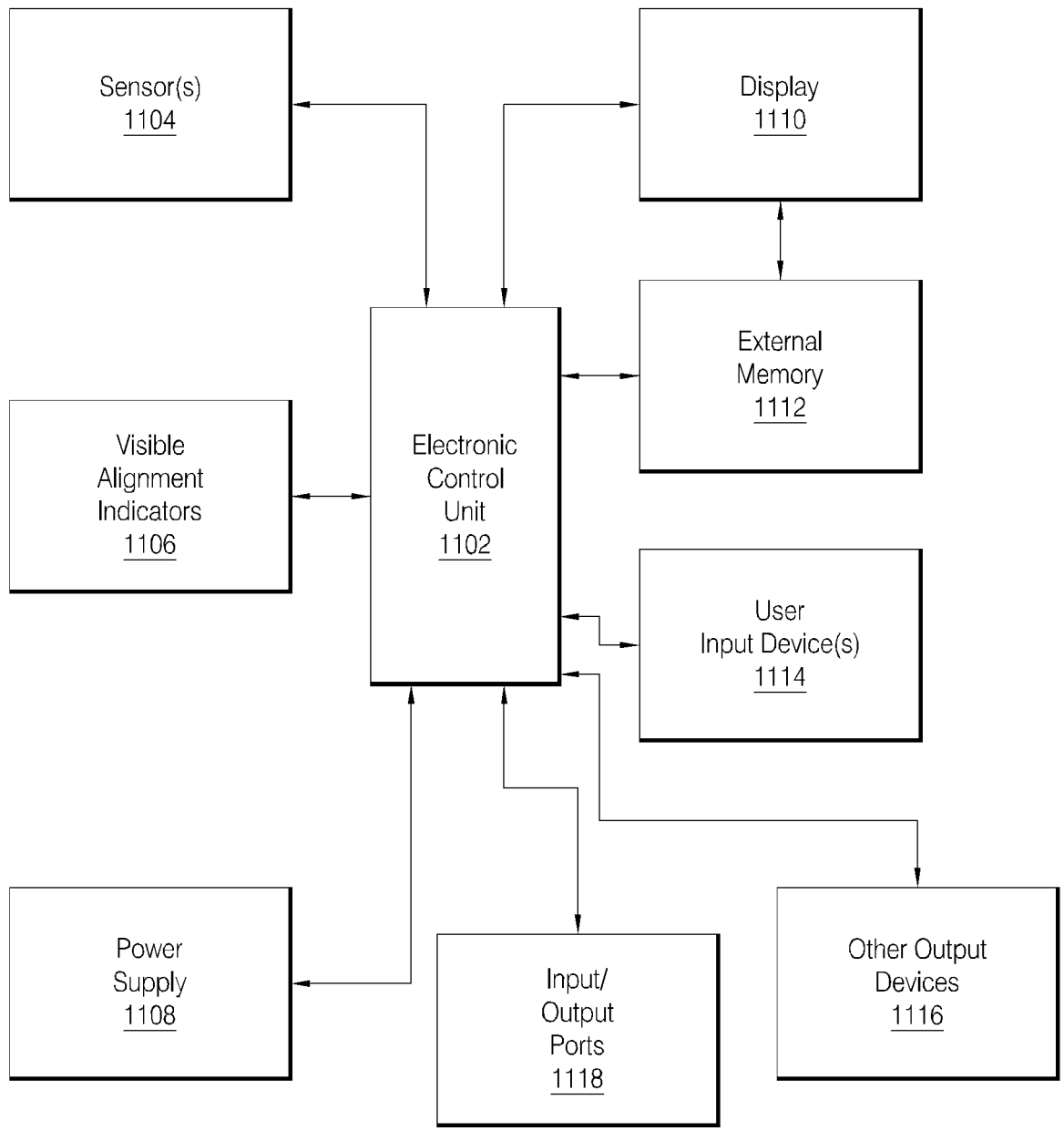
FIG. 11 is a block diagram of an electrical system of the surgical orientation device of FIG. 7.

FIG. 11 illustrates a high-level block diagram of an electrical system 1100 of the surgical orientation device 12. The electrical system 1100 comprises an electronic control unit 1102 that communicates with one or more sensor(s) 1104, one or more visible alignment indicators 1106, a power supply 1108, a display 1110, external memory 1112, one or more user input devices 1114, other output devices 1116 and/or one or more input/output ("I/O") ports 1118.

In general, the electronic control unit 1102 can receive input from the sensor(s), the external memory 1112, the user input devices 1114 and/or the I/O ports 1118 and controls and/or transmits output to the visible alignment indicators 1106, the display 1110, the external memory 1112, the other output devices 1116 and/or the I/O ports 1118. The electronic control unit 1102 can be configured to receive and send electronic data, as well as perform calculations based on received electronic data. In certain embodiments, the electronic control unit 1102 can be configured to convert the electronic data from a machine-readable format to a human readable format for presentation on the display 1110. The electronic control unit 1102 can comprise, by way of example, one or more processors, program logic, or other substrate configurations representing data and instructions, which can operate as described herein. In other embodiments, the electronic control unit 1102 can comprise controller circuitry, processor circuitry, processors, general purpose single-chip or multi-chip microprocessors, digital signal processors, embedded microprocessors, microcontrollers and/or the like. The electronic control unit 1102 can have conventional address lines, conventional data lines, and one or more conventional control lines. In yet other embodiments, the electronic control unit 1102 can comprise an application-specific integrated circuit (ASIC) or one or more modules configured to execute on one or more processors. In certain embodiments, the electronic control unit 1102 can comprise an AT91SAM7SE microcontroller available from Atmel Corporation.

The electronic control unit 1102 can communicate with internal memory and/or the external memory 1112 to retrieve and/or store data and/or program instructions for software and/or hardware. The internal memory and the external memory 1112 can include random access memory ("RAM"), such as static RAM, for temporary storage of information and/or read only memory ("ROM"), such as flash memory, for more permanent storage of information. In some embodiments, the external memory 1112 includes an AT49BV160D-70TU Flash device available from Atmel Corporation and a CY62136EV30LL-45ZSXI SRAM device available from Cypress Semiconductor Corporation. The electronic control unit 1102 can communicate with the external memory 1112 via an external memory bus.

In general, the sensor(s) 1104 can be configured to provide continuous real-time data to the surgical orientation device 12. The electronic control unit 1102 can be configured to receive the real-time data from the sensor(s) 1104 and to use the sensor data to determine, estimate, and/or calculate an orientation (e.g. position) of the surgical orientation device 12. The orientation information can be used to provide feedback to a user during the performance of a surgical procedure, such as a total hip replacement surgery, as described in more detail herein.

In some arrangements, the one or more sensors 1104 can comprise at least one orientation sensor configured to provide real-time data to the electronic control unit 1102 related to the motion, orientation (e.g. position) of the surgical orientation device 12. For example, a sensor module 1104 can comprise at least one gyroscopic sensor, accelerometer sensor, tilt sensor, magnetometer and/or other similar device or devices configured to measure, and/or facilitate determination of, an orientation of the surgical orientation device 12. The term "module" as used herein can include, but is not limited to, software or hardware components which perform certain tasks. Thus, a module can include object-oriented software components, class components, procedures, subroutines, data structures, segments of program code, drivers, firmware, microcode, circuitry, data, tables, arrays, etc. Those with ordinary skill in the art will also recognize that a module can be implemented using a wide variety of different software and hardware techniques.

In some embodiments, the sensors 1104 can be configured to provide measurements relative to a reference point(s), line(s), plane(s), and/or gravitational zero. Gravitational zero, as referred to herein, refers generally to an orientation in which an axis of the sensor 1104 is perpendicular to the force of gravity, and thereby experiences no angular offset, for example tilt, pitch, roll, or yaw, relative to a gravitational force vector. In other embodiments, the sensor(s) 1104 can be configured to provide measurements for use in dead reckoning or inertial navigation systems.

In various embodiments, the sensor(s) 1104 comprise one or more accelerometers that measure the orientation of the surgical orientation device 12 relative to gravity. For example, the accelerometers can be used as tilt sensors to detect rotation of the surgical orientation device 12 about one or more of its axes. For example, the one or more accelerometers can comprise a dual axis accelerometer (which can measure rotation about two axes of rotation). The changes in orientation about the axes of the accelerometers can be determined relative to gravitational zero and/or to a reference plane registered during a tibial or femoral preparation procedure as described herein.

In certain embodiments, a multi-axis accelerometer (such as the ADXL203CE MEMS accelerometer available from Analog Devices, Inc. or the LIS331DLH accelerometer available from ST Microelectronics.) detects changes in orientation about two axes of rotation. For example, the multi-axis accelerometer can detect changes in angular position from a horizontal plane (e.g., anterior/posterior rotation) of the surgical orientation device 12 and changes in angular position from a vertical plane (e.g., roll rotation) of the surgical orientation device 12. The changes in angular position from the horizontal and vertical planes of the surgical orientation device 12 as measured by the sensor 1104 can be used to determine changes in orientation of the surgical orientation device 12.

In some arrangements, the sensors 1104 can comprise at least one single- or multi-axis gyroscope sensor and at least one single- or multi-axis accelerometer sensor. For example, a sensor module 1104 can comprise a three-axis gyroscope sensor (or three gyroscope sensors) and a three-axis accelerometer (or three accelerometer sensors) to provide orientational measurements for all six degrees of freedom of the surgical orientation device 12. In some embodiments, the sensors provide an inertial navigation or dead reckoning system to continuously calculate the orientation and velocity of the surgical orientation device 12 without the need for external references In some embodiments, the sensors 1104 comprise one or more accelerometers and at least one magnetometer. The magnetometer can be configured to measure a strength and/or direction of one or more magnetic fields in the vicinity of the surgical orientation device 12. The magnetometer can advantageously be configured to detect changes in angular position about a vertical axis. In other embodiments, the sensors 1104 comprise one or more sensors capable of determining distance measurements. For example a sensor located in the surgical orientation device 12 can be in electrical communication (wired or wireless) with an emitter element mounted at the end of a measurement probe. For example, sensor 15 in reference post 14 can comprise an emitter element. In certain embodiments, the electrical control unit can be configured to determine the distance between the sensor and emitter (for example, an axial length of a measurement probe corresponding to a distance to an anatomical landmark, such as a bony eminence of the pelvis or femur, such as the greater or lesser trochanter).

In other embodiments, the one or more sensors 1104 can comprise a temperature sensor to monitor system temperature of the electrical system 1100. Operation of some of the electrical components can be affected by changes in temperature. The temperature sensor can be configured to transmit signals to the electronic control unit 1102 to take appropriate action. In addition, monitoring the system temperature can be used to prevent overheating. In some embodiments, the temperature sensor comprises a NCP21WV103J03RA thermistor available from Murata Manufacturing Co. The electrical system 1100 can further include temperature, ultrasonic and/or pressure sensors for measuring properties of biological tissue and other materials used in the practice of medicine or surgery, including determining the hardness, rigidity, and/or density of materials, and/or determining the flow and/or viscosity of substances in the materials, and/or determining the temperature of tissues or substances within materials.

In certain embodiments, the sensors 1104 can facilitate determination of an orientation of the surgical orientation device 12 relative to a reference orientation established during a preparation and alignment procedure performed during orthopedic surgery. Further details regarding the operation of the sensors in conjunction with a total hip replacement surgery are described herein.

The one or more sensors 1104 can form a component of a sensor module that comprises at least one sensor, signal conditioning circuitry, and an analog-to-digital converter ("ADC"). In certain embodiments, the components of the sensor module 1104 are mounted on a stand-alone circuit board that is physically separate from, but in electrical communication with, the circuit board(s) containing the other electrical components described herein. In other embodiments, the sensor module is physically integrated on the circuit board(s) with the other electrical components. The signal conditioning circuitry of the sensor module can comprise one or more circuit components configured to condition, or manipulate, the output signals from the sensor(s) 1104. In certain embodiments, the signal conditioning circuitry comprises filtering circuitry and gain circuitry. The filtering circuitry can comprise one more filters, such as a low pass filter. For example, a 10 Hz single pole low pass filter can be used to remove vibrational noise or other low frequency components of the sensor output signals. The gain circuitry can comprise one or more operational amplifier circuits that can be used to amplify the sensor output signals to increase the resolution potential of the sensor. For example, the operational amplifier circuit can provide gain such that a 0 g output results in a midrange (e.g., 1.65 V signal), a +1 g output results in a full scale (e.g., 3.3 V) signal and a −1 g output results in a minimum (0 V) signal to the ADC input.

In general, the ADC of the sensor module can be configured to convert the analog output voltage signals of the sensor(s) 1104 to digital data samples. In certain embodiments, the digital data samples comprise voltage counts. The ADC can be mounted in close proximity to the sensor to enhance signal to noise performance. In certain embodiments, the ADC comprises an AD7921 two channel, 12-bit, 250 Kiloseconds per Sample ADC. In an arrangement having a 12-bit ADC can generate 4096 voltage counts. The ADC can be configured to interface with the electronic control unit 1102 via a serial peripheral interface port of the electronic control unit 1102. In other embodiments, the electronic control unit 1102 can comprise an on-board ADC that can be used to convert the sensor output signals into digital data counts.

With continued reference to FIG. 11, the visible alignment indicators 1106 can comprise one or more lasers, which can be configured to project laser light through the optical component or components 32 described above. For example, the visible alignment indicators 1106 can comprise a forward laser and an aft laser. The laser light can be used to project a point, a plane, and or a cross-hair onto a target or targets, including but not limited to an anatomical feature or landmark, to provide alternative or additional orientation information to a surgeon regarding the orientation of the orientation device 12. For example, laser light can be used to project a plane on a portion of bone to indicate a resection line and a cross-hair laser pattern can be used to ensure alignment along two perpendicular axes. In certain embodiments, the laser light or other type of probe (e.g. a mechanical probe such as an elongate rod) can be used to mark or identify landmarks on the patient's hip area, such as the lesser trochanter and/or iliac spine. In certain embodiments, the laser light or other type of probe can be used to constrain a degree of freedom, such as rotation about a vertical axis, of an instrument relative to anatomy or one instrument relative to another. The probe can be used, for example, to return an instrument to a specific rotational orientation. In certain embodiments, the visible alignment indicators 1106 can be used to determine a distance to an anatomical feature or landmark (for example, a laser distance measurement system). For example, the electronic control unit 1102 can project laser light to a target and a sensor 1104 within the surgical orientation device can sense the laser light reflected back from the target and communicate the information to the electronic control unit. The electronic control unit 1102 can then be configured to determine the distance to the target. The lasers can be controlled by the electronic control unit 1102 via pulse width modulation ("PWM") outputs. In certain embodiments, the visible alignment indicators 1106 comprise Class 2M lasers. In other embodiments, the visible alignment indicators 1106 comprises other types of lasers or light sources.

The power supply 1108 can comprise one or more power sources configured to supply DC power to the electronic system 1100 of the surgical orientation device 12. In certain embodiments, the power supply 1108 comprises one or more rechargeable or replaceable batteries and/or one or more capacitive storage devices (for example, one or more capacitors or ultracapacitors). In other embodiments, power can be supplied by other wired and/or wireless power sources. In preferred arrangements, the power supply 1108 comprises two AA alkaline, lithium, or rechargeable NiMHI batteries. The surgical orientation device 12 can also include a DC/DC converter to boost the DC power from the power supply to a fixed, constant DC voltage output (e.g., 3.3 volts) to the electronic control unit 1102. In some embodiments, the DC/DC converter comprises a TPS61201DRC synchronous boost converter available from Texas Instruments. The electronic control unit 1106 can be configured to monitor the battery level if a battery is used for the power supply 1108. Monitoring the battery level can advantageously provide advance notice of power loss. In certain embodiments, the surgical orientation device 12 can comprise a timer configured to cause the surgical orientation device 12 to temporarily power off after a predetermined period of inactivity and/or to permanently power off after a predetermined time-out period.

As discussed above, the display 1110 can comprise an LCD or other type screen display. The electronic control unit 1102 communicates with the display via the external memory bus. In certain embodiments, the electronic system 1100 comprises a display controller and/or an LED driver and one or more LEDs to provide backlighting for the display 1110. For example, the display controller can comprise an LCD controller integrated circuit ("IC") and the LED driver can comprise a FAN5613 LED driver available from Fairchild Semiconductor International, Inc. The electronic control unit 1102 can be configured to control the LED driver via a pulse width modulation port to control the brightness of the LED display. For example, the LED driver can drive four LEDs spaced around the display screen to provide adequate backlighting to enhance visibility. The display can be configured to display one or more on-screen graphics. The on-screen graphics can comprise graphical user interface ("GUI") images or icons. The GUI images can include instructive images, such as illustrated surgical procedure steps, or visual indicators of the orientation information received from the sensor(s) 1104. For example, the display can be configured to display degrees and either a positive or negative sign to indicate direction of rotation from a reference plane and/or a bubble level indicator to aid a user in maintaining a particular orientation. The display can also be configured to display alphanumeric text, symbols, and/or arrows. For example, the display can indicate whether a laser is on or off and/or include an arrow to a user input button with instructions related to the result of pressing a particular button.

With continued reference to FIG. 11, the user input device(s) 1114 can comprise buttons, switches, a touchscreen display, a keyboard, a joystick, a scroll wheel, a trackball, a remote control, a microphone, and the like. The user input devices 1114 can allow the user to enter data, make selections, input instructions or commands to the surgical orientation device 12, verify a position of the surgical orientation device 12, turn the visible alignment indicators 1106 on and off, and/or turn the entire surgical orientation device 12 on and off. The other user output devices 1116 (i.e., other than the display 1110) can comprise an audio output, such as a speaker, a buzzer, an alarm, or the like. For example, the audio output can provide a warning to the user when a particular condition occurs. The output devices 1116 can also comprise a visible output, such as one or more LED status or notification lights (for example, to indicate low battery level, an error condition, etc.). The audio output can comprise different patterns, tones, cadences, durations, and/or frequencies to signify different conditions or events. In other embodiments, output from the electronic control unit 1102 can be sent to external display devices, data storage devices, servers, and/or other computing devices (e.g., via a wireless network communication link).

The I/O ports 1118 of the electronic control unit 1102 can comprise a JTAG port and one or more serial communication ports. The JTAG port can be used to debug software installed on the electronic control unit 1102 during testing and manufacturing phases. The JTAG port can be configured such that it is not externally accessible post-manufacture. The serial communication ports can include a Universal Serial Bus ("USB") port and/or one or more universal asynchronous receiver/transmitters ("UART") ports. At least one of the UART ports can be accessible externally post-manufacture. The external UART port can be an infrared ("IR") serial port in communication with an infrared ("IR") transceiver. The IR serial port can be used to update the software installed on the electronic control unit 1102 post-manufacture and/or to test the operation of the electronic control unit 1102 by outputting data from the electronic control unit 1102 to an external computing device via an external wireless connection. Other types of I/O ports are also possible.

Figure 12A:
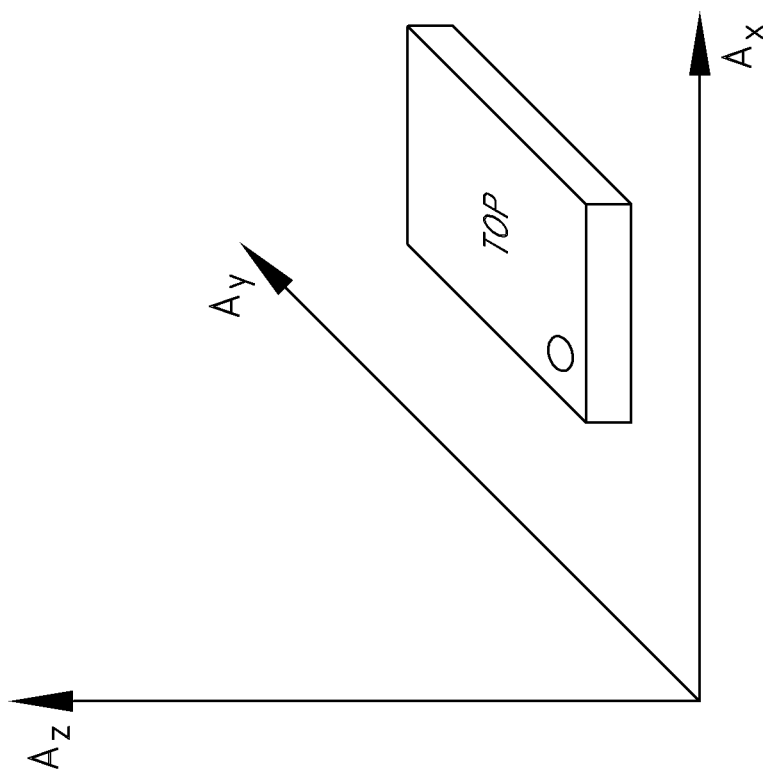
FIGS. 12A-C illustrate operation of accelerometers according to embodiments that can be used as sensors in the electrical system of FIG. 11.

As described above, the sensor(s) 1104 can comprise one or more accelerometers. Accelerometers can measure the static acceleration of gravity in one or more axes to measure changes in tilt orientation. For example, a three-axis accelerometer can measure the static acceleration due to gravity along three orthogonal axes, as illustrated in FIG. 12A. A two-axis accelerometer can measure the static acceleration due to gravity along two orthogonal axes (for example, the x and y axes of FIG. 12A). The output signals of an accelerometer can comprise analog voltage signals. The output voltage signals for each axis can fluctuate based on the fluctuation in static acceleration as the accelerometer changes its orientation with respect to the gravitational force vector. In certain embodiments, an accelerometer experiences static acceleration in the range from −1 g to +1 g through 180 degrees of tilt (with −1 g corresponding to a −90 degree tilt, 0 g corresponding to a zero degree tilt, and +1 g corresponding to a +90 degree tilt. The acceleration along each axis can be independent of the acceleration along the other axis or axes.

Figure 12B:
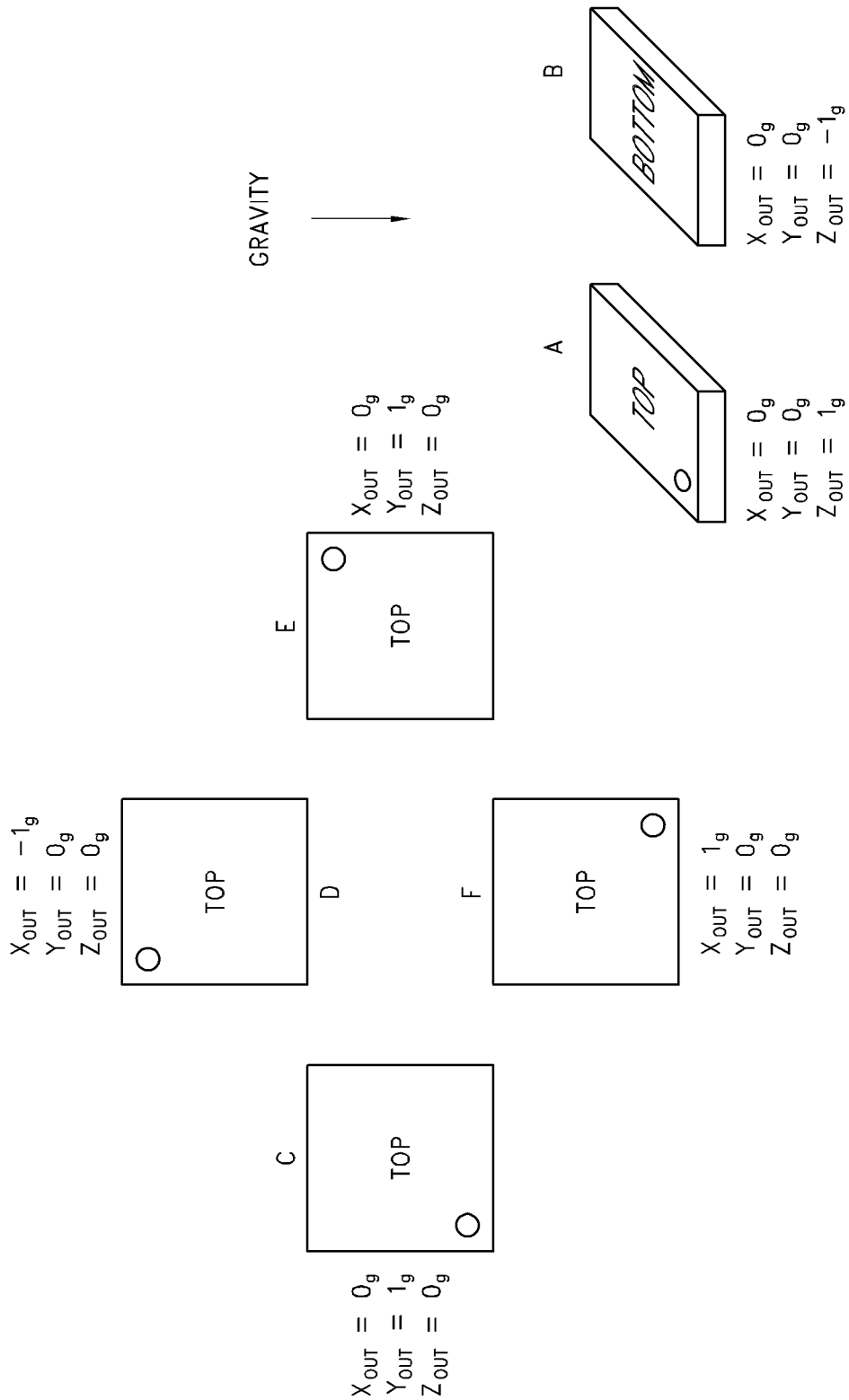

FIG. 12B illustrates a measured acceleration along each of the three axes of a three-axis accelerometer in six different orientation positions. TOP and BOTTOM labels, as well as a circle indicating Pin 1 of the accelerometer, have been included to aid in determining the various orientations. A gravitational force reference vector is illustrated as pointing straight down toward the Earth's surface. At positions A and B, the x-axis and the y-axis of the accelerometer are perpendicular to the force of gravity and the z-axis of the accelerometer is parallel to the force of gravity; therefore, the x and y acceleration components of static acceleration due to gravity at positions A and B are 0 g and the z component of static acceleration due to gravity at positions A and B is +1 g and −1 g, respectively. At positions C and E, the x-axis and the z-axis of the accelerometer are perpendicular to the force of gravity and the y-axis is parallel to the force of gravity; therefore, the x and z acceleration components of static acceleration due to gravity at positions C and E are 0 g and the y component of static acceleration due to gravity at positions C and E is +1 g and −1 g, respectively. At positions D and F, the y-axis and z-axis are perpendicular to the force of gravity and the x-axis is parallel to the force of gravity; therefore, the y and z acceleration components of static acceleration due to gravity at positions D and F are 0 g and the x component of static acceleration due to gravity at positions D and F is +1 g and −1 g, respectively. A dual-axis accelerometer operates in the same manner but without the z component. In certain arrangements, a three-axis accelerometer can be used as a tiltmeter to measure changes in orientation about two axes.

Figure 12C:
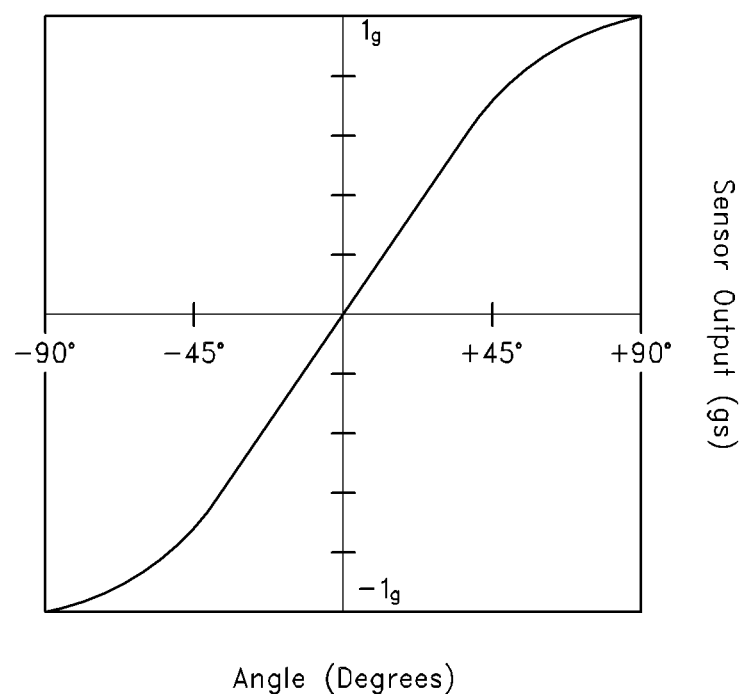

Multi-axis accelerometers can be conceptualized as having a separate accelerometer sensor for each of its axes of measurement, with each sensor responding to changes in static acceleration in one plane. In certain embodiments, each accelerometer sensor is most responsive to changes in tilt (i.e., operates with maximum or optimum accuracy and/or resolution) when its sensitive axis is substantially perpendicular to the force of gravity (i.e., when the longitudinal plane of the accelerometer sensor is parallel to the force of gravity) and least responsive when the sensitive axis is parallel to the force of gravity (i.e., when the longitudinal plane of the accelerometer sensor is perpendicular to the force of gravity). FIG. 12C illustrates the output of the accelerometer in g's as it tilts from −90 degrees to +90 degrees. As shown, the tilt sensitivity diminishes between −90 degrees and −45 degrees and between +45 degrees and +90 degrees (as shown by the decrease in slope). This resolution problem at the outer ranges of tilt motion makes the measurements much less accurate for tilt measurements over 45 degrees. In certain embodiments, when the mounting angle of the surgical orientation device 12 is known, the sensor(s) 1104 can be mounted to be offset at an angle such that the accelerometer sensors can operate in their more accurate, steeper slope regions. For example, for use during the knee surgery preparation procedures described herein, the sensor(s) 1104 can be mounted at approximately a 22-degree angle relative to the anterior-posterior axis of the surgical orientation device 12 to account for a predetermined range of motion of the surgical orientation device 12 about the flexion/extension axis during the procedures. It should be appreciated by one of ordinary skill in the art that the accelerometer can be mounted at acute angles other than approximately 22 degrees. In other arrangements, the sensor(s) 1104 can be mounted to be offset to account for a predetermined range of motion about other axes of rotation as well. In yet other arrangements, for example, when a three-axis accelerometer is used, the accelerometer sensor(s) can be mounted in parallel with the anterior-posterior axis of the surgical orientation device 12. In one three-axis accelerometer arrangement, a handoff system can be incorporated to ensure that the accelerometer sensors with the most accurate reading (e.g., <45 degrees) are being used at each orientation position. The handoff system can employ hysteresis to avoid "bouncing" phenomena during the handoffs between the accelerometer sensors.

Figure 12D:
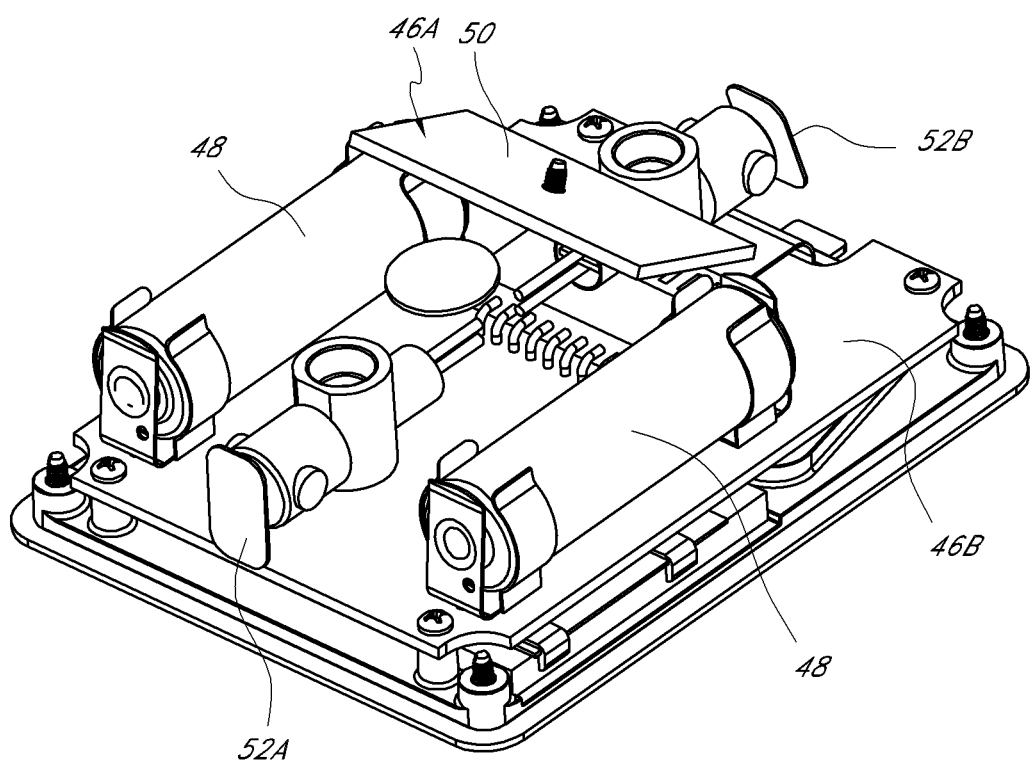
FIG. 12D is a perspective view of interior components of the surgical orientation device of FIG. 7.

FIG. 12D illustrates the inside of the surgical orientation device 12 according to at least one embodiment. The surgical orientation device 12 can comprise one or more circuit boards and/or other circuitry capable of installation within the surgical orientation device 12. As illustrated, the surgical orientation device 12 can comprise a sensor board 46A and a main board 46B. The components of the sensor module (including the sensor(s) 1104) can be mounted on the sensor board 46A and the other components of the electrical system 1100 are mounted on the main board 46B. The sensor board 46A can comprise one or more sensors 50 (e.g., sensor(s) 1104 as described above). In alternative embodiments, the sensor board 46A and the main board 46B can be combined into a single circuit board. The sensor board 46A and the main board 46B can comprise rigid or flexible circuit boards. The sensor board 46A and the main board 46B can be fixedly or removably coupled to the outer housing 20.

As illustrated, the sensor board 46A is mounted at an approximately 22-degree angle relative to a plane extending longitudinally through the housing 30, which can be parallel to or correspond to an anterior-posterior axis of the main board 46B. As described above, mounting the sensor board 46A at an offset angle can enable the one or more sensors to operate in the regions of maximum or optimum sensitivity, accuracy and/or resolution. The particular mounting offset angle can be selected based on a range of motion of the surgical orientation device 12 during a particular orthopedic procedure. As shown in FIG. 12D, the surgical orientation device 12 can include two AA batteries 38 as the power supply 1110 for providing power to the surgical orientation device 12. The surgical orientation device 12 also can include lasers 42 as the visible alignment indicators 1106 described above.

Figure 12E:
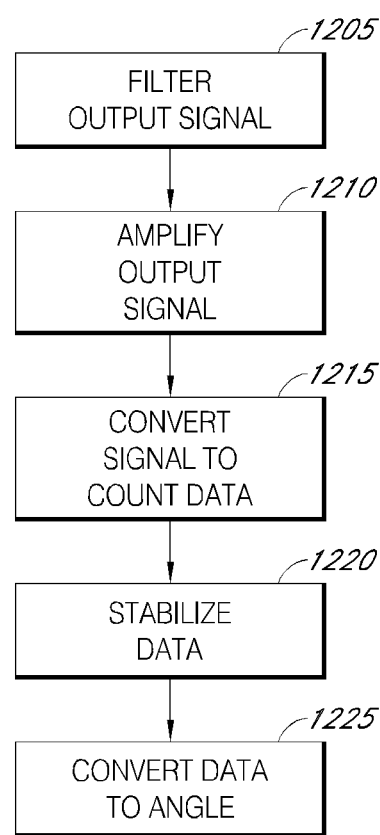
FIG. 12E is a flow chart of an embodiment of an orientation measurement process performed by the surgical orientation device of FIG. 7.

FIG. 12E is a high-level flowchart of an exemplary conversion process for converting an analog voltage output signal of a multi-axis accelerometer into an angle degree measurement for presentation on the display 34. Although the steps are described as being implemented with hardware and/or software, each of the steps illustrated in FIG. 12E can be implemented using hardware and/or software. It should be appreciated that a similar conversion process can be performed for any other type of sensor or for multiple separate sensors without departing from the spirit and/or scope of the disclosure.

For each axis of rotation measured (e.g., pitch and roll), the multi-axis accelerometer can continuously output an analog voltage signal. At Block 1205, the signal conditioning circuitry of the sensor module can filter the analog output voltage signal (e.g., with a low pass filter) to remove noise from the signal that may be present due to the high sensitivity of the multi-axis accelerometer. At Block 1210, the signal conditioning circuitry amplifies, or boosts, the output voltage signal, for example, via the gain circuitry described above.

At Block 1215, the ADC can convert the continuous analog voltage signal into a discrete digital sequence of data samples, or voltage counts. In certain embodiments, the ADC can sample the analog voltage signal once every two milliseconds; however, other sampling rates are possible. In certain embodiments, the analog voltage signal is oversampled. At Block 1220, the electronic control unit 1102 can generate a stable data point to be converted to an angle measurement. The electronic control unit 1102 can apply a median filter to the sampled data to eliminate outliers (e.g., spikes) in the data. For example, the electronic unit 1102 can use an 11-sample median filter to generate the middle value from the last 11 samples taken. The output of the median filter can then be fed into a rolling average filter (for example, a 128 sample rolling average filter). The rolling average filter can be used to smoothe or stabilize the data that is actually converted to an angle measurement. The electronic control unit 1102 can implement Blocks 1215 and 1220 using a finite impulse response ("FIR") or an infinite impulse response ("IIR") filter implemented in a software module.

At Block 1225, the electronic control unit 1102 can convert the voltage count data to an angle measurement in degrees. In performing the conversion, the electronic control unit 1102 can be configured to apply a calibration conversion algorithm based on a calibration routine performed during a testing phase prior to sale of the surgical orientation device 12. The calibration conversion can be configured to account for unit-to-unit variations in components and sensor placement. The calibration routine can be performed for each axis being monitored by the multi-axis accelerometer. The calibration conversion can comprise removing any mechanical or electrical offsets and applying an appropriate gain calibration for a positive or negative tilt.

As described above, the ADC can comprise an ADC with 12-bit resolution, which provides 4096 distinct voltage counts, wherein a −90 degree tilt corresponds to 0 counts (−2048 signed counts), a zero degree tilt corresponds to 2048 counts (0 signed counts), and a +90 degree tilt corresponds to 4096 counts (+2048 signed counts). The tilt angle for each axis (e.g., pitch and roll) of the multi-axis accelerometer can be calculated from the voltage count data based on standard trigonometric relationships as the arcsin of the acceleration component in each particular axis. In arrangements in which the electronic control unit 1102 applies the calibration conversion, the tilt angle for each axis can be calculated as follows:

$$\text{ANGLE} = a\sin\left[\frac{(\textit{SignedADC Counts} + \text{OFFSET}) \times \text{GAIN}}{2048}\right], \quad (12.1)$$

where OFFSET corresponds with a zero offset of the surgical orientation device 12 determined during the calibration routine and GAIN corresponds with a ratiometric value determined during the calibration routine, with one GAIN value being used for negative tilt angles and a different GAIN value being used for positive tilt angles.

Also at Block 1225, in arrangements where a dual-axis accelerometer is used, the electronic control unit 1102 can be configured to adjust the pitch angle (x axis) calculation to account for the mounting offset angle (described above) of the dual-axis accelerometer relative to the outer housing 20 of the surgical orientation device 20. The result of Block 1225 is an absolute angle for each axis of rotation (e.g., pitch, roll) being monitored by the dual-axis accelerometer. The absolute pitch and roll angles can be used to calculate orientation measurements of the surgical orientation device 12.

Orientation measurements for the surgical orientation device 12 can be determined based on a wide variety of reference frames in conjunction with any of a variety of surgical procedures.

In certain embodiments, calculations can be performed by software modules executed by the electronic control unit 1102. In other embodiments, the electronic control unit 1102 can generate measurements using data stored in one or more look-up tables ("LUT"s). In other embodiments, other calculations can be derived based on the type of sensor or sensors used, the procedure being performed, and/or the reference frame being employed. Specific calculations in accordance with other procedures are described, for example, in U.S. patent application Ser. No. 12/509,388, filed Jul. 24, 2009, the contents of which are incorporated in their entirety by reference herein.

In certain embodiments, the electronic control unit 1102 can perform a stabilization routine, process, or algorithm to assess or determine the stability, or reliability, of the calculated angle measurements. For example, the electronic control unit 1102 can keep a history of the last 100 ms of calibrated sample data for each axis being monitored by the sensor(s) 40. Each time a new sample is added to the 100-sample history, a maximum and minimum value is determined for the 100-sample data set. The electronic control unit 1102 can then determine a delta difference between the maximum and minimum values. The electronic control unit 1102 can then compare the delta difference between the maximum and minimum values to a threshold. If the delta difference is lower than the threshold, then the data is considered to be stable and it is stored in memory (e.g., external memory 1112) and time-stamped. If the delta difference is greater than the threshold, then the data is considered to be unstable. When retrieving an angle reading to display to the user, the electronic control unit 1102 can be configured to transmit the last stable data reading (assuming it is not too old) to the display 1110 instead of the current unstable reading. If the last stable angle exceeds a time threshold, the unstable angle reading can be displayed along with a visual indication notifying the user that the angle reading is unstable. For example, a red "shaky hand" icon or graphical user interface image can be displayed on the display screen.

B. Orthopedic System for Measuring Distances in a Joint

Figure 3A:
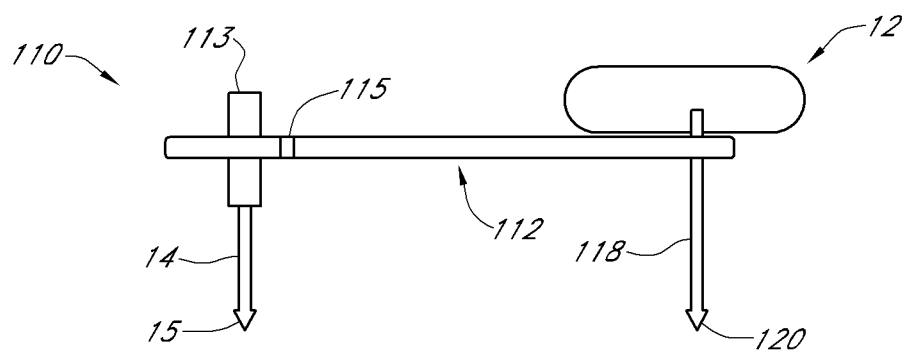
FIG. 3A is a side view of an orthopedic system according to one embodiment for measuring distances in and around a joint.
Figure 3B:
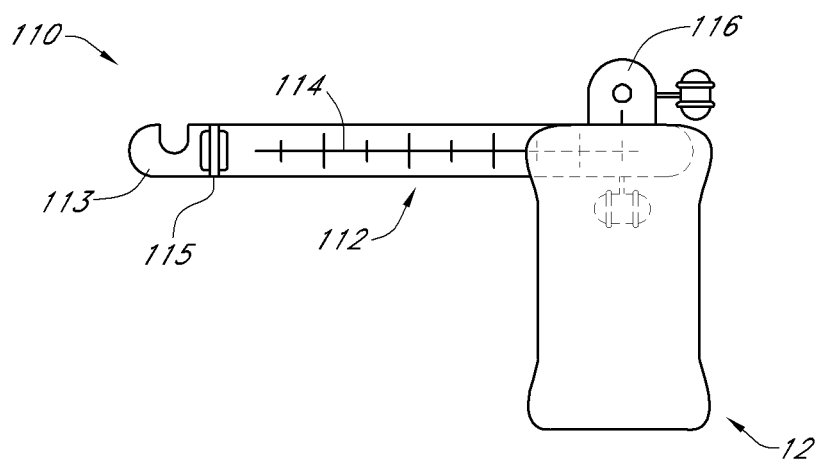
FIG. 3B is a top view of the orthopedic system of FIG. 3A.

With reference to FIGS. 3A and 3B, a orthopedic system 110 can be used to measure distances in a joint. These distances can be measured between, for example, a reference (e.g. reference post 14) and an anatomical landmark (e.g. a predetermined landmark such as the lesser trochanter). The distances can be measured both before a procedure as well as after a procedure to determine whether the procedure has been successful. The orthopedic system 110 can comprise the surgical orientation device 12 described above, the reference post 14 described above (including, for example, sensor 15), a measuring device 112 and a marking device 118.

1. Device for Measuring Distances in a Joint

With continued reference to FIGS. 3A and 3B, the measuring device 112 can comprise a structure or structures (e.g. an elongate structure) which facilitate measurement of a distance between the fixed reference post 14 and an anatomical reference or references. The measuring device 112 can comprise an angle assessment guide. The measuring device 112 can be releasably coupled to the reference post 14. For example, the measuring device 112 can comprise a coupling device 113 or other structure which connects the measuring device 112 to the proximal end 30 of the reference post 14'. The measuring device 112 can include a marking or markings 114 along at least one side or portion. The markings 114 can provide the user with visual evidence of the distance between the fixed reference post 14 and the marking device 118.

The measuring device 112 can further include a hinge 115. The hinge 115 can allow the measuring device 112, or a portion of the measuring device 112, to be pivotably rotated relative to the reference post 14. In some embodiments, the measuring device 12 and marking device 118 can be both pivotably rotated about the hinge 115, as well as rotated about the coupling device 113. For example, the hinge 115 and coupling device 113 can allow for rotational movement of the marking device 118 in both a first plane, as well as a second plane orthogonal to the first plane. Thus, the measuring device 18 can be moved in at least two degrees of rotational freedom.

In some embodiments, the marking device 118 can comprise a laser device. For example, a laser can be emitted from a marking device 118 and/or measuring device 112. The laser can contact and/or reference an anatomical location, and such location can be used to obtain a measurement or measurements as described herein.

The measuring device 112 can further comprise an attachment structure 116. The attachment structure 116 can releasably attach the surgical orientation device 12 to the measuring device 112. The attachment structure 116 can comprise a coupling device or devices that allows the surgical orientation device 12 and/or marking device 118 to move relative to the measuring device 112. For example, in a preferred arrangement, when the reference post 14 is fixed into the patient's bony anatomy, the surgical orientation device 12 and marking device 118 can slide longitudinally along a length of the measuring device 112, thereby changing the relative distance between the reference post 14 and the marking device 118. The attachment device 116 can further allow the marking device 118 to be moved generally through a range of elevations so as to bring the marking device closer to or in contact with an anatomical landmark. As described above, the surgical orientation device 12 can be configured to detect translational changes. Thus, both the markings 114 and surgical orientation device itself can facilitate an accurate measurement of a distance between the proximal end 30 of reference post 14 and the marking device 118.

2. Device for Marking an Anatomical Landmark

With continued reference to FIG. 3B, the marking device 118 can comprise a pin or other structure which can be used to physically pinpoint and/or contact an anatomical landmark. For example, and as described further herein, an end 120 of the marking device 118 can be brought into contact with and/or placed adjacent the lesser trochanter, and the location on the lesser trochanter can be marked with an ink or some other marking agent, such as for example a methylene blue marker. The marking device 118 can be releasably coupled to the surgical orientation device 12, such that any movement of the surgical orientation device 12 causes identical movement of the marking device 118. The marking device 118 can visually indicate a position of an anatomical landmark during a procedure. In certain embodiments, the marking device 118 can be a laser which projects a point of light down onto the anatomy without making physical contact or impairing access to or visualization of the joint space. In certain embodiments a fan-style laser can be incorporated into the system to be substantially in alignment with the measuring device 112. The laser can be used as an aid to align an axis of the measuring device 112 (e.g. the "leg length" axis) with an axis of the leg by orienting the measuring device 112 such that the laser line passes through the center of the knee, ankle or other appropriate landmark.

C. Orthopedic System for Determining an Orientation of a Plane in a Patient's Anatomy With reference to FIG. 4, an orthopedic system 210 can be used to determine the orientation of an anatomical plane in the human anatomy, such as for example an anatomical plane defined by a landmark or landmarks along the acetabular rim in a patient's pelvic area. The orthopedic system 210 can comprise the surgical orientation device 12 described above, and an anatomical contact device 214.

1. Anatomical Contact Device for Contacting a Landmark or Landmarks

Figure 4:
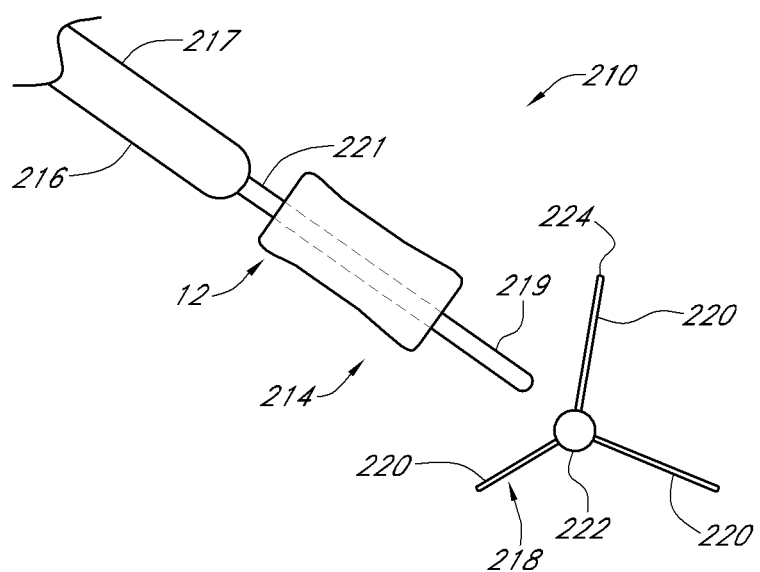
FIG. 4 is an exploded perspective view of a orthopedic system according to one embodiment for determining an orientation of a plane in a patient's anatomy.

With continued reference to FIG. 4, the anatomical contact device 214 can comprise a hand-held and/or portable orthopedic device which comprises at least one component that contacts at least one anatomical landmark on the patient's anatomy. For example, the anatomical contact device 214 can comprise an alignment handle 216 which is releasably coupled to the surgical orientation device 12. The alignment handle 216 can comprise a proximal end 217 with a handle, a distal end 219, and an elongate member 221 extending therebetween. The alignment handle 216 can be gripped by a user's hand and moved, such that the handle 216 and surgical orientation device 12 generally move together.

The anatomical contact device 214 can further comprise an anatomical contact component 218. The anatomical contact component 218 can comprise an acetabular landmark contacting device, and can be releasably coupled to the alignment handle 216, or can be integrally formed with the alignment handle 216. In a preferred arrangement, the component 218 can comprise a tripod-like structure, with three arms 220 extending radially outwardly from a center portion 222 of the component 218. Each of the three arms 220 can be spaced radially equally from one another at 120 degrees, although other arrangements are also possible, as are other numbers of arms 220. Each of the arms 220 can further be angled such that no one plane contains any two of the arms 220. Each of the arms 220 can comprise a tip 224. As described further herein, the tips 224 can be used to contact landmarks on the acetabular rim of the patient.

D. Orthopedic System for Preparing an Acetabular Surface

Figure 5:
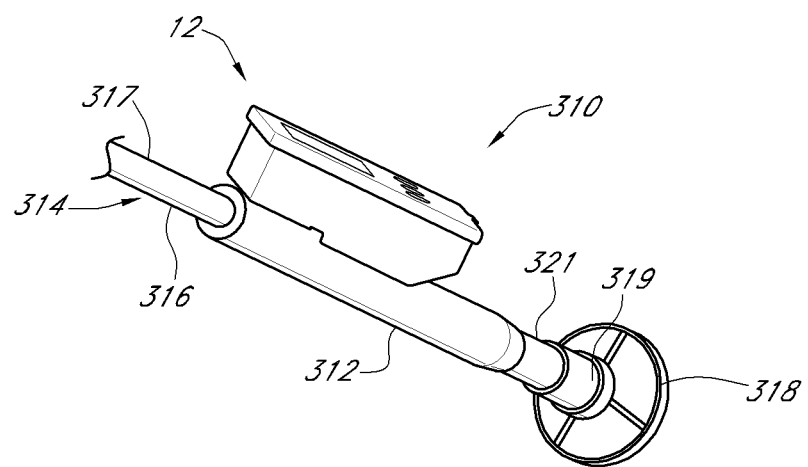
FIG. 5 is a perspective view of a orthopedic system according to one embodiment for preparing a portion of a patient's anatomy to receive an implant.

With reference to FIG. 5, an orthopedic system 310 can be used to prepare a portion of a patient's anatomy, such as for example an acetabular socket area in a patient's pelvis. The orthopedic system 310 can be used, for example, to ream at a specified angle or orientation relative to a reference and/or anatomical landmark. The orthopedic system 310 can comprise the surgical orientation device 12 described above, a protective mounting device 312, and a surface preparation tool 314.

1. Stationary Mount for the Surgical Orientation Device

With continued reference to FIG. 5, the mounting device 312 can comprise a structure which releasably attaches to the surgical orientation device 12 and allows the surgical orientation device 12 to generally remain still while reaming takes place. For example, the protective mounting device 312 can comprise an elongate tubular structure and/or bearing which permits relative rotational movement of a structure within its inner surfaces. The protective mounting device 312 can be made of plastic, metal, or other suitable material. The mounting device 312 can comprise lubricant applied to its inner surfaces, and/or can comprise a bearing or bearings which inhibit the mounting device 312 from rotating when reaming is taking place.

2. Acetabular Surface Preparation Device

With continued reference to FIG. 5, the surface preparation tool 314 can comprise a device which can prepare a portion of a patient's anatomy. For example, the surface preparation tool 314 can ream out a portion of a patient's acetabular socket. The surface preparation tool 314 can comprise a reamer handle 316. The reamer handle 316, or a portion of the reamer handle 316, can extend through the mounting device 312, and at least a portion of the reamer handle 316 can rotate relative to the mounting device 312 while at least a portion of the surface preparation tool 314 is rotating. In some embodiments, the reamer handle 316 can comprise a proximal end 317 that comprises a handle, a distal end 319, and a rotatable shaft portion 321 extending therebetween, the rotatable shaft portion 321 being rotatably coupled with the proximal end 317.

The surface preparation tool 314 can further comprise a surface preparation device 318. The surface preparation device 318 can be releasably coupled or integrally formed with the reamer handle 316, and can comprise a cutting tool or element which digs into and reams out bony matter and/or tissue in the patient's anatomy. For example, the surface preparation device 318 can comprise a generally spherical-shaped cutting tool which is configured to ream out an acetabular socket.

E. Orthopedic System for Orienting a Prosthetic Hip Component

Figure 6:
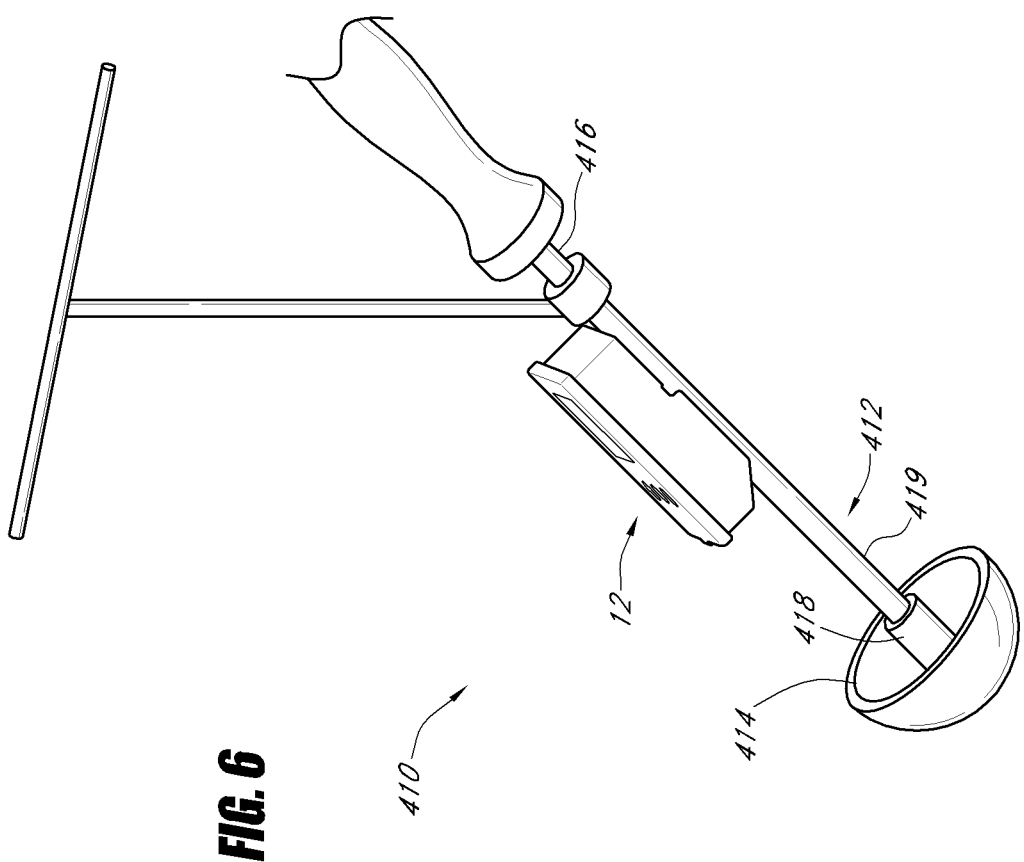
FIG. 6 is a perspective view of a orthopedic system according to one embodiment for orienting a prosthetic component.

With reference to FIG. 6, a orthopedic system 410 can be used to orient a prosthetic component, such as for example a prosthetic acetabular cup. The orthopedic system 410 can be used to orient the prosthetic component at a specified angle or orientation relative to a reference and/or anatomical landmark. The orthopedic system 410 can comprise, for example, the surgical orientation device 12 described above, a guide device 412, and a prosthetic component 414 (e.g. prosthetic acetabular cup).

1. Device for Guiding a Prosthetic Component

With continued reference to FIG. 6, the guide device 412 can comprise a proximal end 416, a distal end 418, and an elongate portion 419 extending therebetween. The proximal end 416 can comprise a handle that can be gripped by a user. The elongate portion 419 can comprise an elongate rod or structure which can be releasably coupled to the surgical orientation device 12, such that the guide device 412 and surgical orientation device 12 generally move together.

The distal end 418 can comprise a implant contacting structure which releasably couples the guide device 412 to the prosthetic component 414. While coupled, the prosthetic component 414 can move with the guide device 412. Once oriented, the prosthetic component 414 can be released from the guide device 412.

2. Prosthetic Component for Insertion in the Patient's Anatomy

The prosthetic component 414 can comprise any of a number of commonly available prosthetics, including but not limited to prosthetic acetabular cups. The acetabular cup size can vary depending upon the patient. The prosthetic component 414 can be sized and shaped so as to fit into the area reamed out by orthopedic system 310.

III. Hip Preparation Methods

A number of different hip preparation methods are discussed below. These methods can be used in conjunction with the systems described above, and are useful for modifying the natural hip joint to enable the hip joint to have a prosthetic component or components, such components including but not limited to a prosthetic acetabular cup.

A. Pre-Operative Planning

Prior to any hip procedure, a surgeon or other medical personnel can create templates of a patient's anatomy, and use these templates to determine ideal post-procedure conditions within the patient's anatomy. For example, in a hip replacement procedure, the surgeon can first obtain x-ray images of the patient's pelvis. Based on the images, the surgeon can look at a diseased side of the hip, as well as the healthy side, and determine goals for joint offset and leg length.

FIG. 29A illustrates a joint offset prior to incising the capsule joint in the hip. As illustrated in FIG. 29A, joint offset (represented for example by the arrows labeled "OS") generally represents a medial/lateral component of the distance between two landmarks, one of which is generally fixed. For example, during a hip replacement procedure utilizing one or more of the systems described above, the reference post 14 can remain fixed. Thus, joint offset can be represented by a distance "OS" between the fixed reference post 14 and a specified landmark "A" on the femur, taken in a generally medial/lateral direction.

Similarly, leg length can be represented by the arrows "LL" in FIG. 29A. With reference again to FIG. 29A, the leg length "LL" can be the component of the distance between the fixed reference post 14 and the specified landmark "A" on the femur, taken in a generally proximal/distal direction perpendicular to that of the medial/lateral direction.

When viewing the pre-operative x-rays, the surgeon can get an idea of what changes in joint offset and leg length will be necessary on the diseased side of the hip to bring the hip into symmetry (e.g. both sides of the hip having the same leg length and joint offset). If both sides of the hip are not brought into symmetry, the joint offset on the diseased side of the hip can cause wear and deterioration of the surrounding ligaments.

B. Establishing a Reference for Hip Replacement Using an Orthopedic System

Figure 13:
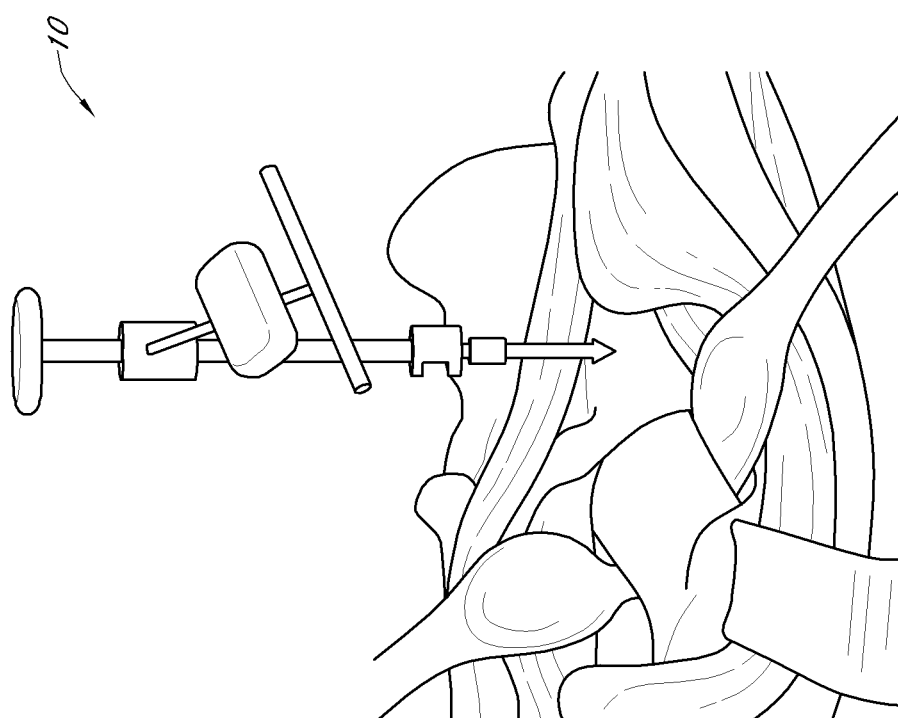
FIG. 13 illustrates a method in which the patient's hip is generally parallel to an operating table and a reference post of the orthopedic system of FIGS. 2A-C is inserted into the patient's anatomy.

With reference to FIG. 13, the orthopedic system 10 described above can be used to establish a reference in the patient's anatomy. The reference can be established prior to incising a joint capsule in the hip. For example, once the hip anatomy has been exposed by pulling back surrounding tissue, the reference post 14 can be driven into a specified landmark on the patient's anatomy. In one embodiment, such landmark remains immobile throughout the rest of a hip replacement procedure. Thus, a landmark such as the iliac spine can be used, although other landmarks are also possible. For example, in some embodiments, as discussed in greater detail below, the reference post 14 can be driven into a portion the femur, or other parts of the human anatomy. In some embodiments, the reference post 14 can be clamped and/or otherwise anchored to a portion of the femur, and the pelvis can be referenced relative to the femur.

Once a landmark is chosen, the surgeon can use a slap hammer or other device to pound the impactor 16 and drive the reference post 14 into the patient's anatomy as desired, until the reference post 14 is firmly in place. If the reference post 14 has a sensor 15 on or embedded within or otherwise coupled to the reference post 14, the sensor 15 can be at least partially within the bony mass of the pelvis (or other bony area), or can still be exterior of the anatomy after insertion of the reference post 14. In some embodiments, the reference post 14 can comprise a retractor. For example, with the surrounding tissue pulled back, the reference post 14 can be configured as an anchor or as a retractor to at least partially hold back the tissue that would normally be disposed above or around the surgical site.

With reference to FIGS. 2A and 13, prior to the hip replacement procedure, and prior to driving the reference post 14 into the iliac spine, the surgical orientation device 12 can be registered in a position parallel to the operating table and floor. For example, data about the orientation of the surgical orientation device 12 can be obtained through the sensor or sensors 50 in the surgical orientation device 12 while the surgical orientation device is held parallel to the operating table.

Once the surgical orientation device 12 is registered, and the reference post 14 has been driven into the iliac spine, the pelvis can be adjusted and moved relative to a fixed reference frame. Because the angle α described above and shown in FIG. 2A can remain fixed relative to the reference post 14, movement of the system 10 and surgical orientation device 12 can be monitored. For example, in some embodiments the surgical orientation device 12 can be positioned at a known angle, such as an acute angle (e.g. 45 degrees), relative to a medial-lateral plane of the pelvic bone. In some embodiments, the surgical orientation device 12 can be positioned at about 45 degrees relative to a longitudinal axis of the reference post 14. In some embodiments, the hip (with the reference post 14 inserted) can be adjusted until the surgical orientation device 12 indicates an angle 90°−α, at which point the reference post 14 is positioned generally perpendicular to the floor, and the patient's pelvis is positioned generally parallel to the floor. Such positioning of the pelvis can be helpful, for example, in proper positioning of the prosthetic component 414 described above. In some embodiments, the reference post 14 can be driven vertically into the iliac spine while the patient is in a supine position. A probe, such as for example a laser or mechanical rod, can be used to align the surgical orientation device 12 with an axis of the leg to establish a reference rotation about a vertical axis and a direction for leg length measurement(s).

As described above, the reference post 14 can contain a sensor or sensors 15 that evaluate the orientation (e.g. position or angle) of the pelvis or other bony area. For example, once the pelvis has been positioned generally parallel to the operating table and floor, the sensor or sensors 15 can be zeroed and/or registered by the surgical orientation device 12 or other device. In a preferred arrangement, the sensor 15 can communicate with the surgical orientation device 12, giving the surgical orientation device 12 information about the orientation of the iliac spine and/or pelvis. If the pelvis moves during the hip procedure, the surgical orientation device 12 can account for such movement since it has information about such movement from sensor 15. Furthermore, the surgical orientation device 12 can additionally obtain information about the spatial location of the reference post 14 based on the sensor or sensors 15, and can use that information to obtain and record measurements of distance between the reference post 14 and surgical orientation device 12. In some embodiments, the sensor 15 can comprise a satellite sensor which communicates with the surgical orientation device 12, and is separately read by the surgical orientation device 12. In some embodiments, the surgical orientation device 12 and reference post 14 can each comprise a sensor or sensors. In some embodiments the surgical orientation device 12 can be configured to only receive information from the sensor 15, and does not itself have an orientation sensor. Furthermore, in some embodiments, more than one sensor can be used. For example, the systems described herein can comprise two or more sensors 15 located on the pelvis, greater trochanter, and/or other anatomical landmarks.

In one embodiment, a first satellite sensor is the sensor 15 coupled with the reference post 14, a second satellite sensor is coupled with another surgical device, and both satellite sensors provide sensor data to a variation of the surgical orientation device 12. Where two satellite sensors are provided, one can be coupled with a first bone adjacent to a joint and a second can be coupled with a second bone adjacent to a joint. With two satellite sensors, the position, orientation, or movement of these bones and the joint to which they are adjacent can be monitored.

With the reference post 14 thus positioned, the impactor 16, angle assessment guide 18, and surgical orientation device 12 can be removed, leaving only the reference post 14 behind. The reference post 14 can then serve as a reference as described above, and can be used as an anchoring point for attachment of the orthopedic system 110.

FIGS. 13A and 13B show a technique in which the reference post 14 can be coupled with the patient's anatomy without being attached to any bony structure. Rather, as shown in these figures, a fixture 510 is provided for indirectly coupling the reference post 14 to the patient's anatomy. Although shown as providing for indirect coupling with a femur, the fixture 510 can be configured for attachment to other anatomy such that the reference post 14 does not need to be directly connected to bony structure. This arrangement is useful where the clinician prefers not to disrupt the bony structure, such as where the bony structure is delicate or would be unduly weakened by such interaction.

In one embodiment, the fixture 510 includes a bone engagement portion 514 that is configured to engage the bone in a static manner. For example, the bone engagement portion 514 can comprise a clamping structure that generates sufficient normal force to provide secure frictional engagement with the femur or other anatomy. In some embodiments, the clamping structure is spring loaded or includes a ratchet design to allow for quick attachment with sufficient force for immobilizing the fixture 510.

The fixture 510 preferably also is configured to securely receive the reference post 14. For example, a mounting structure 518 can be coupled with the bone engagement portion 514 and disposed laterally. The bone engagement portion 514 provides a surface area into which the reference post 14 can be driven using a slap hammer or other device for transmitting a force to the distal end of the reference post 14. For example, the impactor 16 can be coupled with the reference post 14, as described herein, prior to driving the distal end of the reference post 14 into the mounting structure 518. In other techniques, the distal end of the reference post 14 can be coupled with the mounting structure 518 by clamping or other techniques that do not require applying a driving force, as with a slap hammer.

In the technique of FIGS. 13A, 13B, and 14A, the other orthopedic systems described herein can be used during further aspects of procedures. For example, the angle assessment guide 18 can be used with the surgical orientation device 12 in applying the reference post 14. This technique can be used in placing the reference post 14 when the femur is positioned parallel to a surgical table. In some techniques, the femur is placed such that it is disposed generally perpendicular to the direction of gravity prior to placement of the reference post 14, as shown in FIG. 13B.

FIG. 14A illustrates that after the reference post 14 has been placed, the measuring device 112 can be used to acquire information about the location of one or more anatomical landmarks. For example, the measuring device 112 can be used to locate a probe (e.g., a laser or mechanical probe or rod) above a landmark on the hip while the reference post 14 is coupled with the femur. In particular, the measuring device 112 can be coupled with the reference post to provide for multiple degrees of freedom. For example, the measuring device 112 can be pivoted about a longitudinal axis of the reference post 14. In some embodiments, the measuring device 112 is also tiltable about a second axis that is disposed generally perpendicular to the longitudinal axis of the reference post 14, as described in connection with FIGS. 3A and 3B. Such tilting may facilitate engagement with a wide variety of anatomical landmarks on the hip by the marking device 118.

C. Measuring Joint Distances Using an Orthopedic System

Figure 14:
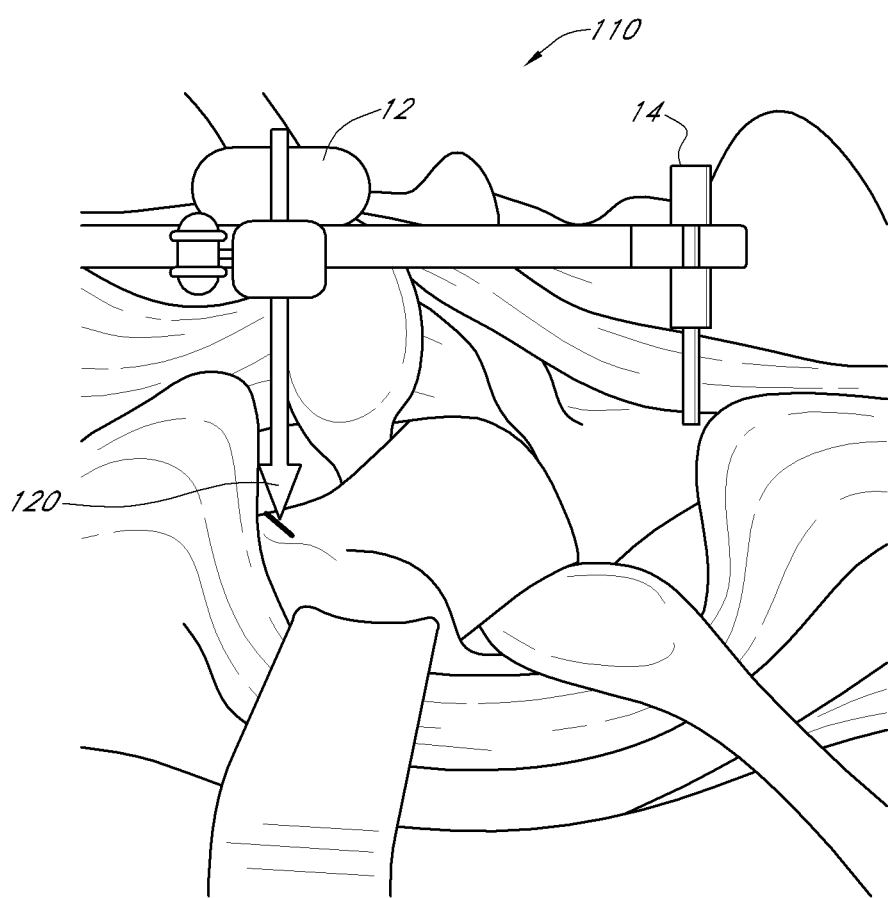
FIG. 14 illustrates a method in which the orthopedic system of FIGS. 3A-B is being used to measure a distance between the fixed reference post and a reference location on the patient's anatomy.
Figure 15:
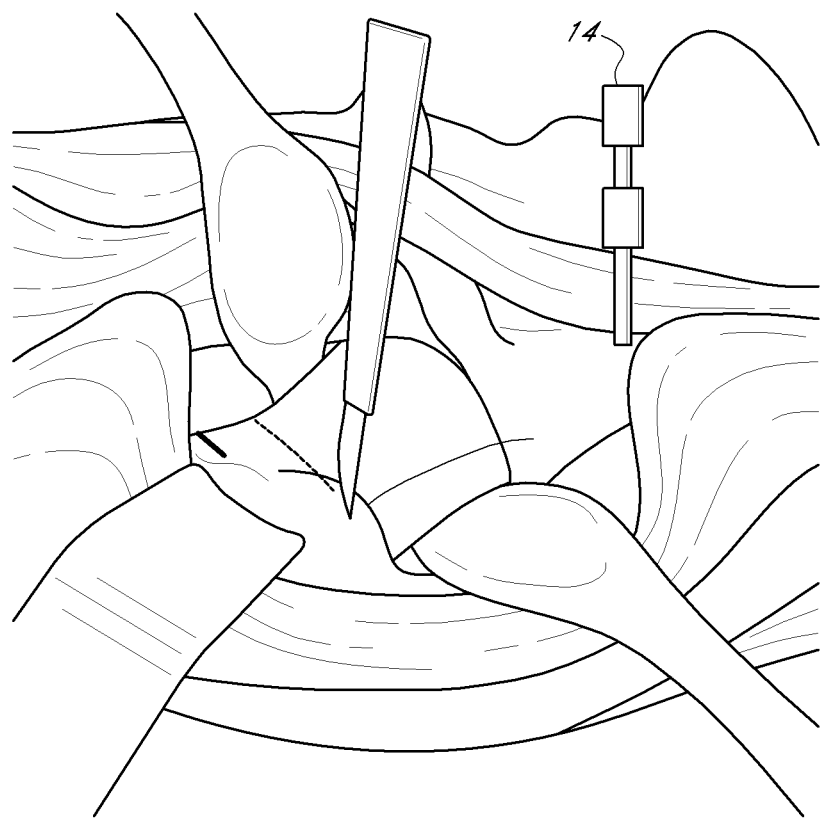
FIG. 15-18 illustrate techniques for resecting a femoral head and cleaning of osteophytes around the acetabular rim.
Figure 16:
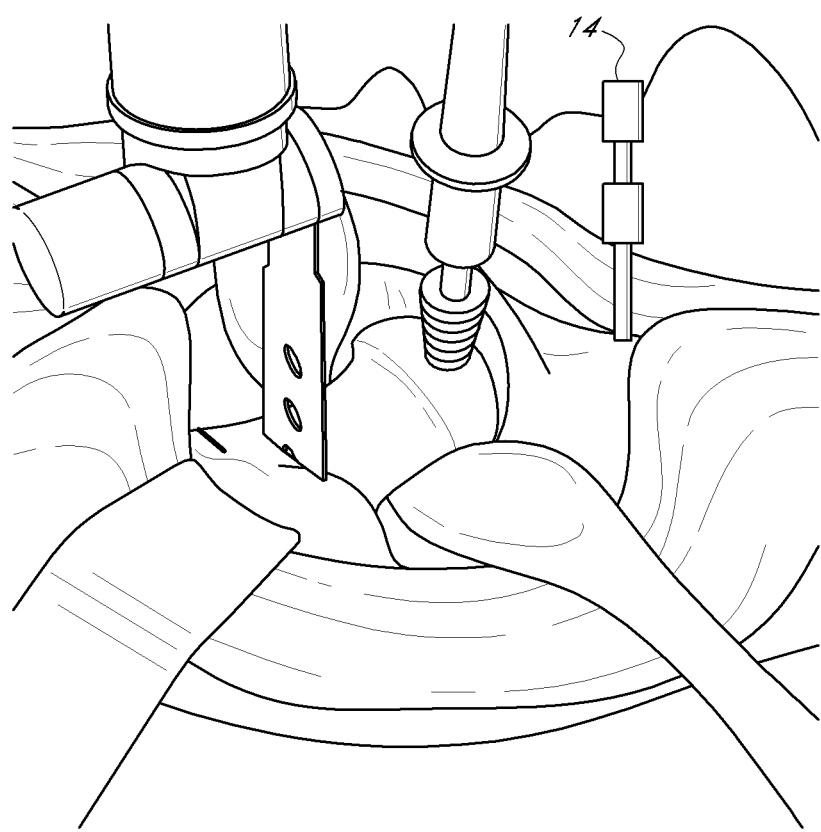
Figure 17:
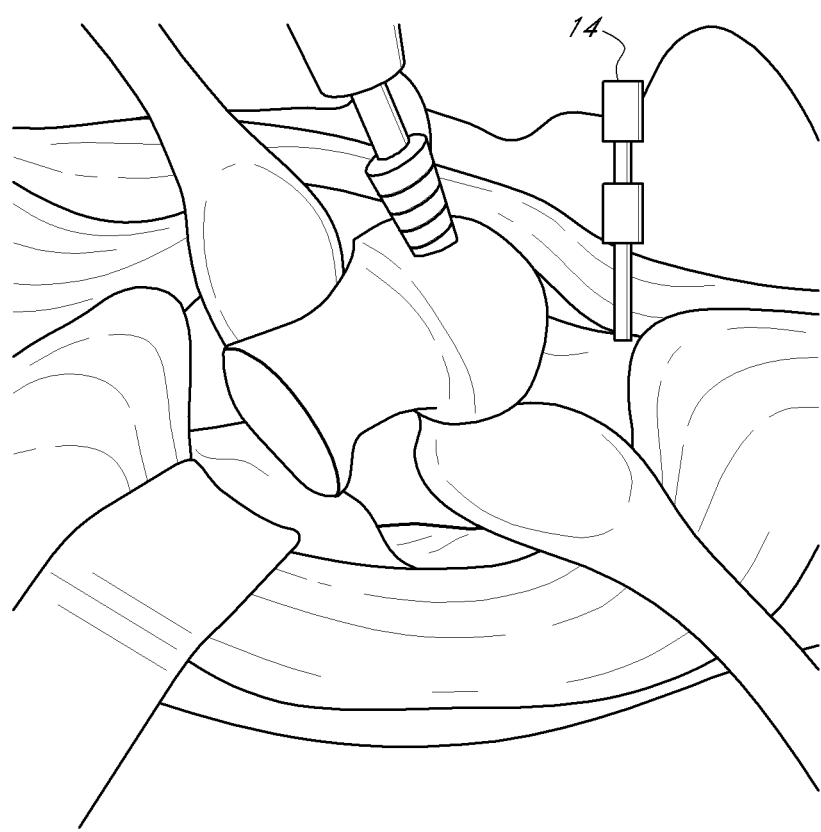
Figure 18:
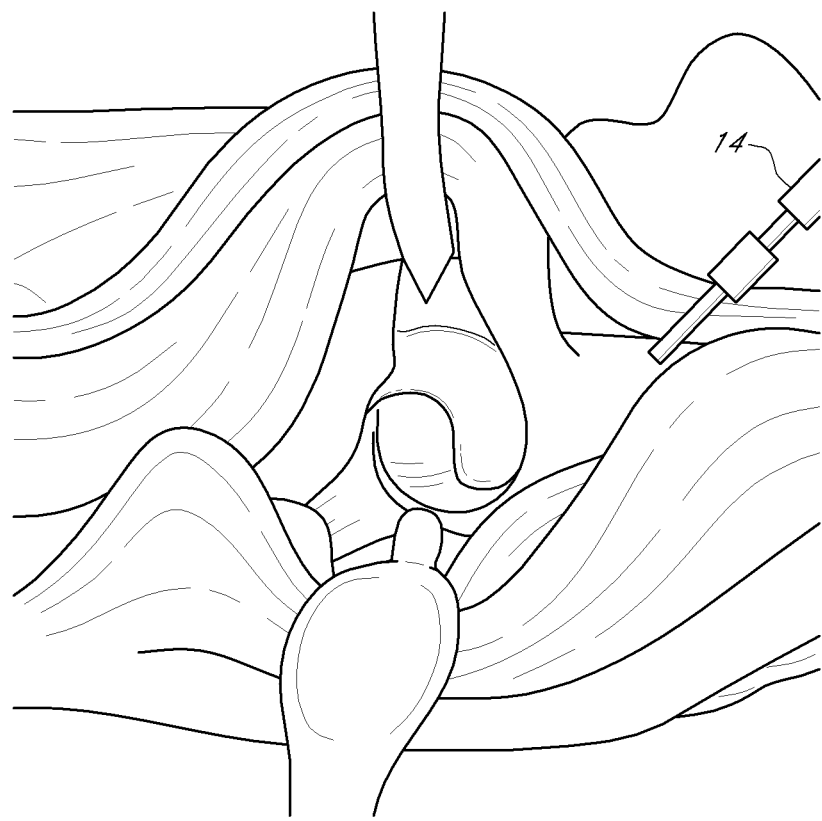

With reference to FIGS. 3A-B and 14, prior to incising the joint capsule, the orthopedic system 110 can be used to measure at least one distance in the hip joint area. For example, the attachment structure 116 of the measuring device 112 can be releasably coupled to the surgical orientation device 12, and the measuring device 112 can be coupled to the fixed reference post 14. The measuring device 112 can be aligned with the axis of the leg so that measuring device 112 measures the leg-length component. The user can slide surgical orientation device 12 and/or marking device 118 along the measuring device 112 until the end 120 of the marking device 118 is contacting a selected location or locations on the femur (e.g., the superior aspect of the lesser trochanter), which location can then be marked with a suitable biocompatible marker or other marking agent. The surgical orientation device 12, in a linear measurement mode, can then be zeroed, and can record a distance between the fixed reference post 14 and the anatomical landmark or landmarks. In a preferred arrangement, the measurement of distance between the reference post 14 and marked location on the anatomical landmark can be obtained via communication between the surgical orientation device 12 and the sensor 15 in reference post 14. The marking or markings 114 can provide an additional indication, of the measured distance.

The surgical orientation device 12 can have two linear measurement components, one which responds to leg length and one which responds to offset. While the lesser trochanter is described in terms of an anatomical landmark, a different anatomical landmark or landmarks can be used instead, including but not limited to the greater trochanter. In another embodiment, a satellite tiltmeter can be attached to the femur on a location such as the greater trochanter which allows the angle of the femur to be zeroed and later reproduced when these measurements are repeated at the trial reduction phase. This can eliminate small errors in leg-length and offset which can be caused movement of the femur. If attached to the greater trochanter, this could be designed so that it is not in the way during the procedure.

The distance between the reference post 14 and the superior aspect of the lesser trochanter can be correlated, or related to, anatomical distances such as leg length and joint offset as described above. For example, and as described above, such distance can be assessed by the medical provider in a pre-operative x-ray assessment. With reference to again to FIG. 29A, end points of lines connecting the references points described above can roughly correspond to a hypotenuse indicative of an anatomical distance, such that zeroing the surgical orientation device 12 can result in the surgical orientation device registering this first anatomical distance or distances as a reference distance(s). As used herein "zeroing" is not limited by setting the SOD display to read "0", but also includes, for example, recording a position in three dimensional space relative to a selected reference frame.

D. Determining the Orientation of an Anatomical Plane Using an Orthopedic System With reference to FIGS. 15-18, once the orthopedic system 110 has been used to measure a first reference distance or distances, the components of the system 110 other than the reference post 14 can be removed. The joint capsule can then be incised, and the proximal femur can be removed. Once the proximal femur is removed, osteophytes surrounding the acetabular rim of the patient can also be removed according to known procedures.

Figure 19:
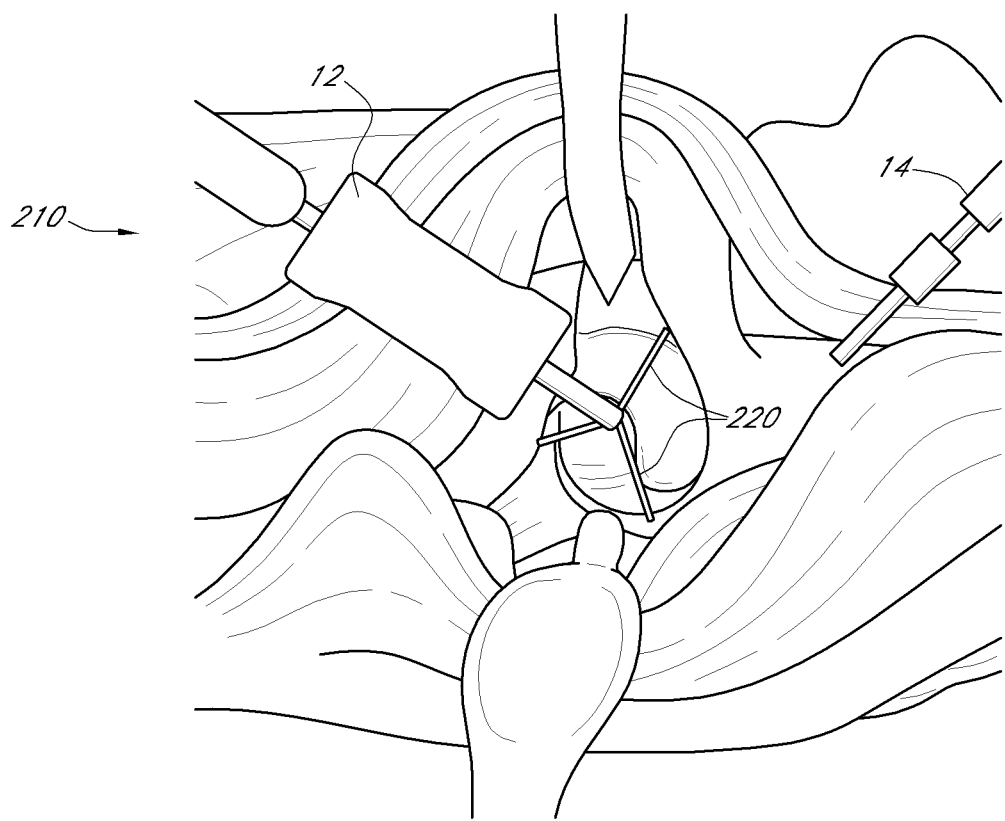
FIG. 19 is a perspective view of the orthopedic system of FIG. 4 being used to determine the orientation of a plane defined by landmarks on the patient's acetabular rim.

With reference to FIGS. 4 and 19, the orthopedic system 210 can be used to determine the orientation of an anatomical plane in the patient. For example, once the joint capsule has been incised and osteophytes have been removed, the alignment handle 216 can be releasably coupled to the surgical orientation device 12. The alignment handle 216 can then be gripped by the surgeon, and the anatomical contact component 218 can be moved into contact with the acetabular rim. For example, the tripod-like structure with arms 220, as shown in FIGS. 4 and 19, can be placed against the acetabular rim, and the tips 224 of the contact component 218 can contact three landmarks on the acetabular rim. These three landmarks can be determined by the surgeon or other user. Once three landmarks have been contacted, the contact component 218 can be referencing a plane extending across the acetabular rim. At this point, the surgeon can register the orientation of this plane with the surgical orientation device 12. In some embodiments, a planar laser can project a line onto the pelvis of the patient. The surgeon can make a mark somewhere on this line which can be referenced in later steps. This can serve the purpose of establishing a reference rotational position of the orthopedic system about a vertical line. If rotation about a vertical axis is not constrained in some form, then there can be an infinite number of orientations that satisfy a tiltmeter reading, since their locus can form a cone. Also, the surgical orientation device 12 can incorporate the orientation of the reference pin 14 in its calculations so that the surgical orientation device 12 can compensate for any subsequent movement of the pelvis.

In some embodiments, and as described herein, the surgical orientation device 12 can include a light indicator, such as a laser or lasers. The lasers can be emitted from optical components 42 of the surgical orientation device. Thus, in some embodiments of the orthopedic system 110, the surgical orientation device, or other component, can emit a laser or lasers towards a landmark or landmarks in order to obtain an orientation of the acetabular rim. For example, the lasers can be emitted from the surgical orientation device such that they pinpoint an area or areas along the acetabular rim, and provide an indication to the surgical orientation device 12 of the orientation of a plane extending across the rim. In other embodiments, different landmarks can be used.

E. Preparing a Portion of the Patient's Anatomy Using an Orthopedic System

Figure 20:
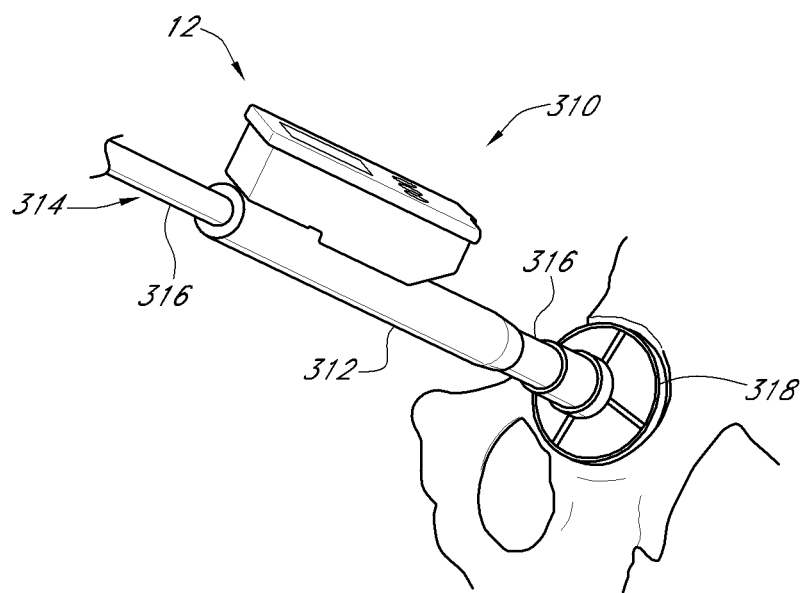
FIG. 20 is a perspective view of the orthopedic system of FIG. 5 being used to ream out a portion or portions of the patient's acetabular socket.

With reference to FIGS. 5 and 20, the orthopedic system 310 can be used to prepare a portion of the patient's anatomy. For example, the orthopedic system 310 can be used to ream out an acetabular socket at a defined angle and/or orientation.

Once the orthopedic system 210 has established a reference plane, such as for example the plane defined by the three reference landmarks on the acetabular rim, the reamer 318 can be moved into the area bounded by the acetabular rim. The surgeon can hold the reamer handle 316, and the reamer 318 and/or a portion or portions of the reamer handle 316 can spin and rotate. As the reamer 318 spins and digs into the bony area in the acetabulum, the surgical orientation device 12 can remain generally still while coupled to the mounting device 312. The surgeon can use the surgical orientation device 12 to monitor the orientation of the reamer 318. Thus, the surgeon can ream at a defined angle relative to the aforementioned reference plane, with the surgical orientation device 12 providing an indication or indications on its display as to whether the reamer 318 is reaming perpendicular to such plane, or at an some angle relative to the plane. In some embodiments, the surgeon can choose an appropriate angle based on pre-operative templates and/or a desired range of angles and movement for the implant 414.

F. Orienting a Prosthetic Component Using an Orthopedic System

Figure 21:
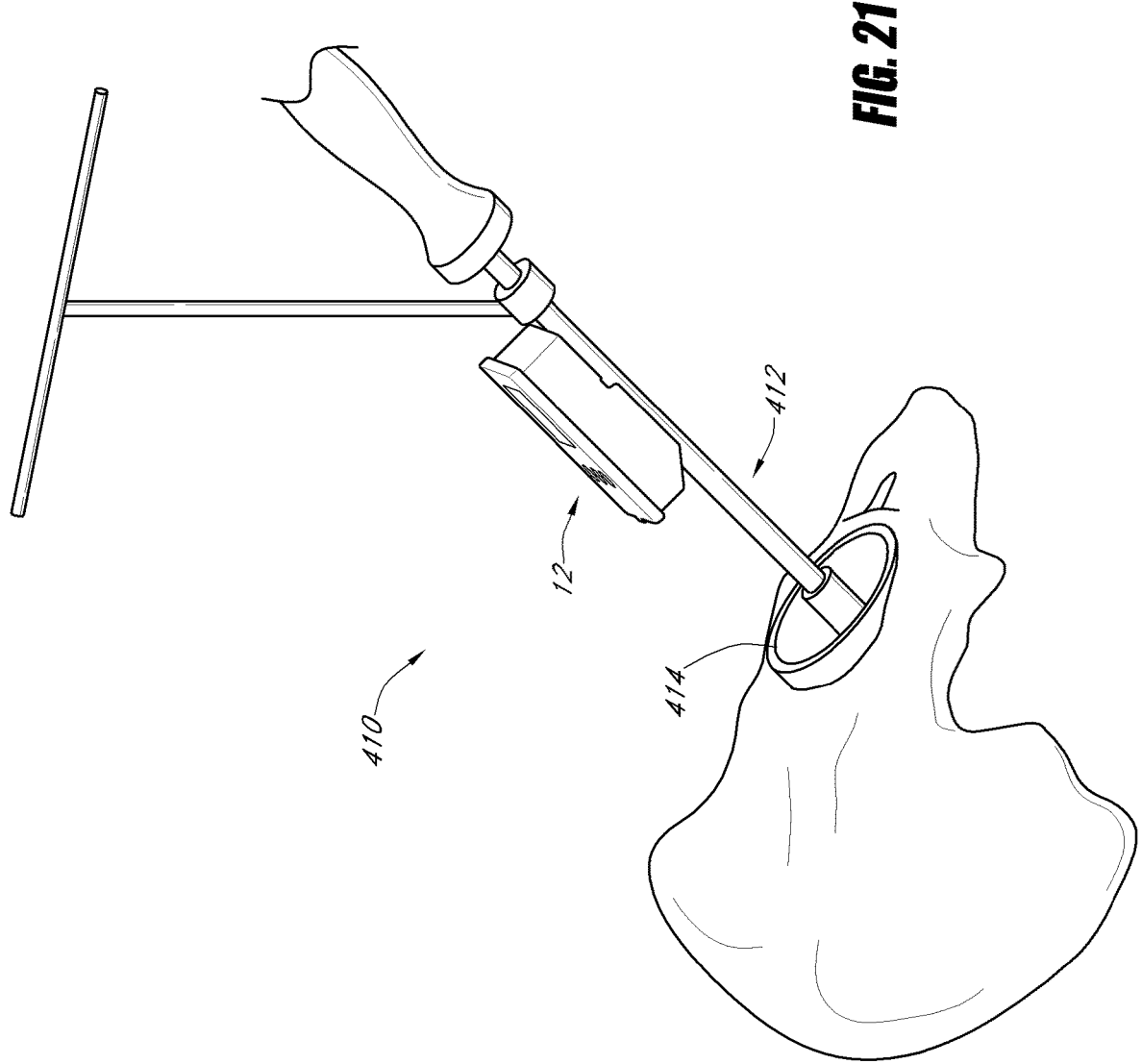
FIGS. 21 and 22 are perspective views of the orthopedic system of FIG. 6 being used to orient a prosthetic acetabular cup.

With reference to FIGS. 6 and 21, the orthopedic system 410 can be used to orient a prosthetic component, such as for example a prosthetic acetabular cup. For example, the orthopedic system 410 can be used to orient a prosthetic component 414.

Once the orthopedic system 310 has been used to ream out an acetabular socket, the orthopedic system 410 can be assembled. For example, the surgical orientation device 12 can be releasably coupled to the handle 416, and a prosthetic component 414 can be releasably coupled to the handle 416. The surgeon can then hold onto the handle 416 and move the prosthetic component 414 (e.g. prosthetic acetabular cup) towards the reamed out acetabular socket. The surgical orientation device 12 can be used to monitor the orientation of the prosthetic component 414 as it is moved and adjusted within the acetabulum. One can use a laser line (or other probe, such as for example a mechanical probe) to illuminate or otherwise reference a mark made earlier to control the rotation of the surgical orientation device 12 about a vertical axis. One can also use the orientation of the reference post 14 to compensate for movement of the pelvis. Once the prosthetic component 414 is positioned as desired (e.g. based on a pre-operative determination), the handle 416 and surgical orientation device 12 can be removed.

Figure 22:
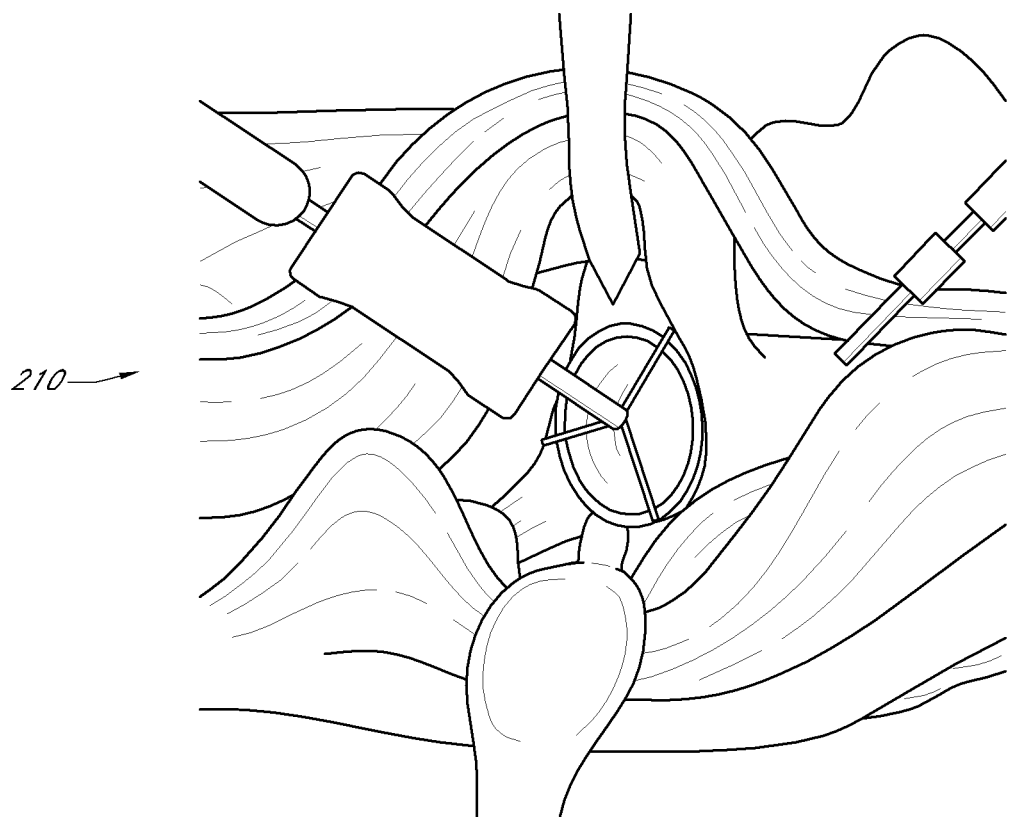
Figure 23:
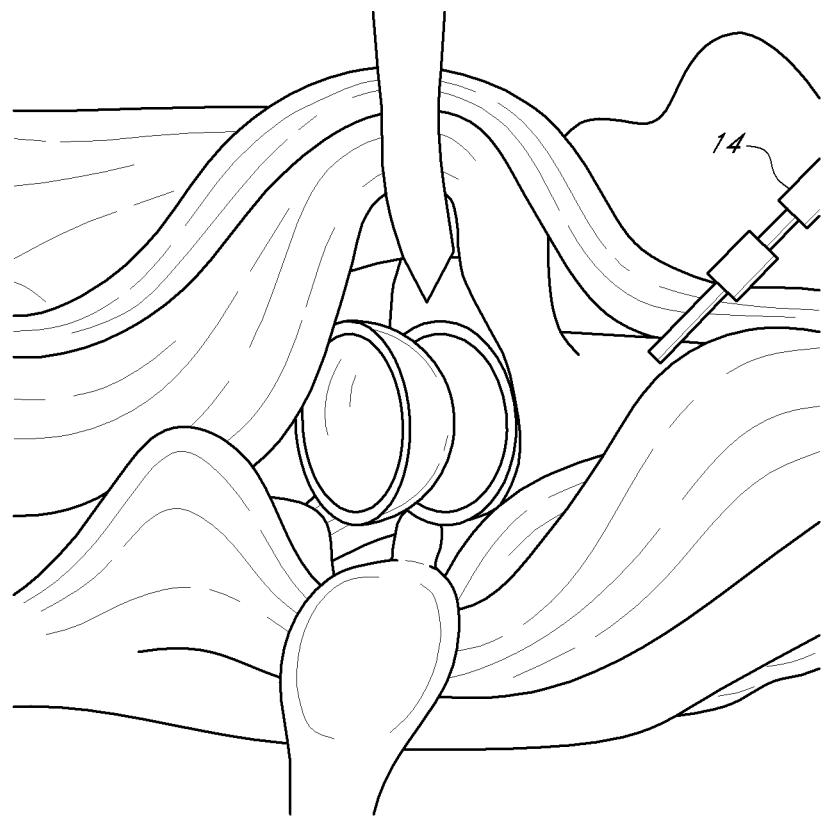
FIG. 23 is a perspective view of a polymer insert being placed in the prosthetic acetabular cup.
Figure 24:
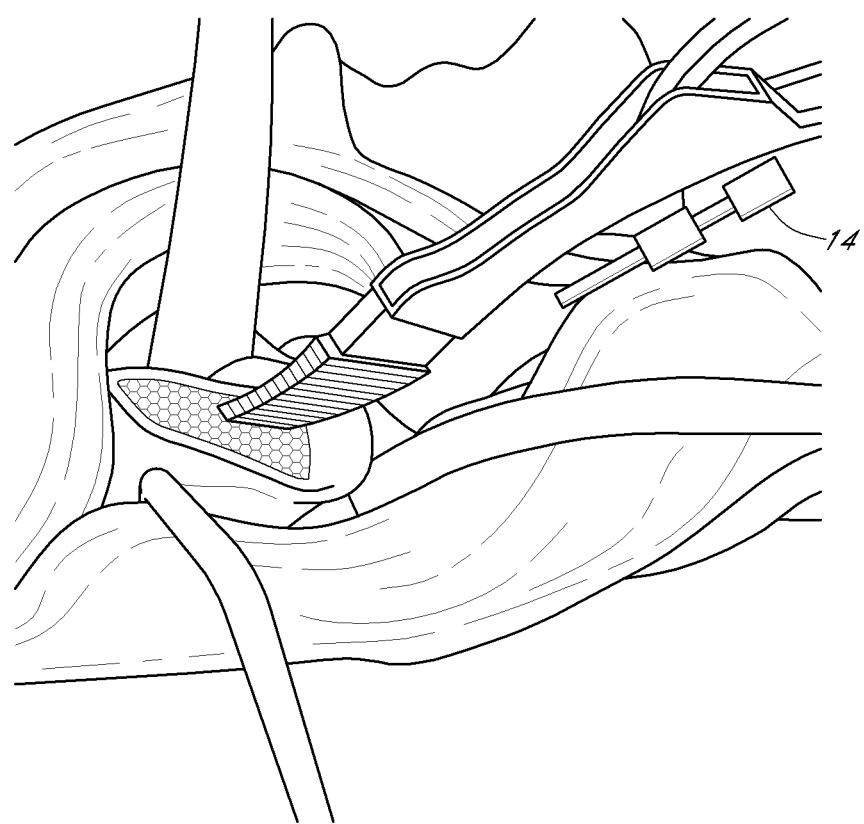
FIGS. 24-26 are perspective views of a preparation of femoral canal, broach, and prosthetic femoral head.
Figure 25:
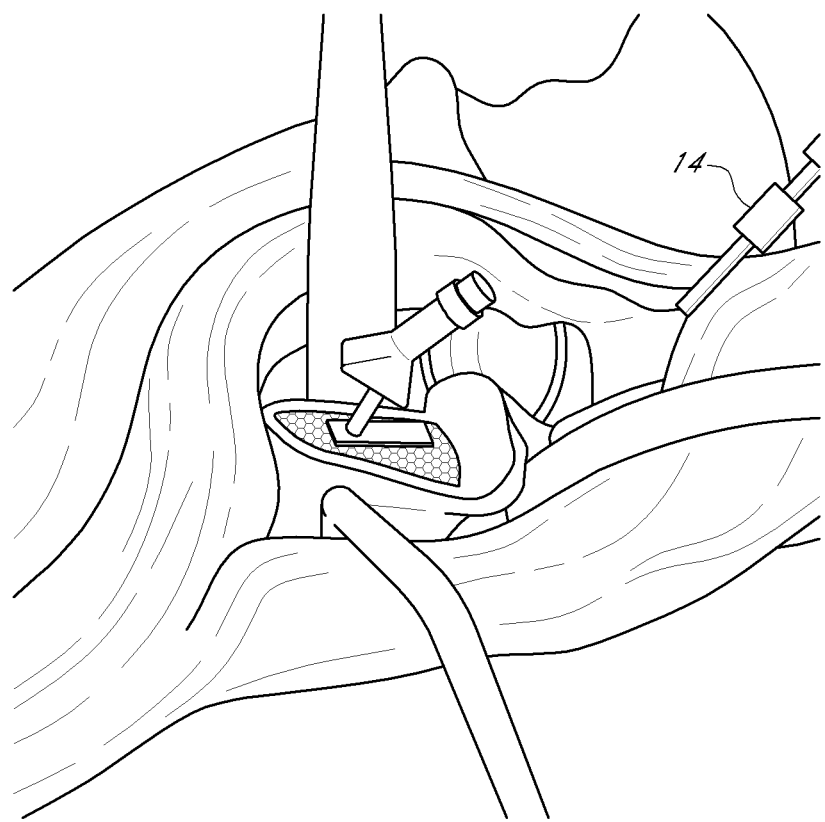
Figure 26:
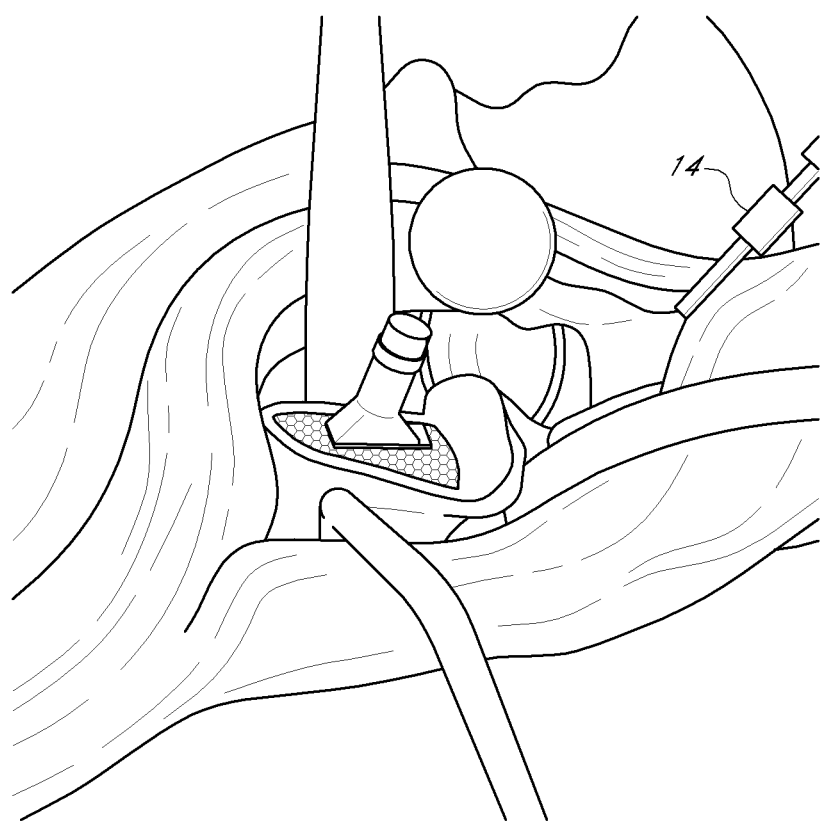
Figure 27:
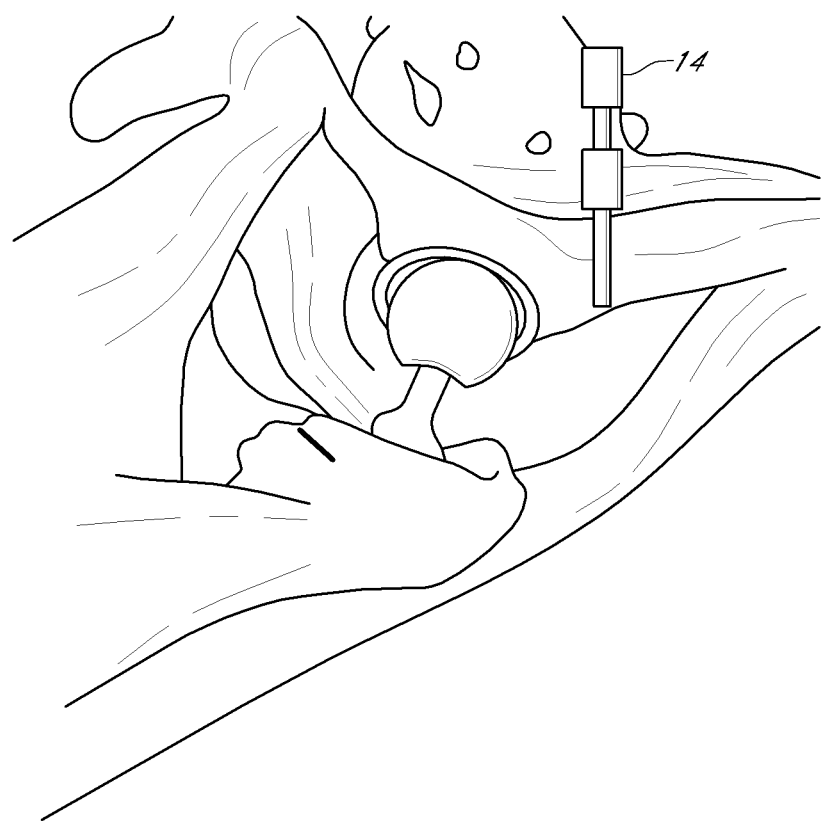
FIG. 27 is a perspective view of the patient's hip joint being reduced back into place, with the prosthetic femoral head inserted into the prosthetic acetabular cup.

In some embodiments, the orthopedic system 210 can then be used again to assess the orientation of the prosthetic component, as illustrated in FIG. 22. The anatomical contact component 218 can be placed against the prosthetic component 414, and the surgical orientation device 12 can indicate whether the prosthetic component 414 is oriented in the same plane as that previously registered by the surgical orientation device, or whether there is some angular offset or offsets. For example, the surgical orientation device 12 can indicate the prosthetic component 414 is tilted at a five degree angle in one frame of reference relative to the orientation of the reference plane previously registered by the surgical orientation device and orthopedic system 210. As described above, such an offset may be advantageous or desired, depending on how the surgeon wishes to orient the prosthetic. The system 210 can allow the prosthetic component 414 to be aligned with the rim of the acetabulum as described above, or relative to the plane of the pelvis, whichever is preferred. In the latter case it can be unnecessary to register the rim of the acetabulum.

G. Measuring Joint Distances Again Using an Orthopedic System

With reference to FIGS. 24-27, once a prosthetic component 414 has been positioned, joint distance(s) can be measured again. For example, once the prosthetic acetabular cup has been positioned, a femoral canal can be formed, and a prosthetic femoral broach and head can be coupled to the femur. Once the broach and head are coupled, the hip joint can be reduced and put back in place, with the prosthetic femoral head resting inside the prosthetic cup (e.g. prosthetic component 414).

Figure 28:
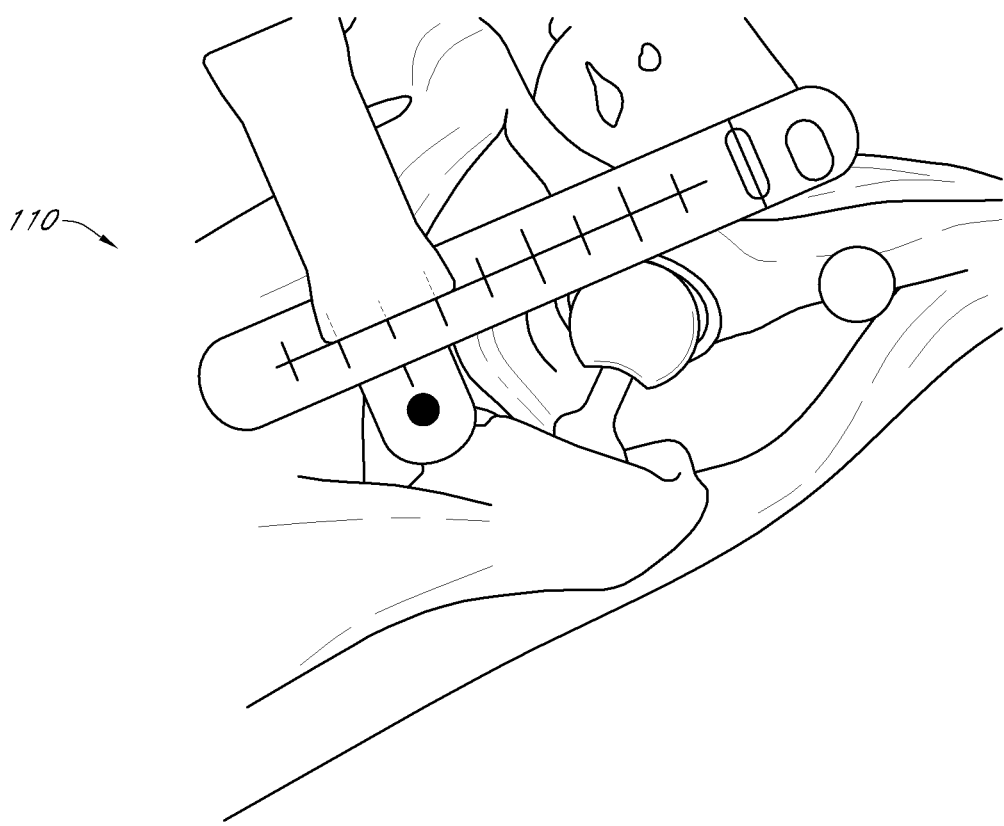
FIG. 28 is a perspective view of the orthopedic system of FIGS. 3A-B being used again to measure a distance between the fixed reference post and a reference location on the patient's anatomy.

With reference to FIG. 28, once the hip joint is reduced, the orthopedic system 110 can again be used to measure a distance from the fixed reference post 14 to an anatomical landmark (e.g. the same marked location on the superior aspect of the lesser trochanter).

With reference to FIG. 29B, this second reading can be compared with the first reading (e.g. the reading shown in FIG. 29A). Thus, a measurement or measurements can be taken both prior to joint capsule incision and after joint reduction to determine whether there has been any change in joint offset "OS" and leg length "LL" in the patient's anatomy. If the measurements are satisfactory for the surgeon, the prosthetic implant can be left in. If not, the surgeon can remove the implant 414 and/or adjust the implant 414 using one or more of the systems described above, until desired measurements are obtained. In some embodiments the surgical orientation device 12 can be programmed with a database of geometries of prosthetic components. The surgeon can input the configuration of components used in trial reduction plus his goals for adjusting offset and leg-length. The surgical orientation device 12 can then perform calculations based on three-dimensional geometry to determine a combination of components which should achieve his goals and recommend them to the surgeon. This can take much of the trial and error out of the process.

IV. Additional Sensors for Relative Movement

While the embodiments of the orthopedic systems and methods described above are described as having and using a sensor or sensors 50 located within the surgical orientation device 12, in some embodiments the orthopedic systems or other systems used for joint replacement can include an additional sensor or sensors 50 or 15. For example, and as described above, the reference post 14 can include a sensor 15. These additional sensors can be located on other surgical components and/or anatomical landmarks. U.S. Pat. No. 7,559,931 discloses examples of sensors on multiple surgical components and/or anatomical landmarks, and is herein expressly incorporated by reference in its entirety. In some embodiments, the orthopedic systems can include an additional sensor or sensors on the femur, hip, or other anatomical locations. The additional sensor can include a microcontroller and/or communication device (e.g. infrared or other wireless technology (e.g. Bluetooth™)) which can relay information from the additional sensor to the electronic control unit 1102 of the surgical orientation device 12. This additional sensor or sensors can detect changes in movement of the patient's anatomy during an orthopedic procedure, so as to verify whether the patient's anatomy has moved or changed position during the procedure. In some embodiments, the sensor or sensors described herein (e.g. sensor 15) can be part of a variable capacitance system similar to that used in digital calipers.

The electronic control unit 1102 can be configured to receive the information from this additional sensor or sensors, and/or the sensor's communications device, and combine that information with information from the sensor or sensors 50 located within the surgical orientation device 12 to calculate an overall, or aggregate, movement and orientation of the surgical orientation device 12 relative to, for example, an axial line or plane. The electronic control unit 1102 can correct for changes in position of the surgical orientation device 12.

Additionally, the additional sensor or sensors can be located in a device. The device can be constructed such that the device is autoclavable and reusable, and can allow insertion and removal of a disposable battery. The additional sensor or sensors can be incorporated with any of the systems and/or methods described herein, and can be placed on any of the components of the systems described herein.

V. User Interfaces

The systems and methods described above can each incorporate the use of a measuring device, such as for example the surgical orientation device 12. As described above, the surgical orientation device 12 can comprise at least one user input, a display and an electronic control unit. The user inputs and display, and/or the combination of the inputs, display, and electronic control unit can together form part of an interactive user interface. For example, the interactive user interface can comprise a housing (e.g., housing 30 described above), a coupling member formed on or within the housing configured to removably couple the user interface to an orthopedic device (e.g., handle 416), a sensor (e.g., sensor 50 described above), an electronic control unit (e.g., electronic control unit 1102 described above), a user input (e.g., user input 36 described above, which can transmit input commands to the electronic control unit), and a display (e.g., display 34 described above).

The interactive user interface can comprise a graphical user interface having an interactive window displaying on-screen graphics. For example, the interactive user interface can provide the user with a plurality of screen displays. The screen displays can illustrate the steps to be performed in a surgical procedure and can guide the user through the performance of the steps. Each screen display can comprise one or more on-screen graphics. The on-screen graphics can comprise one or more visual cues or indicators to prompt the user as to what step or steps to take next during one of the procedural methods described above. The visual cues referenced herein can comprise instructive images, diagrams, pictoral representations, icons, animations, visual cues, charts, numerical readings, measurements, textual instructions, warnings (visual and/or audible), or other data. The interactive user interface can be configured to alter attributes (e.g., color) of the on-screen graphics according to one or more data protocols. The interactive user interface can provide visual feedback to the user during performance of one or more surgical procedures. In certain embodiments, the interactive user interface can be configured to generate graphical user interface ("GUI") images to be displayed to the user. As described above, the user can interact with the surgical orientation device 12 via one or more user input devices 1114 (e.g., buttons, switches, touchscreen displays, scroll wheel, track ball, keyboard, remote controls, a microphone in conjunction with speech recognition software). The interactive user interface further can allow the user to confirm that a step has been completed (for example, by pressing a user input button). The interactive user interface can allow the user to enter data (e.g., a numerical value, such as a distance, an angle, and/or the like), verify a position of the surgical orientation device 12, turn a visible alignment indication system on and off, and/or turn the entire surgical orientation device on and off. In certain embodiments, the interactive user interface provides one or more drop-down lists or menus from which a user can make selections. For example, the user can make selections from a drop-down list using a scroll wheel, trackball, and/or a series of button presses. In some embodiments, the user interface provides a drop-down list of predicates that dynamically updates based on user input.

In at least one embodiment, a module for creating an interactive user interface can comprise a computer readable medium having computer readable program code embodied therein. The computer readable program code can comprise a computer readable program code configured to display one or more of a plurality of GUI images on a user interface of a surgical orientation device, the GUI images comprising instructive images related to the performance of a surgical procedure. The computer readable program code can be configured to receive instructions from a user identifying the surgical procedure to be performed (e.g., which joint and/or right or left). The computer readable program code can be configured to show the user steps to be performed in the identified process for the identified surgical procedure. The computer readable program code can be configured to guide the user in performance of the steps. For example, the computer readable program code can be configured to receive from the user an instruction to continue to the next step in the procedure, to receive orientation data from a sensor mounted within the surgical orientation device, and to display the orientation data on the user interface of the surgical orientation device.

In at least one embodiment, the surgical orientation device 12 described above can comprise a display module configured to display information and a sensor module configured to monitor the orientation of the surgical orientation device 12 in a three-dimensional coordinate reference system, and to generate orientation data corresponding to the monitored orientation of the surgical orientation device. The surgical orientation device 12 can further comprise a control module configured to receive the orientation data from the sensor module and convert it to objective signals for presentation on the display module, the control module also configured to display a set of GUI images or other on-screen graphics on the display module, the GUI images or on-screen graphics representing the orientation data received from the sensor module and also representing instructive images related to the performance of the joint replacement surgery.

In at least one embodiment, the surgical orientation device 12 can receive orientation data from a sensor module, receive input commands from a user input module to store orientation data from a user input module, convert the orientation data to a human readable format for presentation on a display device, and display on the display device on-screen graphics or GUI images for communicating information to a user based on the input commands and the orientation data, the information comprising instructive images for performing a joint replacement surgery and one or more visual indicators of a current orientation of the display device with respect to a fiducial, or reference, orientation.

In at least one embodiment, the surgical orientation device 12 described herein can comprise a sensor module coupled to an alignment jig and configured to measure and record a fiducial orientation and to continuously collect orientation data of the surgical orientation device, a display module configured to display at least one visual indicator of the orientation of the surgical orientation device with respect to the fiducial, or reference, orientation, the display module further configured to display instructive images of one or more steps to be performed by the surgeon during the joint replacement surgery, and a control module configured to receive the orientation data and to convert the orientation data to objective signals for presentation on the display module.

Figure 30A:
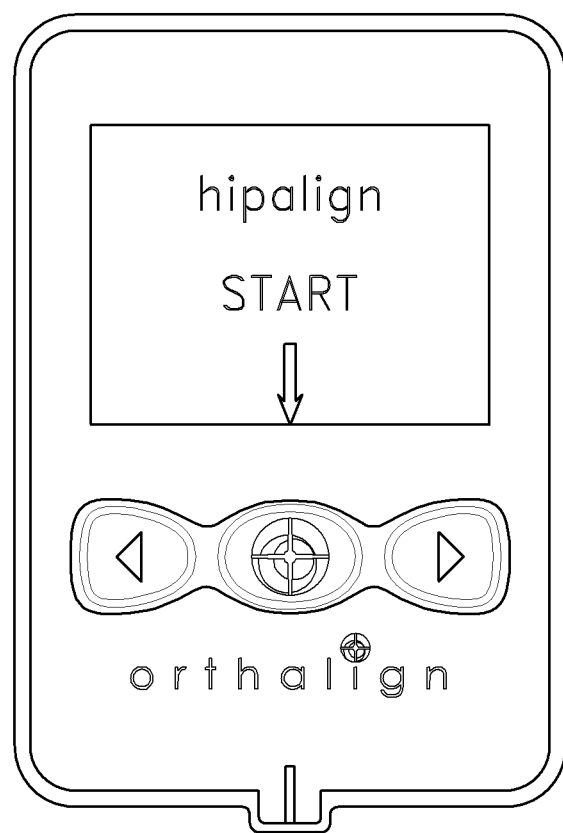
FIGS. 30A-W show various embodiments of user interface screens that can be displayed during an orthopedic procedure or procedures.
Figure 30D:
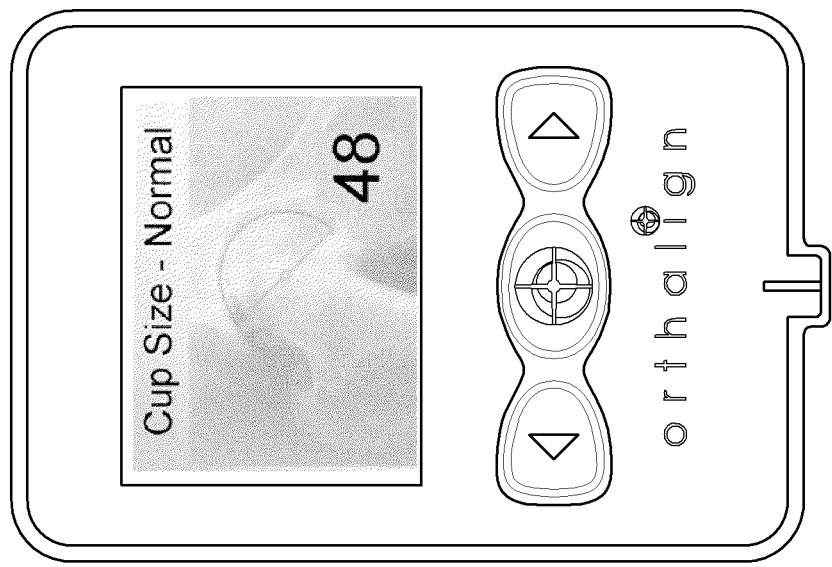
Figure 30C:
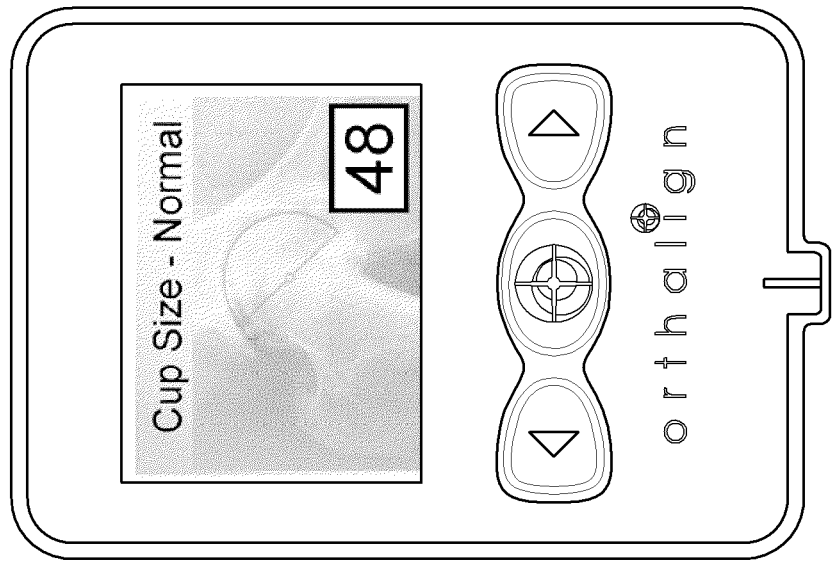
Figure 30B:
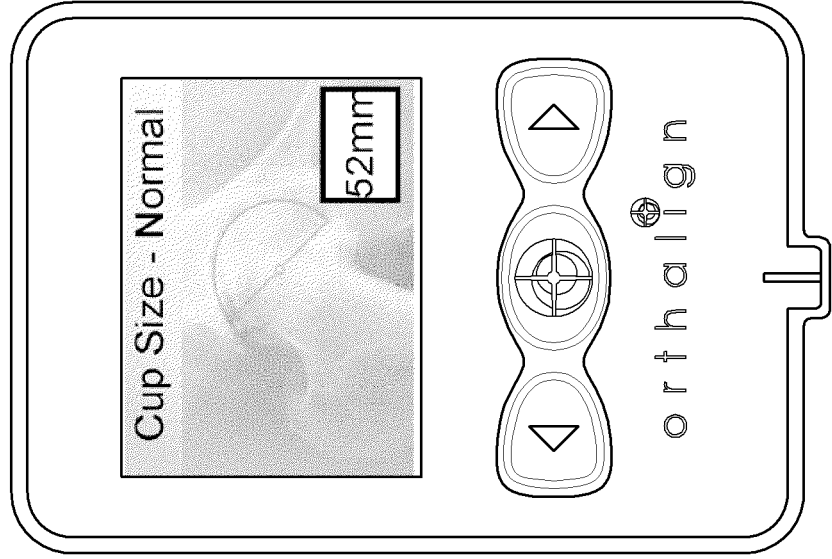
Figure 30G:
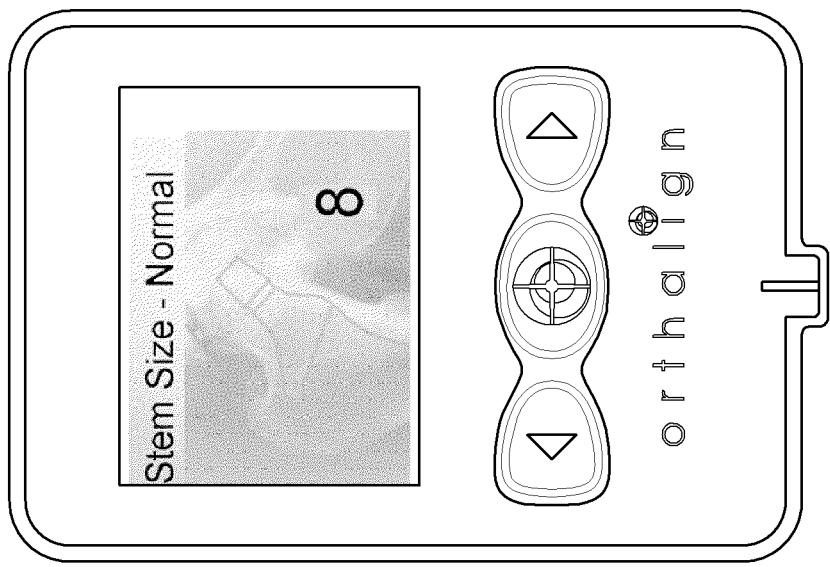
Figure 30F:
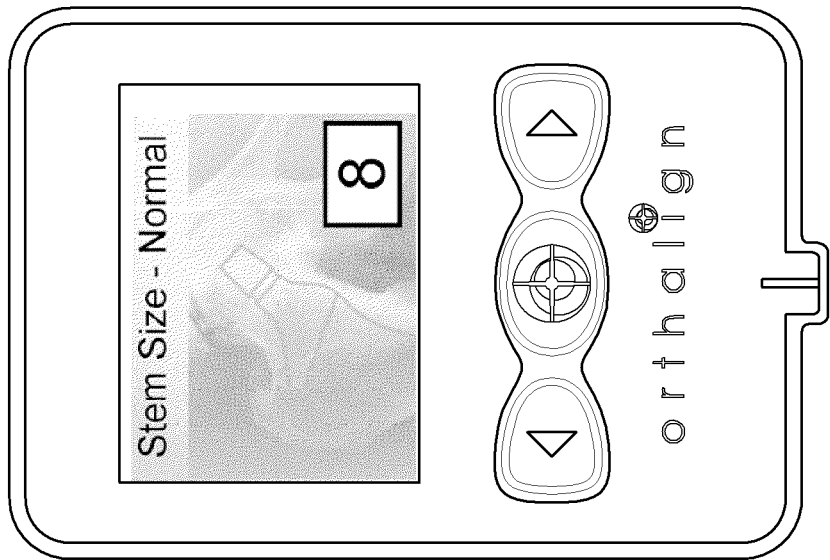
Figure 30E:
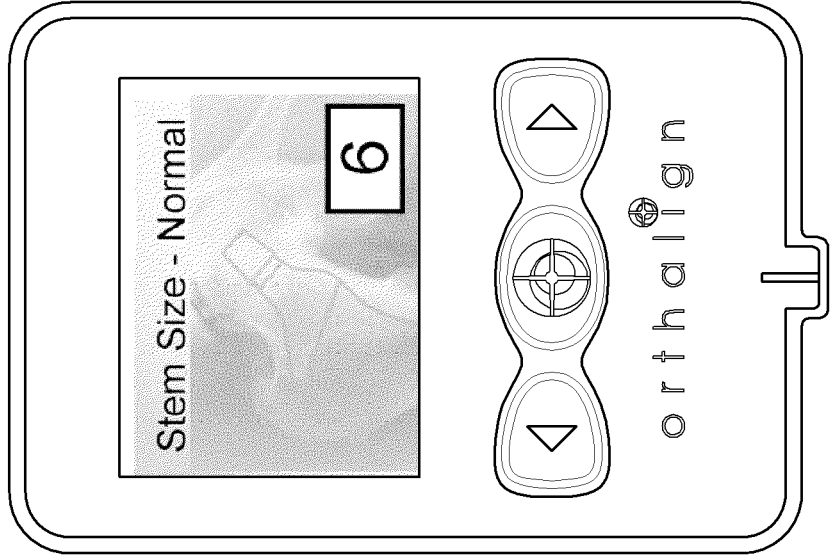
Figure 30J:
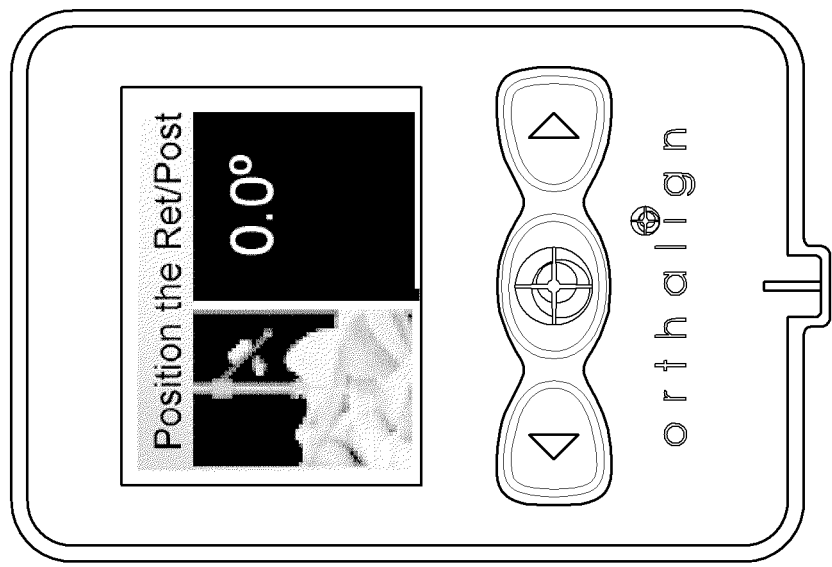
Figure 30I:
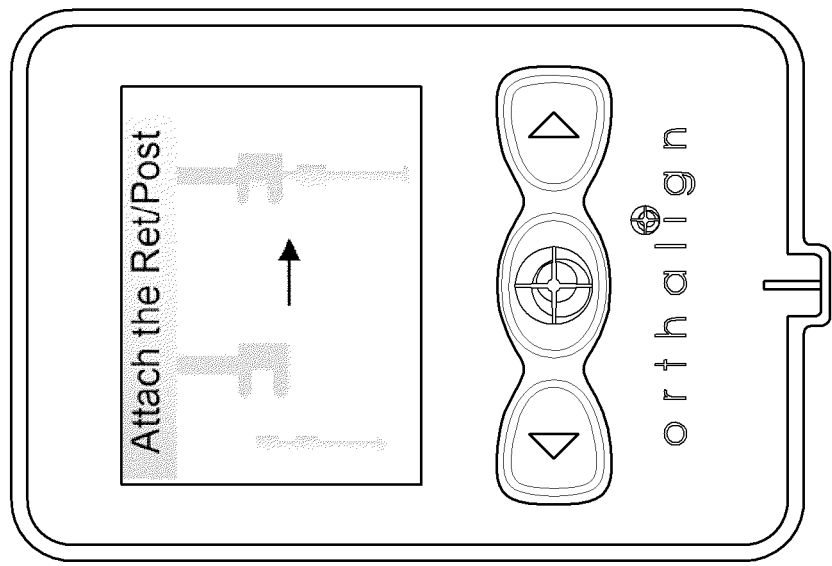
Figure 30H:
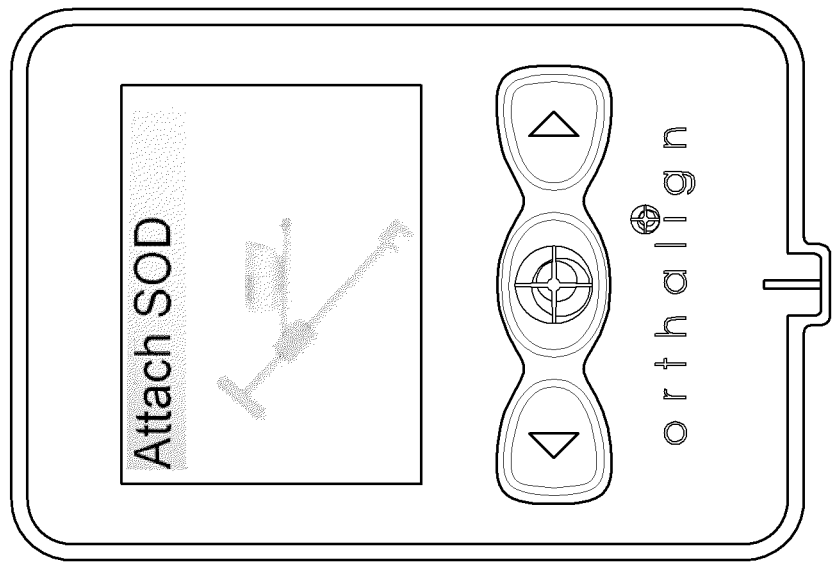
Figure 30M:
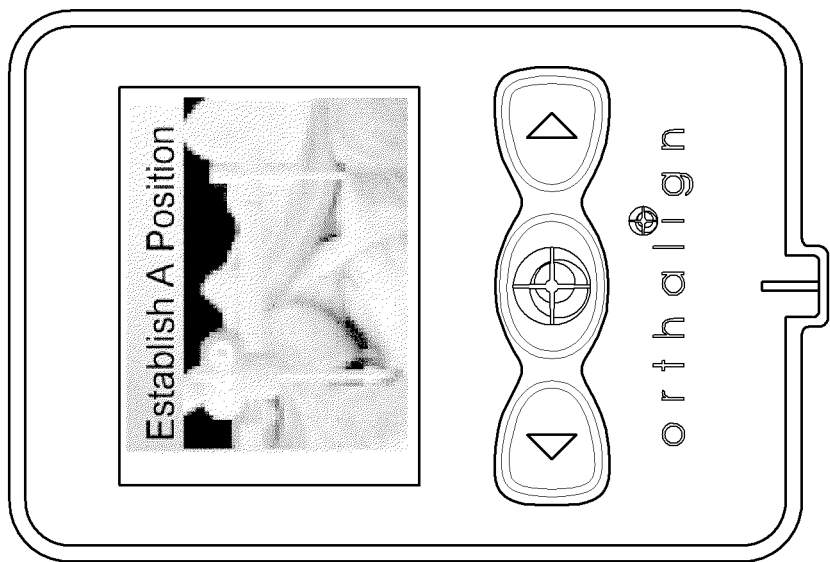
Figure 30L:
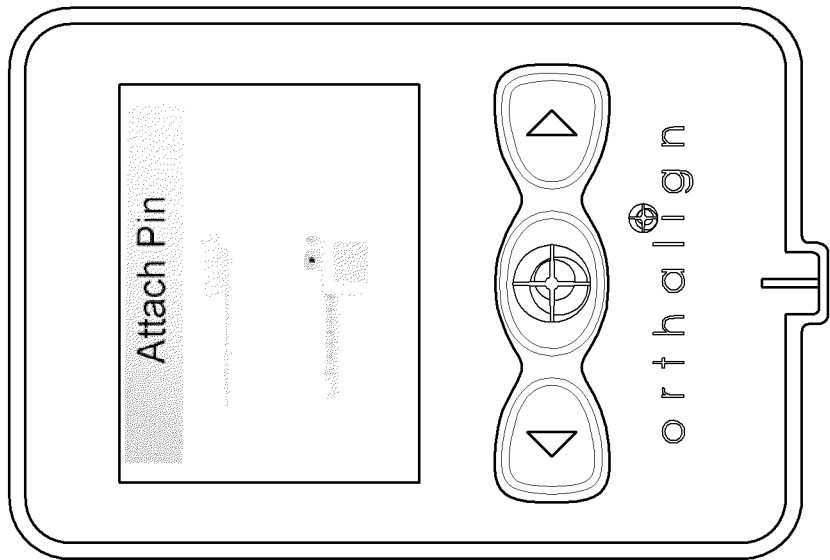
Figure 30K:
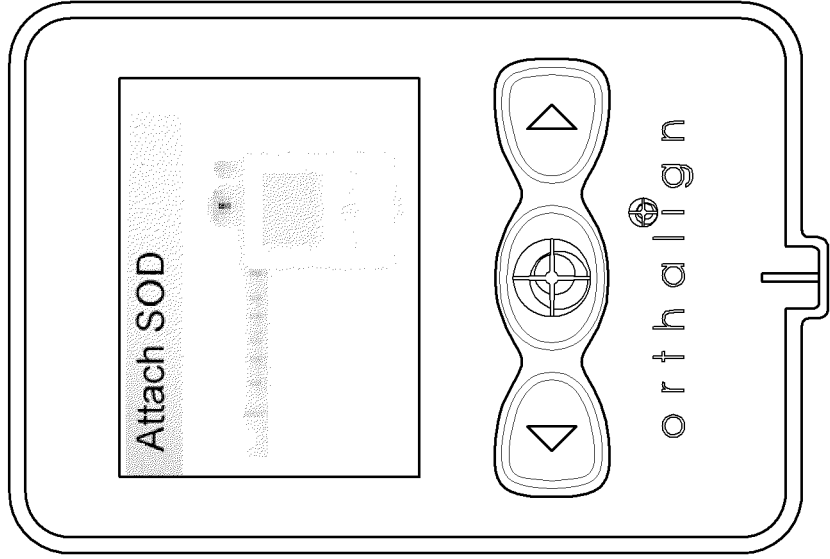
Figure 30P:
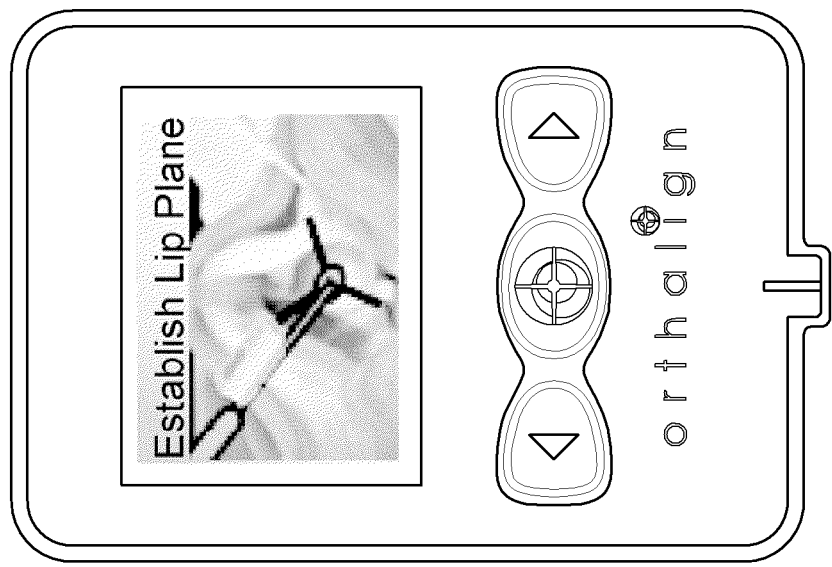
Figure 30O:
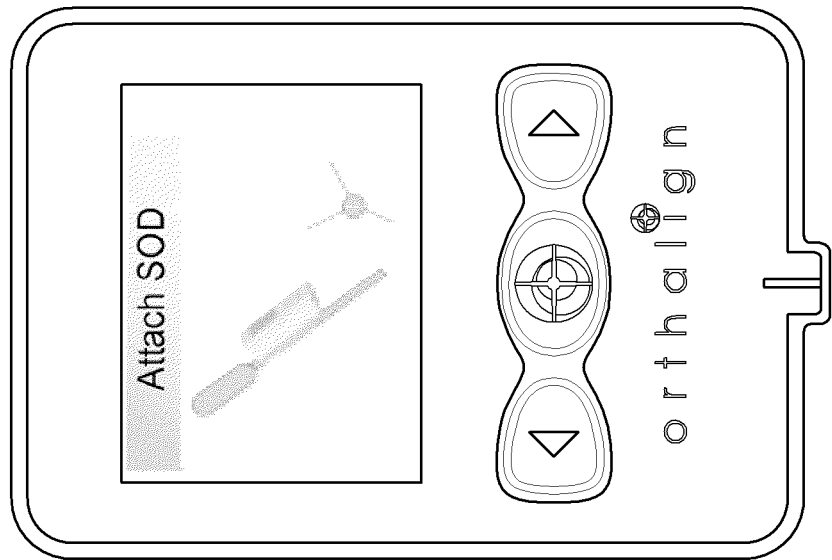
Figure 30N:
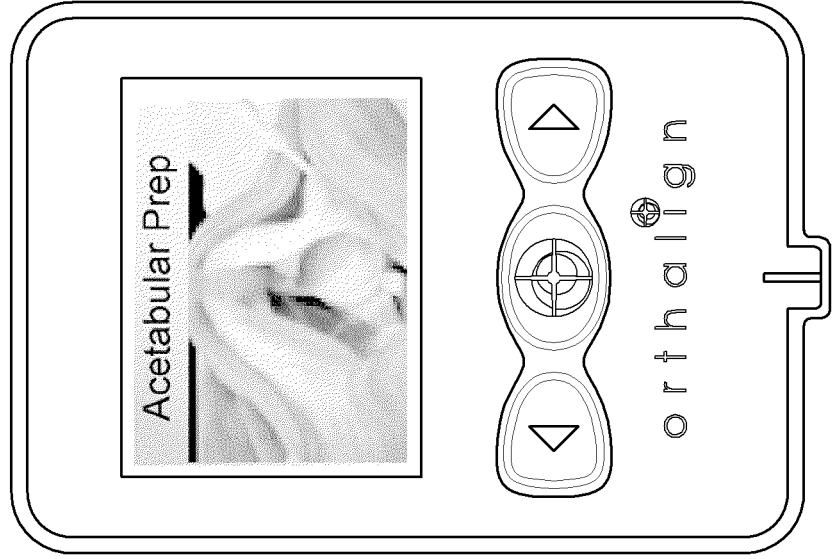
Figure 30S:
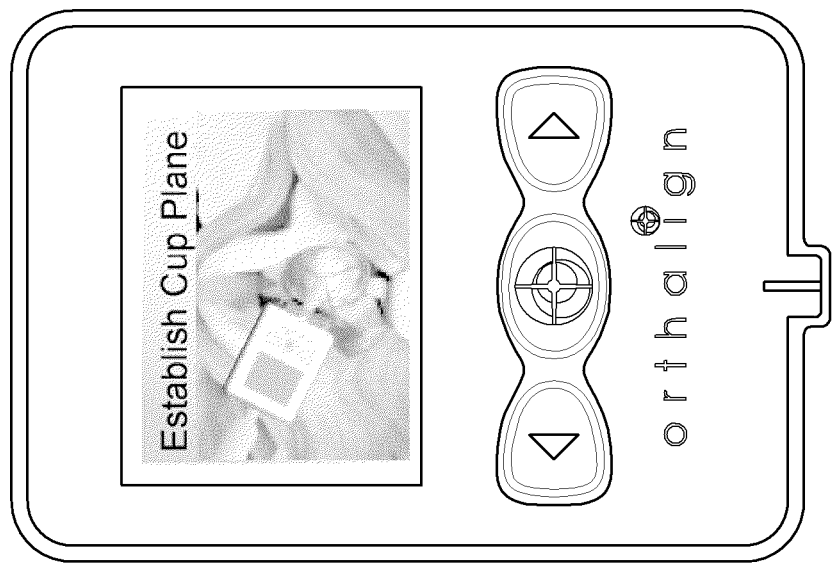
Figure 30R:
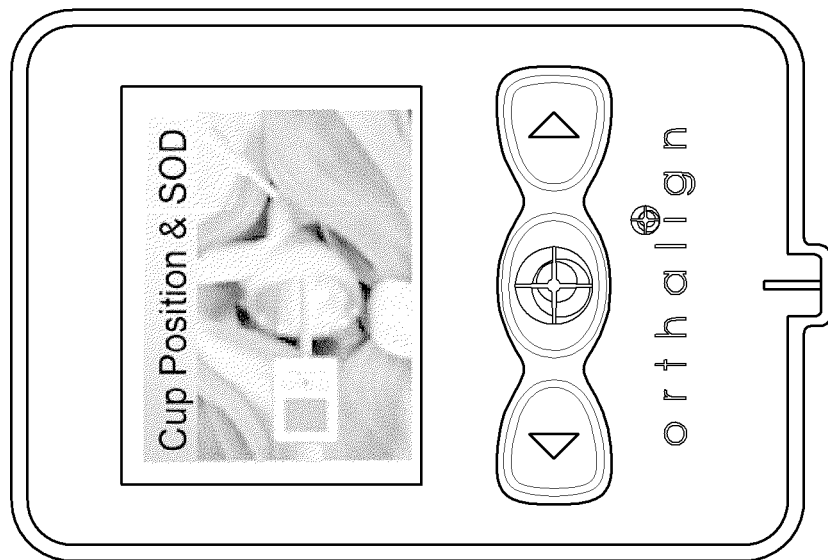
Figure 30Q:
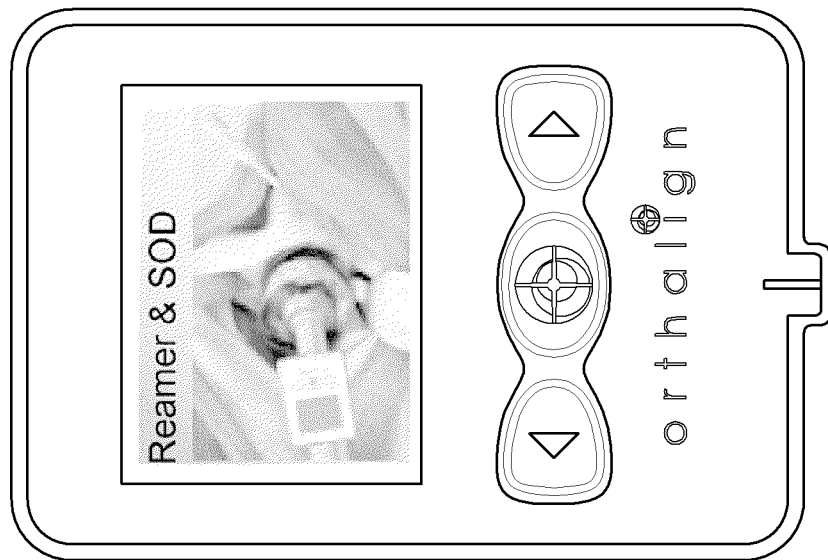
Figure 30V:
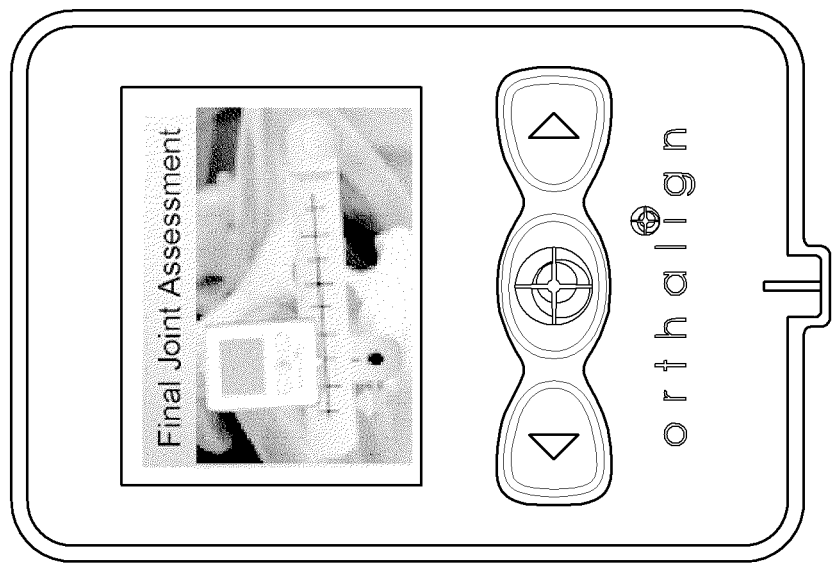
Figure 30U:
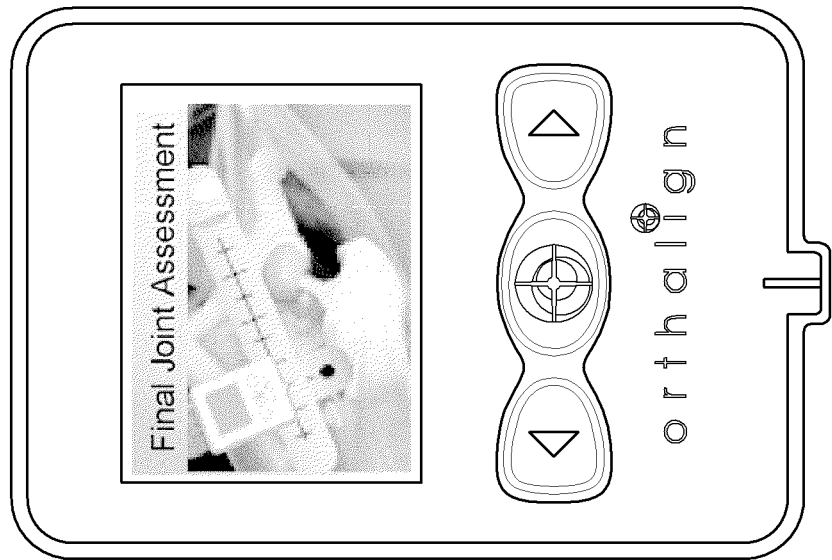
Figure 30T:
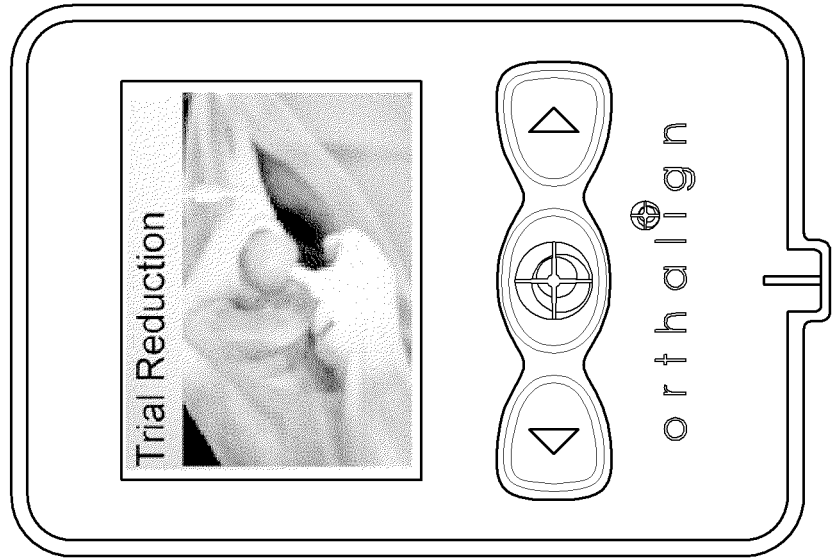
Figure 30W:
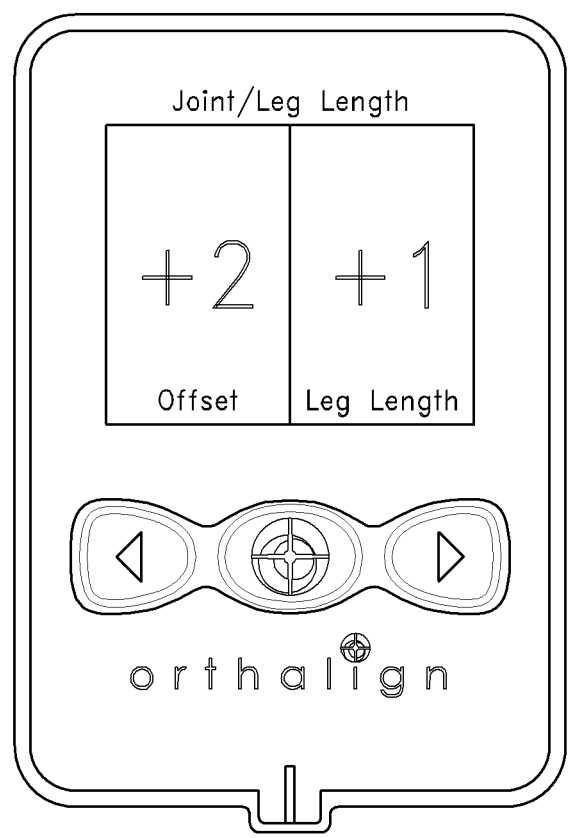

FIG. 30A-W show various screen shots which can form part of the interactive user interface or interfaces described above. The screen shots can be seen, for example, on a display of the surgical orientation device 12.

As shown in FIG. 30A, an interface screen can illuminate requesting the user to press a user input, e.g., a center button on the surgical orientation device 12. Thereafter, a message can be displayed indicating to the user that the surgical orientation device 12 is preparing for operation. The message can be a display of text on a screen, as illustrated in FIG. 30A, an audible sound, or other signal to the user to wait for the device to confirm a proper operational state. For example, a variety of self-tests can be performed. In one embodiment, information about the operating system, such as its version, can be displayed for review.

FIG. 30B shows a user interface screen which indicates that a range of potential cup size templates are available. For example, the user interface screen can indicate a "52" size.

FIG. 30C shows a user interface screen requesting the user to scroll through template options. For example, the user can press a side toggle button to scroll through cup size template options.

FIG. 30D shows a user interface screen in which a user has selected a "48" size cup implant. The selection can be made by pressing a middle button below the display screen on the surgical orientation device 12. This selection of cup size can be based on a user's pre-operative assessment of a patient.

FIGS. 30E-G show user interface screens similar to those of FIGS. 30B-D, in which a user can scroll through and select an appropriate stem size template.

FIG. 30H shows a user interface screen providing input to a user to attach the surgical orientation device 12 to the angle assessment guide 18. The user can press a user input (e.g. an enter button) on the surgical orientation device 12 to indicate completion of this step.

FIG. 30I shows a user interface screen providing input to a user to attach the reference post 14 to the impactor 16. The user can press a user input (e.g. an enter button) on the surgical orientation device 12 to indicate completion of this step.

FIG. 30J shows a user interface screen providing information on the orientation of the system 10 to guide the user in proper orientation while the reference post 14 is impacted into patient.

FIG. 30K shows a user interface screen providing instructions to a user to attach the surgical orientation device 12 to the system 110. The user can press a user input (e.g. an enter button) to indicate completion of this step.

FIG. 30L shows a user interface screen providing instructions to a user to attach the marking device 118 to the system 110. The user can press a user input (e.g. an enter button) to indicate completion of this step.

FIG. 30M shows a user interface screen providing instructions to establish the position of the marking device 118 in system 110, with the marking device 118 referencing an anatomical landmark determined by the user. Once the user has contacted the anatomical landmark, the user can press a button (e.g. an enter button) to record an orientation of the system 110 with respect to that landmark.

FIG. 30N shows a user interface screen providing instructions to a user to prepare the acetabulum for cup implantation. The user can press a user input (e.g. an enter button) to indicate completion of this step.

FIG. 30O shows a user interface screen providing instructions to a user to attach the surgical orientation device 12 to the system 210. The user can press a user input (e.g. an enter button) to indicate completion of this step.

FIG. 30P shows a user interface screen providing instructions to a user to assess a plane of the acetabulum. The user can press a user input (e.g. an enter button) to indicate completion of this step.

FIG. 30Q shows a user interface screen providing instructions to a user to ream the acetabulum using system 310, as well as providing feedback to the user on the orientation of the reamer (with the surgical orientation device 12 attached) so that user can use the reamer in accordance with the plane established by acetabular lip assessment guide. The user can press a user input (e.g. an enter button) to indicate completion of this step.

FIG. 30R shows a user interface screen providing instructions to a user to position a prosthetic cup 414 in the acetabulum. The user can press a user input (e.g. an enter button) to indicate completion of this step.

FIG. 30S shows a user interface screen providing instructions to a user to impact the prosthetic cup into the acetabulum using the system 410, as well as providing feedback to the user on the orientation of the prosthetic cup (with the surgical orientation device 12 attached) so that the user can impact the cup in accordance with the plane established by the system 210. The user can press a user input (e.g. an enter button) to indicate completion of this step.

FIG. 30T shows a user interface screen providing instructions to the user to fit a trial hip implant. The user can press a user input (e.g. an enter button) to indicate completion of this step.

FIGS. 30U, 30V show a user interface screen providing instructions to the user to assess the orientation of the system 110 with respect to the anatomical landmark that was previously assessed by the marking device 118 on the system 110. The user can measure the distance again from the reference post 14 to the landmark measure previously.

FIG. 30W shows a user interface screen displaying leg length and joint off-set changes based on orientation changes of jigging system from initial assessment of anatomical landmark in FIG. 13 and final assessment in FIG. 22.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments can be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A method for assisting a surgeon, comprising:
   providing an orientation device comprising a display and at least one inertial sensor;
   coupling the orientation device to a first location relative to an acetabulum of a patient, wherein the orientation device records a reference orientation at the first location;
   transitioning the orientation device to a second location on a medical tool, wherein the orientation device determines an orientation of the medical tool relative to the reference orientation at the second location; and
   moving the medical tool relative to an acetabulum for implantation of an acetabular cup.

2. The method of claim 1, wherein the orientation device measures orientation relative to gravity.

3. The method of claim 1, wherein an angle measurement is presented on the display.

4. The method of claim 1, wherein the orientation device performs calculations.

5. The method of claim 1, wherein the orientation device converts data from a machine-readable format to a human readable format for presentation on the display.

6. The method of claim 1, wherein the orientation device comprises one or more processors.

7. The method of claim 1, wherein the orientation device comprises memory.

8. The method of claim 1, wherein the at least one inertial sensor comprises a gyroscopic sensor, an accelerometer sensor, or a magnetometer.

9. The method of claim 1, wherein the patient is in a supine position.

10. The method of claim 1, wherein a direction of rotation is presented on the display.

11. A method for assisting a surgeon, comprising:
    providing an orientation device comprising a display and at least one inertial sensor;
    coupling the orientation device to a first location, wherein the orientation device records a reference orientation at the first location;
    transitioning the orientation device to a second location on a medical tool, wherein the orientation device determines an orientation of the medical tool relative to the reference orientation at the second location; and
    moving the medical tool relative to an acetabulum for implantation of an acetabular cup.

12. The method of claim 11, wherein an angle measurement is presented on the display.

13. The method of claim 11, wherein the orientation device records the reference orientation at the first location relative to gravity.

14. The method of claim 11, wherein the orientation device converts data from at least one inertial sensor to signals for presentation on the display.

15. The method of claim 11, wherein the at least one inertial sensor comprises at least one accelerometer.

16. The method of claim 11, wherein the patient is in a supine position.

17. A method for assisting a surgeon, comprising:
    providing an orientation device comprising a display and at least one inertial sensor;
    coupling the orientation device to a first location, wherein the orientation device records a reference measurement at the first location;
    transitioning the orientation device to a second location on a medical tool; and
    moving the medical tool relative to an acetabulum for implantation of an acetabular cup, wherein the orientation device determines changes relative to the reference measurement after implantation of the acetabular cup.

18. The method of claim 17, further comprising positioning the patient in a supine position.

19. The method of claim 17, wherein an angle measurement of the acetabular cup relative to the reference plane is presented on the display.

20. The method of claim 17, wherein the first location is fixed and spaced apart from an acetabulum of a patient.

* * * * *